(12) United States Patent
Luo et al.

(10) Patent No.: US 11,053,322 B2
(45) Date of Patent: *Jul. 6, 2021

(54) APOLIPOPROTEIN NANODISCS WITH TELODENDRIMER

(71) Applicant: LAWRENCE LIVERMORE NATIONAL SECURITY, LLC, Livermore, CA (US)

(72) Inventors: Juntao Luo, Jamesville, NY (US); Wei He, Davis, CA (US); Kit S. Lam, Davis, CA (US); Paul Henderson, Dublin, CA (US); Matthew A. Coleman, Oakland, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/499,855

(22) Filed: Apr. 27, 2017

(65) Prior Publication Data
US 2018/0079829 A1  Mar. 22, 2018

Related U.S. Application Data

(63) Continuation of application No. 13/719,785, filed on Dec. 19, 2012, now Pat. No. 9,644,038.

(60) Provisional application No. 61/578,583, filed on Dec. 21, 2011.

(51) Int. Cl.
C07K 17/02 (2006.01)
C07K 14/775 (2006.01)

(52) U.S. Cl.
CPC ............ *C07K 17/02* (2013.01); *C07K 14/775* (2013.01)

(58) Field of Classification Search
None
See application file for complete search history.

(56) References Cited

U.S. PATENT DOCUMENTS

| | | | |
|---|---|---|---|
| 4,317,771 A | 3/1982 | Shiba et al. |
| 5,393,530 A | 2/1995 | Schneider et al. |
| 6,270,649 B1 | 8/2001 | Zeikus et al. |
| 6,599,527 B1 | 7/2003 | Leigh et al. |
| 7,015,471 B2 | 3/2006 | Franzen et al. |
| 7,048,949 B2 | 5/2006 | Sligar et al. |
| 7,375,234 B2 | 5/2008 | Sharpless et al. |
| 7,575,763 B2 | 8/2009 | Sligar et al. |
| 7,592,008 B2 | 9/2009 | Sligar et al. |
| 7,622,437 B2 | 11/2009 | Morrissey et al. |
| 7,662,410 B2 | 2/2010 | Sligar et al. |
| 7,691,414 B2 | 4/2010 | Sligar et al. |
| 8,183,010 B2 | 5/2012 | Swartz et al. |
| 8,268,796 B2 | 9/2012 | Ryan |
| 8,883,729 B2 | 11/2014 | Hoeprich et al. |
| 8,889,623 B2 | 11/2014 | Hoeprich et al. |
| 8,895,055 B2 | 11/2014 | Lam et al. |
| 8,907,061 B2 | 12/2014 | Chromy et al. |
| 9,303,273 B2 | 4/2016 | Hoeprich et al. |
| 9,388,232 B2 | 7/2016 | Dasseux et al. |
| 9,458,191 B2 | 10/2016 | Chromy et al. |
| 9,644,038 B2 * | 5/2017 | Luo ..................... C07K 14/775 |
| 9,688,718 B2 | 6/2017 | Baker et al. |
| 10,151,037 B2 | 12/2018 | Hoeprich, Jr. et al. |
| 2001/0051131 A1 | 12/2001 | Unger |
| 2003/0008014 A1 | 1/2003 | Shelness |
| 2004/0101741 A1 | 5/2004 | Minteer et al. |
| 2004/0180369 A1 | 9/2004 | Franzen et al. |
| 2005/0182243 A1 | 8/2005 | Sligar et al. |
| 2005/0244414 A1 | 11/2005 | Mundy et al. |
| 2006/0127467 A1 | 6/2006 | Watkin |
| 2006/0189554 A1 | 8/2006 | Mumper et al. |
| 2006/0211092 A1 | 9/2006 | Sligar et al. |
| 2007/0101448 A1 | 5/2007 | Anantharamiah et al. |
| 2007/0287034 A1 | 12/2007 | Minteer et al. |
| 2008/0124350 A1 | 5/2008 | Mumper et al. |
| 2009/0203549 A1 | 8/2009 | Hoeprich, Jr. et al. |
| 2009/0270331 A1 | 10/2009 | Remaley et al. |

(Continued)

FOREIGN PATENT DOCUMENTS

| | | |
|---|---|---|
| EP | 3426304 A1 | 1/2019 |
| JP | 2008516605 A | 5/2008 |

(Continued)

OTHER PUBLICATIONS

Dalkara et al. "Intracytoplasmic Delivery of Anionic Proteins" Molecular Therapy, Jun. 2004, vol. 9, No. 6, pp. 964-969.
He et al. "Controlling the diameter, monodispersity, and solubility of ApoA1 nanolipoprotein particles using telodendrimer chemistry" Protein Science, 2013, vol. 22, pp. 1078-1086.
Semple et al. "Rational design of cationic lipids for siRNA delivery" Nature Biotechnology, Feb. 2010, vol. 28, No. 2, pp. 172-176 + 2 additional pages.
Xiao et al. "A self-assembling nanoparticle for paclitaxel delivery in ovarian cancer" published in Biomaterials, Oct. 2009, vol. 30, No. 30, pp. 6006-6016. Author Manuscript. 24 pages.
Zuris et al. "Cationic lipid-mediated delivery of proteins enables efficient protein-based genome editing in vitro and in vivo" Nature Biotechnology, Jan. 2015, vol. 33, No. 1, pp. 73-80.

(Continued)

*Primary Examiner* — Anand U Desai
(74) *Attorney, Agent, or Firm* — Steinfl + Bruno LLP

(57) ABSTRACT

The present invention provides a nanodisc with a membrane scaffold protein. The nanodisc includes a membrane scaffold protein, a telodendrimer and a lipid. The membrane scaffold protein can be apolipoprotein. The telodendrimer has the general formula PEG-L-D-(R)$_n$, wherein D is a dendritic polymer; L is a bond or a linker linked to the focal point group of the dendritic polymer; each PEG is a polyethylene glycol) polymer; each R is and end group of the dendritic polymer, or and end group with a covalently bound hydrophobic group, hydrophilic group, amphiphilic compound, or drug; and subscript n is an integer from 2 to 20. Cell free methods of making the nanodiscs are also provided.

19 Claims, 14 Drawing Sheets
Specification includes a Sequence Listing.

(56) References Cited

U.S. PATENT DOCUMENTS

| | | |
|---|---|---|
| 2009/0324706 A1 | 12/2009 | Mirkin et al. |
| 2010/0203609 A1 | 8/2010 | Yacoby et al. |
| 2011/0059549 A1 | 3/2011 | Coleman et al. |
| 2011/0178029 A1 | 7/2011 | Knudsen et al. |
| 2011/0178164 A1 | 7/2011 | Cunha et al. |
| 2011/0195450 A1 | 8/2011 | Kudlicki et al. |
| 2012/0148642 A1 | 6/2012 | Remaley et al. |
| 2012/0245101 A1 | 9/2012 | Anantharamaiah et al. |
| 2013/0165636 A1 | 6/2013 | Luo et al. |
| 2014/0273142 A1 | 9/2014 | Hoeprich |
| 2014/0308341 A1 | 10/2014 | Fujii et al. |
| 2015/0140108 A1 | 5/2015 | Peer et al. |
| 2016/0083858 A1 | 3/2016 | Hoeprich, Jr. et al. |
| 2016/0235671 A1 | 8/2016 | Li et al. |
| 2016/0324923 A1 | 11/2016 | Dasseux et al. |
| 2018/0186860 A1 | 7/2018 | Hoeprich, Jr. et al. |
| 2018/0318218 A1 | 11/2018 | Kamrud et al. |
| 2019/0055658 A1 | 2/2019 | Hoeprich, Jr. et al. |
| 2019/0094230 A1 | 3/2019 | Coleman et al. |
| 2019/0142752 A1 | 5/2019 | Blanchette et al. |
| 2019/0307692 A1 | 10/2019 | Blanchette et al. |
| 2020/0046848 A1 | 2/2020 | Coleman et al. |

FOREIGN PATENT DOCUMENTS

| | | |
|---|---|---|
| JP | 2015110677 A | 6/2015 |
| WO | 99/59550 A1 | 11/1999 |
| WO | 00/65099 A1 | 11/2000 |
| WO | 02/40501 A2 | 5/2002 |
| WO | 2004/094651 A2 | 11/2004 |
| WO | 2004/112214 A2 | 12/2004 |
| WO | 2005/070400 A1 | 8/2005 |
| WO | 2006/073419 A2 | 7/2006 |
| WO | 2007/038755 A1 | 4/2007 |
| WO | 2007/050501 A2 | 5/2007 |
| WO | 2007/053655 A2 | 5/2007 |
| WO | 2008/028206 A2 | 3/2008 |
| WO | 2008/106660 A2 | 9/2008 |
| WO | 2009/100201 A2 | 8/2009 |
| WO | 2010/039496 A2 | 4/2010 |
| WO | 2010/040897 A1 | 4/2010 |
| WO | 2014/063097 A1 | 4/2014 |
| WO | 2017/035326 A1 | 3/2017 |
| WO | 2017/044899 A1 | 3/2017 |
| WO | 2017/155837 A1 | 9/2017 |
| WO | 2018/204421 A2 | 11/2018 |

OTHER PUBLICATIONS

Aina O.H., et al., "From combinatorial chemistry to cancer-targeting peptides" Mol Pharm, vol. 4, No. 5, pp. 631-651 (2007).
Badamchi-Zadeh A, et al., "A multi-component prime-boost vaccination regimen with a consensus MOMP antigen enhances chlamydia trachomatis clearance." Frontiers in Immunology, vol. 7, Article 162, pp. 1-11 (Apr. 2016).
Baehr W, et al., "Mapping antigenic domains expressed by Chlamydia trachomatis major outer membrane protein genes." Proceeding of the National Academy of Sciences, vol. 85, pp. 4000-4004 (1988).
Bayburt T.H., et al., "Assembly of single bacteriorhodopsin trimers in bilayer nanodiscs" Arch Biochem Biophys, 450, pp. 215-222 (2006).
Bayburt T.H., et al., "Self-assembly of Discoidal Phospholipid Bilayer Nanoparticles with Membrane Scaffold Proteins" Nano Lett, vol. 2, No. 8, pp. 853-856 (2002).
Bayburt T.H., et al., "Transducin activation by nanoscale lipid bilayers containing one and two rhodopsins" J Biol Chem, vol. 282, No. 20, pp. 14875-14881 (2007).
Blanchette C.D., et al., "Atomic force microscopy differentiates discrete size distributions between membrane protein containing and empty nanolipoprotein particles." Biochim Biophys Acta., 1788, pp. 724-731 (Mar. 2009).
Blanchette C.D., et al., "Kinetic analysis of his-tagged protein binding to nickel-chelating nanolipoprotein particles." Bioconjug Chem, 21, pp. 1321-1330 (Jul. 2010).
Blanchette C.D., et al., "Quantifying size distributions of nanolipoprotein particles with single-particle analysis and molecular dynamic simulations" J Lipid Res, vol. 49, pp. 1420-1430 (2009).
Cappuccio JA, et al., "Cell-free Co-expression of Functional Membrane Proteins and Apolipoprotein, Forming Soluble Nanolipoprotein Particles." Mol Cell Proteomics, 7.11, pp. 2246-2253 (2008).
Carmichael J.R. et al., "Induction of protection against vaginal shedding and infertility by recombinant Chlamydia vaccine" Vaccine, 29, pp. 5276-5283 (2011).
Chromy BA, et al., "Different apolipoproteins impact nanolipoprotein particle formation" J Am Chem Soc, 219, pp. 14348-14354 (Nov. 2007).
Coleman M.A, et al., "Expression and Association of the Yersinia pestis Translocon Proteins, YopB and YopD, Are Facilitated by Nanolipoprotein Particles." PLoS One p. e0150166 (2016). 16 pages.
Conlan J, et al., "Isolation of recombinant fragments of the major outer-membrane protein of Chlamydia trachomatis: their potential as subunit vaccines" Microbiology, 136, pp. 2013-2020 (1992).
Davidson E, et al., "A high-throughput shotgun mutagenesis approach to mapping B-cell antibody epitopes" Immunology, 143, pp. 13-20 (2014).
Farris C.M. et al., "CD4+ T cells and antibody are required for optimal major outer membrane protein vaccine-induced immunity to Chlamydia muridarum genital infection" Infection and Immunity, vol. 78, No. 10, pp. 4374-4383 (2010).
Feher V.A. et al., "A 3-dimensional trimeric B-barrel model for Chlamydia MOMP contains conserved and novel elements of Gram-negative bacterial porins." PloS one p. e68934, vol. 8, Issue 7 (2013). 11 pages.
Findlay H.E, et al., "Surface expression, single-channel analysis and membrane topology of recombinant Chlamydia trachomatis Major Outer Membrane Protein" BMC Microbiol, 5:5 (2005). 15 pages.
Frydman J, et al., "Principles of chaperone-assisted protein folding: differences between in vitro and in vivo mechanisms" Science, vol. 272, pp. 1497-1502 (Jun. 1996). 7 pages.
Gao T, et al., "Characterizing diffusion dynamics of a membrane protein associated with nanolipoproteins using fluorescence correlation spectroscopy" Protein Sci., vol. 20, pp. 437-447 (Feb. 2011).
Ghosh M, et al., "Cationic lipid Nanodisks as an siRNA delivery vehicle" Biochem Cell Biol (2014), 92(3): 200-205. 14 pages.
Haque F, et al., "Incorporation of a viral DNA-packaging motor channel in lipid bilayers for real-time, single-molecule sensing of chemicals and double-stranded DNA." Nat Protoc, vol. 8, No. 2, pp. 373-392 (2013).
He W, et al., "Cell-free expression of functional receptor tyrosine kinases" Sci Rep, 5:12896 (2015). 8 pages.
He W, et al., "Producing Membrane Bound Proteins as Countermeasures to infectious Diseases" Synthetic Genomics Vaccines (2016).
Inic-Kanada A, et al., "A Probiotic Adjuvant Lactobacillus rhamnosus Enhances Specific Immune Responses after Ocular Mucosal Immunization with Chlamydial Polymorphic Membrane Protein C." PLoS One p. e015785 (2016) 14 pages.
International Search Report for International Application No. PCT/US2018/030537 filed on May 1, 2018 on behalf of Lawrence Livermore National Security dated Jan. 17, 2019 5 pages.
Johnson R.M. et al., "PmpG 303-311, a protective vaccine epitope that elicits persistent cellular immune responses in Chlamydia muridarum-immune mice." Infect Immun, vol. 80, No. 6, p. 2204-2211 (2012).
Jonas A, et al., "Reconstitution of high-density lipoproteins" Methods Enzymol, vol. 128, pp. 553-582 (1986).
Karunakaran K.P. et al., "Immunoproteomic discovery of novel T cell antigens from the obligate intracellular pathogen Chlamydia" J Immunol p. 2459-65 (2008).
Karunakaran K.P. et al., "Outer membrane proteins preferentially load MHC class II peptides: implications for a Chlamydia trachomatis T cell vaccine." Vaccine, 33, p. 2159-2166 (2015).

(56) References Cited

OTHER PUBLICATIONS

Katzen F, et al., "Insertion of membrane proteins into discoidal membranes using a cell-free protein expression approach" J Proteome Res, 7, pp. 3535-3542 (2008).
Keppetipola S, et al., From gene to HSQC in under five hours: high-throughput NMR proteomics: J Am Chem Soc, 128, pp. 4508-4509 (Apr. 2006).
Kigawa T, et al., "Cell-free production and stable-isotope labeling of milligram quantities of proteins" FEBS Lett, 442, pp. 15-19 (Jan. 1999).
Klammt C, et al.,"Evaluation of detergents for the soluble expression of alpha-helical and beta-barrel-type integral membrane proteins by a preparative scale individual cell-free expression system." FEBS J., 272, pp. 6024-6038 (Dec. 2005).
Klussman S, et al., "The Aptamer Handbook: Functional Oligonucleotides and Their Applications" *Wiley-VCH* (2006) 509 pages.
Koren E, et al., "Clinical validation of the "in silico" prediction of immunogenicity of a human recombinant therapeutic protein" Clinical Immunology, 124, pp. 26-32 (2007).
Lam K, et al., "A new type of synthetic peptide library for identifying ligand-binding activity" Nature, vol. 354, pp. 82-84 (1991).
Levy-Nissenbaum E. et al., "Nanotechnology and aptamers: applications in drug delivery" *Trends in Biotechnology*26(8):442-449 (2008).
Luo J, et al., "Well-defined, size-tunable, multifunctional micelles for efficient paclitaxel delivery for cancer treatment." Bioconjug Chem, 21, pp. 1216-1224 (Jul. 2010).
Manning D.S. et al., "Expression of the major outer membrane protein of Chlamydia trachomatis in *Escherichia coli*." Infection and Immunity, vol. 61, No. 10, pp. 4093-4098 (1993).
Mori M, et al., "Cell-free synthesis and processing of a putative precursor for mitochondrial carbamyl phosphate synthetase I of rat liver" Proc Natl Acad Sci USA, vol. 76, No. 10, pp. 5071-5075 (Oct. 1979).
Nath A, et al., "Applications of Phospholipid Bilayer Nanodiscs in the Study of Membranes and Membrane Proteins" Biochemistry, vol. 46, No. 8, pp. 2059-2069 (2007).
Pal S, et al., "Comparison of the nine polymorphic membrane proteins of Chlamydia trachomatis for their ability to induce protective immune responses in mice against a C. muridarum challenge." Vaccine, 35, p. 2543-2549 (2017).
Pal S, et al., "Immunization with an acellular vaccine consisting of the outer membrane complex of Chlamydia trachomatis induces protection against a genital challenge" Infection and Immunity, vol. 65, No. 8, pp. 3361-3369 (1997).
Pal S, et al., "Immunization with the Chlamydia trachomatis mouse pneumonitis major outer membrane protein can elicit a protective immune response against a genital challenge" Infection and immunity, vol. 65, No. 10, pp. 6240-6247 (2001).
Pal S, et al., "Vaccination with the Chlamydia trachomatis major outer membrane protein can elicit an immune response as protective as that resulting from inoculation with live bacteria" Infection and Immunity, vol. 73, No. 12, pp. 8153-8160 (2005).
Ralli-Jain P, et al., "Enhancement of the protective efficacy of a Chlamydia trachomatis recombinant vaccine by combining systemic and mucosal routes for immunization." Vaccine, 28, pp. 7659-7666 (2010).
Rensen PC, et al., "Human recombinant apolipoprotein E-enriched liposomes can mimic low-density lipoproteins as carriers for the site-specific delivery of antitumor agents." Mol Pharmacol, 52, pp. 445-455 (Sep. 1997).
Rodriguez-Maranon M.J. et al., "Prediction of the membrane-spanning Beta-strands of the major outer membrane protein of Chlamydia" Protein Science, 11, pp. 1854-1861 (2006).
Ryan RO, "Nanobiotechnology applications of reconstituted high density lipoprotein" J Nanobiotechnology, 8:28 (Dec. 2010) 10 pages.
Ryan RO, "Nanodisks: hydrophobic drug delivery vehicles" Expert Opin Drug Deliv., 5(3), pp. 343-351 (Mar. 2008).

Ferrara L.G.M. et al., "MOMP from Campylobacter jejuni is a Trimer of 18-Stranded beta-Barrel Monomers with a Ca(2+) Ion Bound at the Constriction Zone." J Mol Biol (2016), 428(22), pp. 4528-4543. 16 pages.
Sperling R.A. et al., "Surface modification, functionalization and bioconjugation of colloidal inorganic nanoparticles" Philosophical Transactions of the Royal Society A, 386, pp. 1333-1383 (2010).
Su H, et al., "Immunogenicity of a chimeric peptide corresponding to T helper and B cell epitopes of the Chlamydia trachomatis major outer membrane protein" Journal of Experimental Medicine, vol. 175, pp. 227-235 (1992).
Sun G, et al., "Protection against an intranasal challenge by vaccines formulated with native and recombinant preparations of the Chlamydia trachomatis major outer membrane protein" Vaccine, 27, pp. 5020-5025 (2009).
Sun G, et al., "Structural and functional analyses of the major outer membrane protein of Chlamydia trachomatis" J Bacteriol, vol. 189, No. 17, pp. 6222-6235 (2007).
Sunahara H, et al., "Design and synthesis of a library of BODIPY-based environmental polarity sensors utilizing photoinduced electron-transfer-controlled fluorescence On/Off switching" J Am Chem Soc., 129, pp. 5597-5604 (May 2007).
Tang G, et al., "EMAN2: an extensible image processing suite for electron microscopy" J Struct Biol, 157, pp. 38-46 (2007).
Tifrea D.F. et al., "Amphipols stabilize the Chlamydia major outer membrane protein and enhance its protective ability as a vaccine" Vaccine, 29, pp. 4623-4631 (2011).
Tifrea D.F. et al., "Increased immunoaccessibility of MOMP epitopes in a vaccine formulated with amphipols may account for the very robust protection elicited against a vaginal challenge with Chlamydia muridarum" The Journal of Immunology, 192, pp. 5201-5213 (2014).
Tu J, et al., "A multi-epitope vaccine based on Chlamydia trachomatis major outer membrane protein induces specific immunity in mice." Acta biochimica et biophysica Sinica, vol. 46, Issue 5, pp. 401-408 (2014).
Wang Y, et al., "Identification of surface-exposed components of MOMP of Chlamydia trachomatis serovar F." Protein Science, 15, pp. 122-134 (2006).
Whorton MR, et al., "A Monomeric G protein-coupled receptor isolated in a high-density lipoprotein particle efficiently activates its G protein" Proc Natl Acad Sci USA, vol. 104, No. 18, pp. 7682-7687 (2007).
Written Opinion for International Application No. PCT/US2018/030537 filed on May 1, 2018 on behalf of Lawrence Livermore National Security dated Jan. 17, 2019 9 pages.
Xiao K, et al., "Telodendrimer-based nanocarriers for the treatment of ovarian cancer." Ther Deliv, 4(10), pp. 1279-1292 (2013) 24 pages.
Yang JP, et al., "Cell-free synthesis of a functional G protein-coupled receptor complexed with nanometer scale bilayer discs." BMS Biotechnol, 11:57, (May 2011) 8 pages.
Abdulreda M.H., et al., "Atomic Force Microscope Spectroscopy Reveals a Hemifusion Intermediate during Soluble N-Ethylmaleimide-Sensitive Factor-Attachment Protein Receptors-Mediated Membrane Fusion," Biophysical Journal, Jan. 2008, vol. 94 (2), 648-655. 8 pages.
Abdulreda M.H., et al., "Atomic Force Microscope Studies of the Fusion of Floating Lipid Bilayers," *Biophysical Journal*,Jun. 2007, vol. 92 (12), 10 pages.
Advisory Action for U.S. Appl. No. 12/118,396, filed May 9, 2008, dated Jul. 7, 2015, 8 pages.
Advisory Action for U.S. Appl. No. 12/118,396, dated Jun. 7, 2012, 5 pages.
Advisory Action for U.S. Appl. No. 12/118,530, dated Jul. 23, 2015, 13 pages.
Bao P., et al., "High-Sensitivity Detection of DNA Hybridization on Microarrays Using Resonance Light Scattering," *Analytical Chemistry*,Apr. 2002, vol. 74 (8), 6 pages.
Bayburt T.H., et al., "Reconstitution and Imaging of a Membrane Protein in a Nanometer-size Phospholipid Bilayer," *Journal of Structural Biology*,Sep. 1998, vol. 123 (1), 8 pages.

(56) References Cited

OTHER PUBLICATIONS

Blanchette C.D., et al., "Characterization and Purification of Polydisperse Reconstituted Lipoproteins and Nanolipoprotein Particles," *International Journal of Molecular Sciences*,Jul. 2009, vol. 10 (7), 14 pages.

Boschker H.T.S., et al., "The Contribution of Macrophyte-derived Organic Matter to Microbial Biomass in Salt-marsh Sediments: Stable Carbon Isotope Analysis of Microbial Biomarkers," Limnology and Oceanography, 1999, vol. 44(2), 309-319. 11 pages.

Camarero J.A., et al., "Chemoselective Attachment of Biologically Active Protein to Surfaces by Expressed Protein Ligation and its Application for Protein Chip Fabrication," *Journal of the American Chemical Society*,Nov. 2004, vol. 126 (45), 2 pages.

Chen J.S., et al., "Amino Acids in SRS1 and SRS6 are Critical for Furanocoumarin Metabolism by CYP6B1v1, a Cytochrome P450 Monooxygenase," *Insect Molecular Biology*,Apr. 2002, vol. 11 (2), 12 pages.

Cleveland, T.E. IV, et al., "Small-angle X-ray and neutron scattering demonstrates that cell-free expression produces properly formed disc-shaped nanolipoprotein particles," Protein Science , Dec. 2017, vol. 27, pp. 780-789.

Coleman M., et al., "Asp 46 Can Substitute for Asp 96 as the Schiff Base Proton Donor in Bacteriorhodopsin," *Biochemistry*,Nov. 1995, vol. 34 (47), 8 pages.

Crankshaw C., Nanodisc Technology: A Revolutionary System for Study of Membrane Proteins, *Biofiles*,retrieved on Aug. 4, 2015, Retrieved from the Internet: URL: www.sigmaaldrich.com/teclmical-documents/articles!biofiles/nanodisc-technology.html, vol. 8, No. 20, 3 pages.

Definition of "homogeneous", Oxford Dictionaries, retrieved from en.oxforddictionaries.com/definition/homogeneous on Apr. 4, 2018, four pages.

Definition of Hydrogenase[online], Nov. 6, 2012[retrieved on Nov. 6, 2012], Retrieved from Internet: URL: en.wikipedia.org/wiki/Hydrogenase, 4 pages.

Denisov I.G., et al., "Nanodiscs in Membrane Biochemistry and Biophysics", Chemical Reviews, Mar. 2017, vol. 117 (6), 4669-4713. 92 pages.

Dong F., et al., "Endothelin-1 Enhances Oxidative Stress, Cell Proliferation and Reduces Apoptosis in Human Umbilical Vein Endothelial Cells: Role of ETB Receptor, NADPH oxidase and caveolin-1" *British Journal of Pharmacology*, Jun. 2005, vol. 145 (3), 323-333. 11 pages.

Dunn R.J., et al., "Structure-functions Studies on Bacteriorhodopsin," *The Journal of Biological Chemistry*,1987, vol. 262 (19), 9 pages.

Final Office Action for U.S. Appl. No. 12/118,396, dated Feb. 4, 2015, 29 pages.

Final Office Action for U.S. Appl. No. 12/118,396, dated Jan. 18, 2012, 17 pages.

Final Office Action for U.S. Appl. No. 12/118,396, dated Oct. 11, 2016, 29 pages.

Final Office Action for U.S. Appl. No. 12/118,396, dated Apr. 12, 2018, 25 pages.

Forstner M., et al., "Carboxyl-Terminal Domain of Human ApolipoproteinE: Expression, Purification,and Crystallization," *Protein Expression and Purification*,Nov. 1999, vol. 17 (2), 6 pages.

Forte T.M., et al., "Electron Microscope Study on Reassembly of Plasma High Density Apoprotein with Various Lipids," *Biochimica et Biophysica Acta*, Nov. 1971, vol. 248 (2), 6 pages.

Gao, T., et al., "Characterization of de novo synthesized GPCRs supported in nanolipoprotein discs," (2012) E.Pub, PloS One. 7(9):44911. 8 pages.

Gursky O., et al., "Compex of Human Apolipoprotein C-1 with Phospholipid: Thermodynamic or Kinetic Stability?," *Biochemistry*,Jun. 2002, vol. 41 (23), 12 pages.

Jayaraman S., et al., "Structural Basis for Thermal Stability of Human Low-density Lipoprotein," *Biochemistry*,Mar. 2005, vol. 44 (10), 7 pages.

Kalmbach R., et al., "Functional Cell-free Synthesis of a Seven Helix Membrane Protein: In Situ Insertion of Bacteriorhodopsin in Liposomes," *Journal of Molecular Biology*,Aug. 2007, vol. 371 (3), 10 pages.

Kim Y.P., et al., "Gold Nanoparticle-enhanced Secondary Ion Mass Spectrometry Imaging of Peptides on Self-assembled Monolayers," *Analytical Chemistry*,Mar. 2006, vol. 78(6), 8 pages.

Klammt C., et al., "Cell-free Expression as an Emerging Technique for the Large Scale Production of Integral Membrane Protein," *The FEBS Journal*,Sep. 2006, vol. 273 (18), 13 pages.

Klammt C., et al., "High Level Cell-free Expression and Specific Labeling of Integral Membrane Proteins," *European Journal of Biochemistry*,Feb. 2004, vol. 271 (3), 13 pages.

Lee J., et al., "Ab Initio Protein Structure Prediction: in From Protein Structure to Function with Bioinformatics," *Springer Science + Business Media B. V.*,2009, 23 pages.

Loll, PJ, "Membrane protein structural biology: the high throughput challenge", J. of Structural Biology, 142:144-153; 2003.

Lu B., et al., "Conformational Reorganization of the Four-helix Bundle of Human Apolipoprotein E in Binding to Phospholipid," The Journal of Biological Chemistry, Jul. 2000, vol. 275 (27), 7 pages.

Ly, S., et al., (Jan. 2014) "Quantifying interactions of a membrane protein embedded in lipid nanodisc using fluorescence correlation spectroscopy," Biophysical Journal. 106: L05-L08.

Ly, S., et al., "Quantifying membrane protein interactions in solution using fluorescence correlation spectroscopy," Biophysical Journal, (Aug. 15, 2013), LLNL-JRNL-642412. Lawrence Livermore National Laboratory. 11 pages.

Morrow J.A., et al., "Functional Characterization of Apolipoprotein E Isoforms Overexpressed in *Escherichia coli,*" *Protein Expression and Purification*,1999, vol. 16 (2), 7 pages.

Non-Final Office Action for U.S. Appl. No. 12/118,396, dated Aug. 30, 2011, 18 pages.

Non-Final Office Action for U.S. Appl. No. 12/118,396, dated Jan. 8, 2016, 32 pages.

Non-Final Office Action for U.S. Appl. No. 12/118,396, dated Jul. 22, 2014, 28 pages.

Non-Final Office Action for U.S. Appl. No. 12/118,396, dated Sep. 6, 2017, 14 pages.

Rao R.S., et al., "Comparison of Multiplexed Techniques for Detection of Bacterial and Viral Proteins," *Journal of Proteome Research*,Jul.-Aug. 2004, vol. 3(4), 7 pages.

Restriction Requirement for U.S. Appl. No. 12/118,396, dated Mar. 4, 2011, 14 pages.

Rusinol A.E., et al., "In Vitro Reconstitution of Assembly of Apolipoprotein B48-Containing Lipoproteins," *The Journal of Biological Chemistry*,Mar. 21, 1997, vol. 272(12), 7 pages.

Segelke B.W., et al., "Laboratory Scale Structural Genomics," *Journal of Structural and Functional Genomics*,2004, vol. 5(1-2), 11 pages.

Shih A.Y., et al., "Disassembly of Nanodiscs with Cholate",*Nano Letters*,Jun. 2007, vol. 7 (6), 5 pages.

Sonar S., et al., "A Redirected Proton Pathway in the Bacteriorhodopsin Mutan Tyr-57—Asp. Evidence for Proton Translocation Without Schiff Base Deprotonation," *The Journal of Biological Chemistry*,Nov. 1994, vol. 269 (46), 8 pages.

Sonar S., et al., "Cell-Free Synthesis, Functional Refolding and Spectroscopic Characterization of Bacteriorhodopsin, an Integral Membrane Protein," *Biochemistry*,Dec. 1993, vol. 32 (50), 5 pages.

Swaney J.B., "Properties of Lipid-apolipoprotein Association Products. Complexes of Human Apo AI and Binary Phospholipid Mixtures," *Journal of Biological Chemistry*,Sep. 1980, vol. 255, vol. 18, pp. 8798-8803.

Walter P., et al., "Preparation of Microsomal Membranes for Cotranslational Protein Translocation," *Methods in Enzymology*,1983, vol. 96, 10 pages.

Wang J., et al., "Comparison of the Dynamics of the Primary Events of Bacteriorhodopsin in Its Trimeric and Monomeric States," *Biophysical Journal*,Sep. 2002, vol. 83 (3), 10 pages.

(56) References Cited

OTHER PUBLICATIONS

Wetterau J.R., et al., "Effect of Dipalmitoylphosphatidylcholine Vesicle Curvature on the Reaction With Human Apolipoprotein A-I," *The Journal of Biological Chemistry*,Sep. 1982, vol. 257 (18), 7 pages.

Wientzek M., et al., "Binding of Insect Apolipophorin III to Dimyristoylphosphatidylcholine Vesicles. Evidence for a Conformational Change," *Journal of Biological Chemistry*,Feb. 1994, vol. 269 (6), 8 pages.

Wuu J.J., et al., "High Yield Cell-Free Production of Integral Membrane Proteins without Refolding or Detergents," *Biochimica et Biophysica Acta*,May 2008, vol. 1778 (5), 14 pages.

Anantharamaiah, G.M., et al., "Studies of Synthetic Peptide Analogs of the Amphipathic Helix / Structures of Complexes with Dimyristoyl Phosphatidycholine," 1985, The Journal of Biological Chemistry, vol. 260, No. 18, 10248-10255.

Baas B.J., et al., "Homotropic Cooperativity of Monomeric Cytochrome P450 3A4 in a Nanoscale Native Bilayer Environment," *Archives of Biochemistry and Biophysics*,Oct. 2004, vol. 430 (2), 11 pages.

Bayburt T.H., et al., "Single-Molecule Height Measurements on Microsomal Cytochrome P450 in Nanometer-Scale Phospholipid Bilayer Disks," Proceedings of the National Academy of Sciences of the United States of America, May 2002, vol. 99 (10), 6725-6730. 6 pages.

Bayburt T.H., et al., "Membrane Protein Assembly into Nanodiscs," *FEBS Letters*,May 2010, vol. 584 (9), 7 pages.

Chung, B.H., et al., "Studies of Synthetic Peptide Analogs of the Amphipathic Helix / Correlation of Structure with Function," 1985, The Journal of Biological Chemistry, vol. 260, No. 18, 10256-10262.

Civjan N., et al., "Direct Solubilization of Heterologously Expressed Membrane Proteins by Incorporation Into Nanoscale Lipid Bilayer," *Biotechniques*,Sep. 2003, vol. 35 (3), 6 pages.

Cruz F., et al., "Kinetic Properties of Recombinant MAO-A on Incorporation into Phospholipid Nanodisks," *Journal of Neural Transmission*,2007, vol. 114 (6), 4 pages.

Dawson P.E., et al., "Synthesis of Native Proteins by Chemical Ligation," *Annual Review of Biochemistry*,2000, vol. 69, 39 pages.

Imura, T., et al., "Minimum Amino Acid Residues of an a-Helical Peptide Leading to Lipid Nanodisc Formation," 2014, J. Oleo Sci. 63, (11) 1203-1208.

Imura, T., et al., "Surfactant-like Properties of an Amphilic a-Helical Peptide Leading to Lipid Nanodisc Formation," 2014, Langmuir, 20, 4752-4759.

"Individual" from Merriam-Webster, Jan. 13, 2015, accessed via WayBackMachine.com (2 pages).

International Preliminary Report on Patentability for Application No. PCT/US2015/051172 filed Sep. 9, 2016 on behalf of Lawrence Livermore National Security, LLC. dated Mar. 13, 2018. 8 pages. (English Only).

International Search Report for Application No. PCT/US2016/051172, dated Dec. 13, 2016., 6 pages.

Ishihara G., et al., "Expression of G Protein Coupled Receptors in a Cell-free Translational System Using Detergents and Thioredoxin-fusion Vectors," *Protein Expression and Purification*,May 2005, vol. 41 (1), 11 pages.

Jonas A., "Defined Apolipoprotein A-I Conformations in Reconstituted High Density Lipoprotein Discs," *The Journal of Biological Chemistry*,Mar. 1989, vol. 264 (9), 7 pages.

Jones M.K., et al., "Computer Programs to Identify and Classify Amphipathic alpha Helical Domains," *Journal of Lipid Research*,Feb. 1992, vol. 33 (2), 10 pages.

Klammt C., et al., "Cell-free Production of G Protein-coupled Receptors for Functional and Structural Studies," *Journal of Structural Biology*,Jul. 2007, vol. 158, 13 pages.

Lam K.S., et al., "Application of Combinatorial Library Methods in Cancer Research and Drug Discovery,"*Anti-cancer Drug Design*,Apr. 1997, vol. 12 (3), 24 pages.

"Microsome" from Wikipedia, Mar. 3, 2008, accessed via WayBackMachine.com (1 page).

Midtgaard, S.R., et al., "Self-assembling peptides form nanodiscs that stabilize membrane proteins," 2014, Soft Matter, 10, 738-752.

Nanodisc Trademark #78166119, Owner: Sligar, Stephen G., Retrieved from the Internet:[URL:inventively.com/search/trademarks/78166119], retrieved on Aug. 4, 2015, 2 pages.

Peters-Libeau C.A., et al., "Model of Biologically Active Apolipoprotein E Bound to Dipalmitoylphosphatidylcholine," *The Journal of Biological Chemistry*,Jan. 2006, vol. 281 (2), 8 pages.

Restriction Requirement for U.S. Appl. No. 15/744,754, filed Jan. 12, 2018 on behalf of Lawrence Livermore National Laboratory dated Aug. 7, 2019 9 pages.

Saito H. et al., "Contributions of domain structure and lipid interaction to the functionality of exchangeable human apolipoproteins" Elsevier, 2004. pp. 350-380.

Sawasaki T., et al., "A Bilayer Cell-Free Protein Synthesis System for High-Throughput Screening of Gene Products," *FEBS Letters*,Mar. 6, 2002, vol. 514(1), 4 pages.

Segota S., et al., "Spontaneous Formation of Vesicles," *Advances in Colloid and Interface Science*,Sep. 2006, vol. 121, pp. 51-75, 25 pages.

Shaw A.W., et al., "Phospholipid Phase Transitions in Homogeneous Nanometer Scale Bilayer Discs," *FEBS letters*, Jan. 2004, vol. 556 (1-3), 5 pages.

Sligar, S., "Overview of Nanodisc Technology" from Sligar Lab, accessed Nov. 21, 2014 (1 page).

Sligar webpage sligarlab.life.uiuc.edu/nanodisc.html, accessed Feb. 28, 2018. "Nanodisc Technology: Soluble Lipid Bilayer Systems for Structural and Functional Studies of Membrane Proteins" (3 pages).

Svetina S., et al., "Shape Behavior of Lipid Vesicles as the Basis of Some Cellular Processes," *The Anatomical Record*,Nov. 2002, vol. 268 (3), 11 pages.

Toniolo C. et al., "Lipopeptaibols, a novel family of membrane active, antimicrobial peptides" *Cellular and Molecular Life Sciences*, vol. 58,2001, pp. 1179-1188, 10 pages.

Tufteland M., et al., "Peptide Stabilized Amphotericin B Nanodisks," *Peptides*,Apr. 2007, vol. 28 (4), 6 pages.

"Vesicle" from Wikipedia, Dec. 16, 2008, accessed via WayBackMachine.com (5 pages).

Wallin E., et al., "Genome-Wide Analysis of Integral Membrane Proteins from Eubacterial, Archaean, and Eukaryotic Organisms," *Protein Science*,Apr. 1998, vol. 7 (4), 10 pages.

Written Opinion for Application No. PCT/US2015/051172, dated Dec. 13, 2016, 7 pages.

Adams, M.W.W., et al., "Hydrogenase," 1981, Biochimica et Biophysica Acta 594, 105-176.

Bayburt T.H., et al., "Self-Assembly of Single Integral Membrane Proteins into Soluble Nanoscale Phospholipid Bilayers," *Protein Science*, Nov. 2003, vol. 12 (11), 2476-2481. 6 pages, XP002498218, ISSN: 0961-8368.

Boldog T., et al., "Nanodiscs Separate Chemoreceptor Oligomeric States and Reveal Their Signalling Properties," *Proceedings of the National Academy of Sciences of the United States of America*, Aug. 2006, vol. 103 (31), 11509-11514. 6 pages.

Boldog T., et al., "Using Nanodiscs to Create Water-soluble Transmembrane Chemoreceptors Inserted in Lipid Bilayer," *Methods in Enzymology*, 2007, vol. 423, 317-335. 19 pages.

Burgdorf T., et al., "The Soluble NAD+-Reducing [NiFe]-Hydrogenase from Ralstonia eutropha H16 Consists of Six Subunits and can be Specifically Activated by NADPH," Journal of Bacteriology, May 2005, vol. 187 (9), 3122-3132. 11 pages.

Casey P.J., et al., "Protein Prenyltransferases," *Journal of Biological Chemistry*, Mar. 1996, vol. 271 (10), 5289-5292. 5 pages.

Chefson A., et al., "Progress Towards the Easier Use of P450 Enzymes," *Molecular Biosystems*, Oct. 2006, vol. 2 (10), 462-469. 8 pages.

Cornish K., et al., "Characterization of Cis-Prenyl Transferase Activity Localised in a Buoyant Fraction of Rubber Particles From Ficus Elastica Latex," *Plant Physiology and Biochemistry*, May/Jun. 1996, vol. 34 (3), 377-384. 10 pages.

Cornish K., et al., "Natural Rubber biosynthesis in Plants: Rubber Transferase," Methods in Enzymology, 2012, vol. 515, 63-82. 20 pages.

(56) References Cited

OTHER PUBLICATIONS

Cornish K., et al., "Rubber Biosynthesis in Plants," American Oil Chemist Society, *The Lipid Library*, Nov. 2011, 10 pages.

Das D., et al., "Role of Fe-hydrogenase in Biological Hydrogen Production," Current Science, Jun. 2006, vol. 90 (12), 1627-1637. 11 pages.

Denisov, I.G., et al., "Cytochromes P450 in Nanodiscs," Biochimica et Biophysica Act, 2010, 7 pages.

Donninger C., et al., "An Improved Synthesis of Isopentenyl Pyrophosphate," The Biochemical Journal, Nov. 1967, vol. 105 (2), 545-547. 3 pages.

Dubey R., et al., "Microencapsulation Technology and Applications," Defence Science Journal, Jan. 2009, vol. 59 (1), 82-95. 14 pages.

Elgren T. E. et al., "Immobilization of Active Hydrogenases by Encapsulation in Polymeric Porous Gels," *Nano Letters*, Oct. 2005, vol. 5 (10), 2085-2087. 3 pages.

Final Office Action for U.S. Appl. No. 12/352,472, dated Jun. 7, 2012, 25 pages.

Final Office Action for U.S. Appl. No. 12/352,472, dated Jun. 29, 2015, 18 pages.

Friedrich T. et al., "The respiratory complex I of bacteria, archaea and eukarya and its module common with membrane-bound multisubunit hydrogenases." FEBS Lett. Aug. 11, 2000;479(1-2):1-5.

Gan L., et al., "Role of NADPH-Cytochrome P450 Reductase and Cytochrome-b-5/NADH-b5 Reductase in Variability of CYP3A Activity in Human Liver Microsomes," *Drug Metabolism and Disposition*, Jan. 2009, vol. 37 (1), 90-96. 7 pages.

Gilbert L., "Insect Development: Morphognesis, molting and Metamorphosis," *Academic Press*, Sep. 18, 2009, 573-574. 2 pages.

Gorrod J.W., et al., "Some Observations on Type I and Type II Microsomal Binding Spectra," *Xenobiotica*, Jul.-Oct. 1971, vol. 1 (4), 521-522. 2 pages.

Greve, H-H., "Rubber, 2. Natural" in *Ullmann's Encyclopedia of Industrial Chemistry* vol. 31 (2012) 583-596. Wiley-VCH Verlag GmbH & Co. KGaA, Weinheim, 14 pages.

Grinkova, Y.V., et al., "Engineering extended membrane scaffold proteins for self-assembly of soluble nanoscale lipid bilayers," Protein Engineering, Design and Selection, 2010, vol. 23, No. 11, pp. 843-848.

Gronover C.S. et al., "Natural Rubber Biosynthesis and Physics-Chemical Studies on Plant Derived Latex," *Biotechnology of Biopolymers*, Jul. 2011, 75-88. 15 pages.

Hallenbeck P.C. et al., "Biological Hydrogen Production: Fundamentals and Limiting Processes," *International Journal of Hydrogen Energy*, Nov. 2002, vol. 27 (11-12), 1185-1193. 9 pages.

Hasemann C.A., et al., "Structure and Function of Cytochromes P450: a Comparative Analysis of Three Crystal Structures," *Structure*, Jan. 1995, vol. 3 (1), 22 pages.

Hiraishi T., et al., "Enzyme-catalyzed Synthesis and Degradation of Biopolymers," *Mini-Reviews in Organic Chemistry, Bentham Science Publishers*, Feb. 2009, vol. 6 (1), 11 pages.

Ho D., et al., "Fabrication of Biomolecule-copolymer Hybrid Nanovesicles as Energy Conversion Systems," *Nanotechnology*, Nov. 2005, vol. 16 (12), 13 pages.

Kurkin S., et al., "The Membrane-bound [NiFe]-hydrogenase (Ech) From Methanosarcina Barkeri: Unusual Properties of the Iron-sulphur Clusters," *European Journal of Biochemistry*, Dec. 2002, vol. 269 (24), 6101-6111. 11 pages.

Lechene C., et al., "High-resolution Quantitative Imaging of Mammalian and Bacterial Cells Using Stable Isotope Mass Spectrometry," *Journal of Biology*, 2006, vol. 5 (6), article 20, 30 pages.

Leitz A.J., et al., "Functional Reconstitution of Beta2-adrenergic Receptors Utilizing Self-assembling Nanodisc Technology," *Biotechniques*, May 2006, vol. 40 (5), 6 pages.

Long M., et al., "Characterization of a HoxEFUYH type of [NiFe] Hydrogenase from Allochromatium Vinosum and Some EPR and IR Properties of the Hydrogenase Module," *Journal of Biological Inorganic Chemistry*, Jan. 2007, vol. 12 (1), 18 pages.

Mcintosh C.L., et al., "The [NiFe]-Hydrogenase of the *Cyanobacterium synechocystis* sp. PCC 6803 Works Bidirectionally with a Bias to H2 Production," *Journal of the American Chemical Society*, Jun. 2011, vol. 133 (29), 12 pages.

Mcternan P.M., et al., "Intact Functional Fourteen-Subunit Respiratory Membrane-Bound [NiFe]-Hydrogenase Complex of the Hyperthermophilic Archaeon Pyrococcus Furiosus," *Journal of Biological Chemistry*, Jul. 2014, vol. 289 (28), 10 pages.

Meuer J., et al., "Purification and Catalytic Properties of Ech Hydrogenase From Methanosarcina Barkeri," *European Journal of Biochemistry*, Oct. 1999, vol. 265 (1), 11 pages.

Meyer J., "[Fe/Fe] Hydrogenases and Their Evolution: A Genomic Perspective," *Cellular and Molecular Life Sciences*, May 2007, vol. 64 (9), 1063-1084. 22 pages.

Non-Final Office Action for U.S. Appl. No. 12/352,472, dated Aug. 12, 2016, 31 pages.

Non-Final Office Action for U.S. Appl. No. 12/352,472, dated Dec. 26, 2014, 24 pages.

Non-Final Office Action for U.S. Appl. No. 12/352,472, dated Oct. 2, 2013, 19 pages.

Non-Final Office Action for U.S. Appl. No. 12/352,472, dated Sep. 22, 2011, 21 pages.

Notice of Allowance for U.S. Appl. No. 12/352,472, dated Mar. 17, 2017, 12 pages.

Ohya N., et al., "Biosynthesis of Natural Rubber and Other Natural Polyisoprenoids," Biopolymers Polyisoprenoids, Jan. 2005, 73-81. 9 pages.

Pan Z., et al., "The Major Protein of Guayule Rubber Particles is a Cytochrome P450: Characterization based on cDNA Cloning and Spectroscopic Analysis of the Solubilized Enzyme and Its Reaction Products," The Journal of Biological Chemistry, Apr. 1995, vol. 270 (15), 8487-8494. 8 pages.

Paterson-Jones J.C., et al., "The Biosynthesis of Natural Rubber," Journal of Plant Physiology, Jun. 1990, vol. 136 (3), 7 pages.

Persson B., et al., "Topology Prediction of Membrane Proteins," Protein Science, Feb. 1996, vol. 5 (2), 9 pages.

Ponciano G., et al., "Transcriptome and Gene Expression Analysis in Cold-Acclimated Guayule (*Parthenium argentum*) Rubber-Producing Tissue," Phytochemistry, Jul. 2012, vol. 79, 12 pages.

Rakhely G., et al., "Cyanobacterial-Type, Heteropentameric, NAD+-Reducing NiFe Hydrogenase in the Purple Sulfur Photosynthetic Bacterium Thiocapsa roseopersicina," Applied and Environmental Microbiology, Feb. 2004, vol. 70 (2), 7 pages.

Rapp V. et al., "Predicting Fuel Performance for Future HCCI Engines" Combust. Sci. Technol., 185: 735-748, Apr. 20, 2013. 15 pages.

Restriction Requirement for U.S. Appl. No. 12/352,472, dated May 27, 2011, 8 pages.

Sabatini, D.D., et al., "Mechanisms for the Incorporation of Proteins in Membranes and Organelles," Jan. 1, 1982, The Journal of Cell Biology, vol. 92, 1-22.

Sanderson K., "Chemistry: The Photon Trap," Nature, Mar. 27, 2008, vol. 452(7186), 3 pages.

Sapra R., et al., "A Simple Energy-Conserving System: Proton Reduction Coupled to Proton Translocation," Proceedings of the National Academy of Sciences of the United States of America, Jun. 24, 2003, vol. 100(13), 6 pages.

Sapra R., et al., "Purification and Characterization of a Membrane-Bound Hydrogenase from the Hyperthermophilic Archaeon Pyrococcus Furiosus," Journal of Bacteriology, Jun. 2000, vol. 182(12), 6 pages.

Schmidt T., et al., "Characterization of Rubber Particles and Rubber Chain Elongation in Taraxacum Koksaghyz," BMC Biochemistry, Feb. 19, 2010, vol. 11, 11 pages.

Schmitz O., et al., "HoxE—A Subunit Specific for the Pentameric Bidirectional Hydrogenase Complex (HoxEFUYH) of Cyanobacteria," Biochimica et Biophysica Acta, Apr. 22, 2002, vol. 1554(1-2), 9 pages.

Siler D.J., et al., "Composition of Rubber Particles of Hevea Brasiliensis, Parthenium Argentatum, Ficus Elastics and Euphorbia Lactiflua Indicates Unconventional Surface Structure," Plant Physiology and Biochemistry, Jan. 1997, vol. 35 (11), 9 pages.

(56) References Cited

OTHER PUBLICATIONS

Silvius J.R., "Thermotropic Phase Transitions of Pure Lipids in Model Membranes and their Modification by Membrane Proteins," Lipid-Protein Interactions, 1982, vol. 2, pp. 239-281, 43 pages.

Singer, S.J., et al., "The Fluid Mosaic Model of the Structure of Cell Membranes," Feb. 1972, Science, vol. 175, 720-731.

Singh A.P., et al., "The Micromorphology and Protein Characterization of Rubber Particles in Ficus Carica, Ficus Benghalensis and Hevea Brasiliensis," Journal of Experimental Botany, Mar. 2003, vol. 54 (384), 8 pages.

Smith D. et al., "Solubilisation of methane monooxygenase from Methylococcus capsulatus (Bath)" Eur. J. Biochem, 182, pp. 667-671, Jan. 17, 1989, 6 pages.

Soboh B., et al., "Purification and Catalytic Properties of a CO-Oxidizing: H2-Evolving Enzyme Complex from Carboxydothermus Hydrogenoformans," European Journal of Biochemistry, Nov. 2002, vol. 269 (22), 10 pages.

Stadermann F.J., et al., "Nanosims: The Next Generation Ion Probe for the Microanalysis of Extra Terrestrial Material," Meteoritics and Planetary Science, 36342, vol. 34 (4), 1999. 2 pages.

Stryer L., et al., "Oxygen Binds to a Heme Prosthetic Group: Biochemistry," 1995, 4th edition, 1 page.

Vincent K. A., et al., "Electrocatalytic Hydrogen Oxidation by an Enzyme at High Carbon Monoxide or Oxygen Levels," *Proceedings of the National Academy of Sciences*, Nov. 2005, vol. 102 (47), 4 pages.

Vincent K. A., et al., "Investigating and Exploiting the Electrocatalytic Properties of Hydrogenases," *Chemical Reviews*, 2007, vol. 107 (10), 48 pages.

Whalen M., et al., "Development of Crops to Produce Industrially Useful Natural Rubber," *Isoprenoid Synthesis in Plants and Microorganisms*, Jan. 2013, vol. 23, 17 pages.

White, S., Membrane Protein Insertion: The Biology-Physics Nexus, Apr. 16, 2007, J. Gen. Physiol., vol. 129, No. 5, 363-369.

Wikipedia—Bacteriorhodopsin, 2 pages, (Downloaded from the internet on Jun. 22, 2015).

Wikipedia., Hydrogenase retrieved from en.wikipedia.org/wiki/Hydrogenase on Nov. 6, 2012, 4 pages.

Woodward J., et al., "Enzymatic Production of Biohydrogen," *Nature*, Jun. 2000, vol. 405 (6790), 2 pages.

Woodward J., et al., "In Vitro Hydrogen Production by Glucose Dehydrogenase and Hydrogenase," *Nature Biotechnology*, Jul. 1996, vol. 14 (7), 3 pages.

Wu, L., et al., "Membrane targeting and translocation of bacterial hydrogenases," 2000, Arch Microbiology, 173:319-324.

Xie W., et al., "Initiation of Rubber Biosynthesis: In Vitro Comparisons of Benzophenone-Modified Diphosphate Analogues in Three Rubber-Producing Species," *Phytochemistry*, Oct. 2008, vol. 69 (14), 7 pages.

Zhang Y.H., et al., "High-Yield Hydrogen Production from Starch and Water by a Synthetic Enzymatic Pathway," *PLoS One*, May 2007, vol. 2 (5), e456, 6 pages.

Zhanhua C., et al., "Protein Subunit Interfaces: Heterodimers versus Homodimers," *Bioinformation*, Aug. 2005, vol. 1 (2), 12 pages.

Baughman, R.H. "Solid-state polymerization of diacetylenes," *Journal of Applied Physics*43(11), 4362-4370,(Nov. 1972), 10 pages.

Das A. et al., "Screening of Type I and II Drug Binding to Human Cytochrome P450-3A4 in Nanodiscs by Localized Surface Plasmon Resonance Spectroscopy." Analytical Chemistry, 2009. 81(10): p. 3754-3759.

Fischer, N.O., et al, "Colocalized Delivery of Adjuvant and Antigen Using Nanolipoprotein Particles Enhances the Immune Response to Recombinant Antigens." *Journal of the American Chemical Society*135(6), 2044-2047, (Jan. 2013). 4 pages.

Fischer N.O. et al., "Isolation, characterization, and stability of discretely-sized nanolipoprotein particles assembled with Apolipophorin-III" PLoS One, 2010, vol. 5, No. 7, e11643.

Frias, J.C., et al. "Properties of a Versatile Nanoparticle Platform Contrast Agent to Image and Characterize Atherosclerotic Plagues by Magnetic Resonance Imaging." *Nano Letters*6(10), 2220-2224, (Jul. 2006). 5 pages.

Georger, J.H., et al. "Helical and Tubular Microstructures Formed by Polymerizable Phosphatidylcholines." *Journal of American Chemical Society*109(20), 6169-6175, (Sep. 1987), 7 pages.

Hayward, J.A., et al. "Biomembrane surfaces as models for polymer design: the potential for haemocompatibility." *Biomaterials*5(3), 135-142, (May 1984). 8 pages.

Howland M.C. et al., "Model Studies of Membrane Disruption by Photogenerated Oxidative Assault." The Journal of Physical Chemistry, 2010. 114(19); p. 6377-6385.

International Preliminary Report on Patentability (Chapter 1) for International Application No. PCT/US2016/048632 filed on Aug. 25, 2016 on behalf of Lawrence Livermore National Laboratory dated Feb. 27, 2018 11 pages.

International Preliminary Report on Patentability (Chapter 1) for International Application No. PCT/US2017/020827 filed on Mar. 3, 2017 on behalf of Lawrence Livermore National Laboratory dated Sep. 11, 2018 9 pages.

International Search Report for International Application No. PCT/US2016/048632 filed on Aug. 25, 2016 on behalf of Lawrence Livermore National Laboratory dated Feb. 6, 2017 5 pages.

International Search Report for International Application No. PCT/US2017/020827 filed on Mar. 3, 2017 on behalf of Lawrence Livermore National Laboratory dated Jun. 20, 2017 4 pages.

Jia, J., et al, "Preparation, Characterizations, and In Vitro Metabolic Processes of Paclitaxel-Loaded Discoidal Recombinant High-Density Lipoproteins." *Journal of Pharmaceutical Sciences*101(8), 2900-2908, (Aug. 2012). 9 pages.

Johnston, D.S., et al. "Phospholipid Polymers—Synthesis and Spectral Characteristics," *Biochimica et Biophysica Acta*602(1), 57-69, (Oct. 1980). 13 pages.

Jonsson, M.P., et al. "Supported Lipid Bilayer Formation and Lipid-Membrane-Mediated Biorecognition Reactions Studied with a New Nanoplasmonic Sensor Template." *Nano Letters*7(11), 3462-3468, (Sep. 2007). 7 pages.

Kim, J-M., et al. "Immobilized Polydiacetylene Vesicles on Solid Substrates for Use as Chemosensors." *Advanced Materials*15(13), 1118-1121, (Jul. 2003). 4 pages.

Kreshech G.C. "Surfactants in Water—A Comprehensive Treatise." 1975: Plenum, New York.

Lamparski, H., et al. "Two-Dimensional Polymerization of Lipid Bilayers Degree of Polymerization of Sorbyl Lipids." *Macromolecules*28(6), 1786-1794, (Mar. 1995). 9 pages.

Lei, J., et al. "Two-Dimensional Polymerization of Lipid Bilayers: Rate of Polymerization of Acryloyl and Methacryloyl Lipids." *Macromolecules*27(6), 1381-1388, (Mar. 1994). 8 pages.

Lieser, G., et al. "Structure, Phase Transitions and Polymerizability of Multilayers of some Diacetylene Monocarboxylic Acids." Thin Solid Films 68(1), 77-90, (May 1980). 14 pages.

Mao H.B. et al., "Design and characterization of immobilized enzymes in microfluidic systems." Analytical Chemistry, 2002. 74(2): p. 379-385.

Morigaki, K., et al. "Surface Functionalization of a Polymeric Lipid Bilayer for Coupling a Model Biological Membrane with Molecules, Cells, and Microstructures." *Langmuir*29(8), 2722-2730, (Jan. 2013), 9 pages.

Ohno, H., et al. "Polymerization of Liposomes Composed of Diene-Containing Lipids by UV and Radical Initiators: Evidence for the Different Chemical Environment of Diene Groups on 1- and 2-Acyl Chains." *Macromolecules*20(5), 929-933, (May 1987). 5 pages.

Okahata Y. et al., "Polymerizable lipid-corked capsule membranes. Polymerization at different positions of corking lipid bilayers on the capsule and effect of polymerization on permeation behavior." *Journal of the American Chemical Society*,1988, vol. 110, No. 8, pp. 2495-2500.

Okazaki, T., et al. "Phase Separation of Lipid Microdomains Controlled by Polymerized Lipid Bilayer Matrices." *Langmuir*26(6), 4126-4129, (Dec. 2009). 4 pages.

(56) References Cited

OTHER PUBLICATIONS

Okazaki T. et al., "Polymerized lipid bilayers on a solid substrate: Morphologies and obstruction of lateral diffusion." Langmuir, 2009. 25(1): p. 345-351.
Pavlidou M. et al., "Nanodiscs Allow Phage Display Selection for Ligands to Non-Linear Epitopes on Membrane Proteins." PLoS One, 2013. 8(9).
Portet T. et al., "A new method for measuring edge tensions and stability of lipid bilayers: effect of membrane composition." Biophysical Journal, 2010. 99(10): p. 3264-3273.
Rabinovich, A.L., et al. "On the conformational, physical properties and functions of polyunsaturated acyl chains." Biochimica et Biophysica Acta 1085(1), 53-62, (Aug. 1991). 10 pages.
Rawicz W. et al., "Effect of Chain Length and Unsaturation on Elasticity of Lipid Bilayers," Biophysical Journal. 2000, 79(1): p. 328-339.
Regen, S.L., et al. "Polymerized Phophatidyl Choline Vesicles. Stabilized and Controllable Time-Release Carriers." Biochemical and Biophysical Research Cornmunications 101(1), 131-136, (Jul. 1981). 6 pages.
Restriction Requirement for U.S. Appl. No. 15/755,018, filed Feb. 23, 2018 on behalf of Lawrence Livermore National Laboratory, dated Oct. 2, 2019, 10 Pages.
Restriction Requirement for U.S. Appl. No. 16/082,924, filed Sep. 6, 2018 on behalf of Lawrence Livermore National Laboratory dated Oct. 24, 2019 9 pages.
Sadownik, A., et al. "Polymerized Liposomes Formed under Extremely Mild Conditions." Journal of American Chemical Society 108(24), 7789-7791, (Nov. 1986). 3 pages.
Sells, T.D., et al. "Two-Dimensional Polymerization of Lipid Bilayers: Degree of Polymerization of Acryloyl Lipids." Macromolecules 27(1), 226-233, (Jan. 1994). 8 pages.
Serrano, J., et al. "Polymerized Surfactant Vesicles. Determinations of Rates and Degrees of Polymerization in Vesicles Prepared from Styrene-Containing Surfactants." Macromolecules 18(10), 1999-2005, (Oct. 1985). 7 pages.
Sparks D.L. et al., "Effect of cholesterol on the charge and structure of apolipoprotein A-I in recombinant high density lipoprotein particles." Journal of Biological Chemistry, 1993. 268(31): p. 23250-7.
Tark S.H. et al., "Nanomechanical detection of cholera toxin using microcantilevers functionalized with ganglioside nanodiscs." Nanotechnology, 2010. 21(43).
Tsuchida, E., et al. "Polymerization of Unsaturated Phospholipids as Large Unilamellar Liposomes at Low Temperature." Macromolecules 25(1) 207-212, (Jan. 1992). 6 pages.
Written Opinion for International Application No. PCT/US2016/048632 filed on Aug. 25, 2016 on behalf of Lawrence Livermore National Laboratory dated Feb. 6, 2017 10 pages.
Written Opinion for International Application No. PCT/US2017/020827 filed on Mar. 3, 2017 on behalf of Lawrence Livermore National Laboratory dated Jun. 20, 2017 8 pages.
Yang T. et al., "Identification and cellular localization of human PFTAIRE1" Gene, 2001. 267(2): p. 165-172.
Yang T.L. et al., "Investigations of bivalent antibody binding on fluid-support phospholipid membranes: The effect of hapten density." Journal of the American Chemical Society, 2003. 125(16): p. 4779-4784.
Adamczyk J., et al., "The Isotope Array, A New Tool That Employs Substrate-Mediated Labeling of rRNA for Determination of Microbial Community Structure and Function," Applied and environmental microbiology, Nov. 2003, vol. 69 (11), 13 pages.
Addison S.L., et al., "Stable Isotope Probing: Technical Considerations When Resolving (15)N-labeled RNA in Gradients," Journal of Microbiological Methods, Jan. 2010, vol. 80(1), 6 pages.
Choquet C.G., et al., "Stability of Pressure-extruded Liposomes Made From Archaeobacterial Ether Lipids," Applied Microbiology and Biotechnology, Nov. 1994, vol. 42 (2-3), 10 pages.
Claypool et al., An ethanol/ether soluble apoprotein from rat lung surfactant augments liposome uptake by isolated granular pneumocytes. J Clin Invest. Sep. 1984; 74(3): 677-84. (Year: 1984). 8 pages.
Dengue Fever Climbs the Social Ladder, Special Report, Nature, Aug. 2007, vol. 448, 2 pages.
Final Office Action for U.S. Appl. No. 12/469,533, dated Dec. 4, 2012, 7 pages.
Final Office Action for U.S. Appl. No. 12/469,533, dated Oct. 24, 2011, 11 pages.
Final Office Action for U.S. Appl. No. 12/604,362, dated Dec. 4, 2012, 8 pages.
Hauger R.L., et al., "Corticotropin Releasing Factor (CRF) Receptor Signaling in the Central Nervous System: New Molecular Targets," CNS & Neurological Disorders Drug Targets, Aug. 2006, vol. 5 (4), 49 pages.
Hein C.D., et al., "Click Chemistry, A Powerful Tool for Pharmaceutical Sciences," Pharmaceutical Research, Oct. 2008, vol. 25 (10), 30 pages.
International Preliminary Report on Patentability for International Application No. PCT/US2018/030537 filed on May 1, 2018 on behalf of Lawrence Livermore National Security, dated Nov. 14, 2019. 11 pages.
Non-Final Office Action for U.S. Appl. No. 12/352,548, dated Sep. 13, 2011, 19 pages.
Non-Final Office Action for U.S. Appl. No. 12/469,533, dated May 23, 2012, 15 pages.
Non-Final Office Action for U.S. Appl. No. 12/604,362, dated May 7, 2012, 12 pages.
Non-Final Office Action for U.S. Appl. No. 14/536,513, dated Mar. 24, 2016, 19 pages.
Notice of Allowance for U.S. Appl. No. 12/352,548, dated Apr. 25, 2014, 9 pages.
Notice of Allowance for U.S. Appl. No. 12/352,548, dated Aug. 5, 2014, 8 pages.
Notice of Allowance for U.S. Appl. No. 12/352,548, dated Mar. 12, 2012, 10 pages.
Notice of Allowance for U.S. Appl. No. 12/469,533, dated Jul. 3, 2014, 13 pages.
Notice of Allowance for U.S. Appl. No. 12/604,362, dated Jul. 30, 2014, 13 pages.
Notice of Allowance for U.S. Appl. No. 14/536,513, dated Jul. 14, 2016, 5 pages.
Patel J.D., et al., "Preparation and Characterization of Nickel Nanoparticles for Binding to His-Tag Proteins and Antigens," Pharmaceutical Research, Feb. 2007, vol. 24 (2), 10 pages.
Restriction Requirement for U.S. Appl. No. 12/352,548, dated Apr. 25, 2011, 6 pages.
Restriction Requirement for U.S. Appl. No. 12/469,533, dated Jun. 7, 2011, 8 pages.
Restriction Requirement for U.S. Appl. No. 12/604,362, dated Jan. 11, 2012, 8 pages.
Rüger R., et al., "In Vitro Characterization of Binding and Stability of Single-Chain Fv Ni-NTA-Liposomes," Journal of Drug Targeting, Sep. 2006, vol. 14(8), 7 pages.
Schmitt L., et al., "Synthesis and Characterization of Chelator-Lipids for Reversible Immobilization of Engineered Proteins at Self-Assembled Lipid Interfaces," Journal of the American Chemical Society, 1994, vol. 116 (19), 7 pages.
Stryer., "Lipid Vesicles (Lipsomes) and Planar Bilayer Membranes are Valuable Model Systems," Biochemistry, 1995, 1 page.
Advisory Action for U.S. Appl. No. 12/118,530, dated Jun. 6, 2012, 5 pages.
Akkaladevi, N., et al., "Assembly of anthrax toxin pore: Lethal-factor complexes into lipid nanodiscs." Protein Science, 2013. 22(4): p. 492-501.
Allen, T.M. et al., "Drug delivery systems: entering the mainstream." Science, 2004. 303(5665): p. 1818-22.
Aranyi T., et al., "Predictable Difficulty or Difficulty to Predict," Protein Science, Jan. 2011, vol. 20 (1), 3 pages.
Bacher G., et al., "Negative and Positive Ion Matrix-Assisted Laser Desorption/Ionization Time-of-Flight Mass Spectrometry and Positive Ion Nano-Eiectrospray Ionization Quadrupole Ion Trap Mass

(56) References Cited

OTHER PUBLICATIONS

Spectrometry of Peptidoglycan Fragments Isolated from Various *Bacillus* Species," *Journal of Mass Spectrometry*, Feb. 2001, vol. 36 (2), 16 pages.

Bay et al., "Small multidrug resistance proteins: A multidrug transporter family that continues to grow," Biochimica et Biophysica Acta 1778 (2008) 1814-1838.

Baylon, J.L., et al., "Characterizing the membrane-bound state of cytochrome P450 3A4: structure, depth of insertion, and orientation." *Journal of the American Chemical Society*, 2013. 135(23):p. 8542-8551.

Beja O., et al., "Bacterial Rhodopsin: Evidence for a New Type of Phototrophy in the Sea," *Science*, Sep. 2000, vol. 289 (5486), 6 pages.

Bhattacharya, P., et al., "Nanodisc-Incorporated Hemagglutinin Provides Protective Immunity against Influenza Virus Infection." *Journal of Virology*,2010. 84(1): p. 361-371.

Bockaert J., et al., "Do Recombinant Receptor Assays Provide Affinity and Potency Estimates?" In *Receptor Classification: The Integration of Operational, Structural, and Transductional Information*,1997, vol. 812, New York, New York Academy of Sciences, 16 pages.

Bolikal, D. et al., "Degree of Polymerization of a Vesicle Membrane." *Macromolecules*, 1984. 17(6): p. 1287-1289.

Cappuccio, J.A., et al., "Cell-free expression for nanolipoprotein particles: building a high-throughput membrane protein solubility platform, in High throughput protein expression and purification." 2009, *Springer*. p. 273-295.

Cho, K., et al., "Therapeutic nanoparticles for drug delivery in cancer."*Clinical cancer research*, 2008. 14(5): p. 1310-1316.

Cuenca, AG et al, "Emerging implications of nanotechnology on cancer diagnostics and therapeutics." *Cancer*, 2006. 107: pp. 459-466. pp. 8.

Cullis P.R., et al., "Physical Properties and Functional Roles of Lipids in Membranes," *New Comprehensive Biochemistry*, 1991, vol. 20, 41 pages.

Ding, Y., et al., "A biomimetic nanovector-mediated targeted cholesterol-conjugated siRNA delivery for tumor gene therapy." *Biomaterials*, 2012. 33(34): p. 8893-8905.

Dong, C., et al., "Regulation of G protein-coupled receptor export trafficking," Biochimica et Biophysica Acta 1768 (2006) 853-870.

Final Office Action for U.S. Appl. No. 12/118,530, dated Jan. 25, 2012, 37 pages.

Final Office Action for U.S. Appl. No. 12/118,530, dated Mar. 6, 2015, 51 pages.

G Protein-coupled Receptor[online], Retrieved from the Internet: URL: Wikipedia 2008, web.archive.org/web/20080224232212/://en. wikipedia.org/wiki/G.protein-coupled.receptor, 2008, 7 pages.

International Preliminary Report on Patentability for Application No. PCT/US2008/063307, dated Nov. 10, 2009, 7 pages.

International Search Report for Application No. PCT/US2008/063307, dated Oct. 29, 2008, 5 pages.

International Search Report for International Application No. PCT/US2018/030648 filed on May 2, 2018 on behalf of Synthetic Genomics dated Aug. 30, 2018 4 pages.

"Ion channel", Wikipedia, accessed Dec. 22, 2014, pp. 1-8, 8 pages.

Justesen, B.H., et al., "Isolation of monodisperse nanodisc-reconstituted membrane proteins using free flow electrophoresis." *Analytical chemistry*, 2013. 85(7): p. 3497-3500.

Madani SY, et al., "A concise review of carbon nanotube's toxicology." Nano Rev., 2013. vol. 4, Issue 1.

Miyazaki, M., et al., "Effect of phospholipid composition on discoidal HDL formation." *Biochimica et Biophysica Acta (BBA)-Biomembranes*, 2013. 1828(5): p. 1340-1346.

Non-Final Office Action for U.S. Appl. No. 12/118,530, dated Aug. 30, 2011, 28 pages.

Non-Final Office Action for U.S. Appl. No. 12/118,530, dated Jul. 24, 2014, 33 pages.

North P., et al., "Alteration of Synaptic Membrane Cholesterol/Phospholipid Ratio Using a Lipid Transfer Protein, Effect on Gamma-aminobutyric Acid Uptake," *The Journal of Biological Chemistry*, Jan. 1983, vol. 258 (2), 12 pages.

Pasini E.M., et al., "In-Depth Analysis of the Membranes and Cytosolic Proteome of Red Blood Cells," Blood, Aug. 2006, vol. 180 (3), 12 pages.

Restriction Requirement for U.S. Appl. No. 12/118,530, filed May 9, 2008, dated Sep. 24, 2010, 14 pages.

Restriction Requirement for U.S. Appl. No. 12/118,530, dated Mar. 30, 2011, 28 pages.

Shih A.Y., et al., "Molecular Dynamics Simulations of Discoidal Bilayers Assembled from Truncated Human Lipoproteins," *Biophysical Journal*, Jan. 2005, vol. 88 (1), 9 pages.

Sparreboom, A., et al., "Comparative preclinical and clinical pharmacokinetics of a cremophor-free, nanoparticle albumin-bound paclitaxel (ABI-007) and paclitaxel formulated in Cremophor (Taxol)." *Clin Cancer Res*, 2005. 11(11): p. 4136-43.

Sun P.D., et al., "Overview of Protein Structural and Functional Folds," *Current Protocols in Protein Science*, May 2004, vol. 35, 3 pages.

Tieke, B. et al., "Polymerization of diacetylenes in multilayers." *Journal of Polymer Science: Polymer Chemistry Edition*,1979. 17(6): p. 1631-1644.

Tufteland, M. et al., "Nanodisks derived from amphotericin B lipid complex." *Journal of Pharmaceutical Sciences*, 2008. 97(10): p. 4425-4432.

Vickers, K.C., et al., "MicroRNAs are transported in plasma and delivered to recipient cells by high-density lipoproteins." *Nat Cell Biol*, 2011. 13(4): p. 423-33.

Wadsater, M., et al., "Monitoring shifts in the conformation equilibrium of the membrane protein cytochrome P450 reductase (FOR) in nanodiscs." *Journal of Biological Chemistry*, 2012. 287(41): p. 34596-34603.

Wang, J., et al., "Tumor targeting effects of a novel modified paclitaxel-loaded discoidal mimic high-density lipoproteins." *Drug delivery*, 2013. 20(8): p. 356-363.

Wang, S. et al., "The unsolved mystery of apoA-1 recycling in adipocyte."*Lipids Health Dis*, 2016. 15: p. 35.

Weilhammer, D.R., et al., "The use of nanolipoprotein particles to enhance the immunostimulatory properties of innate immune agonists against lethal influenza challenge." *Biomaterials*, 2013. 34(38): p. 10305-18.

Written Opinion for Application No. PCT/US2008/063307, dated Oct. 29, 2008, 6 pages.

Written Opinion for International Application No. PCT/US2018/030648 filed on May 2, 2018 on behalf of Synthetic Genomics dated Aug. 30, 2018 6 pages.

Yavlovich, A., et al., "A novel class of photo-triggerable liposomes containing DPPC:DC8,9PC as vehicles for delivery of doxorubcin to cells." *Biochimica Et Biophysica Acta-Biomembranes*, 2011. 1808(1): p. 117-126.

Yuan, Y., et al., "Delivery of hydrophilic drug doxorubicin hydrochloride-targeted liver using apoAl as carrier."*J Drug Target*, 2013. 21(4): p. 367-374.

Zidovska A. et al., "Block Liposome and Nanotube Formation is a General Phenomenon of Two-Component Membranes Containing Multivalent Lipids", Jan. 1, 2011, Soft Matter, vol. 7, No. 18, pp. 8363-8369.

Bacher G., et al., "Charge-reduced Nano Electrospray Ionization Combined with Differential Mobility Analysis of Peptides, Proteins, Glycoproteins, Noncovalent Protein Complexes and Viruses," Journal of Mass Spectrometry, Sep. 2001, vol. 36 (9), 1038-1052. 15 pages.

Baker S.E., et al., "Hydrogen Production by a Hyperthermophilic Membrane-Bound Hydrogenase in Water Soluble Nanolipoprotein Particles," Journal of the American Chemical Society, Nov. 18, 2008, vol. 131 (22), 15 pages.

Barros F., et al., "Modulation of Human erg K+ Channel Gating by Activation of a G Protein-Coupled Receptor and Protein Kinase C," The Journal of Physiology, Sep. 1998, vol. 511 (Pt 2), 333-346. 14 pages.

Bayburt T.H., et al., "Self-Assembly of Discoidal Phospholipid Bilayer Nanoparticles with Membrane Scaffold Proteins," Nano

(56) References Cited

OTHER PUBLICATIONS

Letters, 2002, vol. 2 (8), 853-856. 11 pages (Additional Pages of Accompanying Online Supplementary Information).
Behrens S., et al., "Linking Microbial Phylogeny to Metabolic Activity at the Single-cell Level by Using Enhanced Element Labeling-Catalyzed Reporter Deposition Fluorescence in Situ Hybridization (EL-FISH) and Nanosims," Applied and Environmental Microbiology, May 2008, vol. 74 (10), 3143-3150. 8 pages.
Berthelot K., et al., "Rubber Elongation Factor (REF), a Major Allergen Component in Hevea Brasiliensis Latex Has Amyloid Properties," PLoS One, 2012, vol. 7 (10), e48065. 12 pages.
Bijsterbosch M.K., et al., "Specific Targeting of a Lipophilic Prodrug of Iododeoxyuridine to Parenchymal Liver Cells Using Lactosylated Reconstituted High Density Lipoprotein Particles," Biochemical Pharmacology, Jul. 1996, vol. 52 (1), 113-121. 10 pages.
Bischler N., et al., "Specific Interaction and Two-Dimensional Crystallization of Histidine Tagged Yeast RNA Polymerase I on Nickel-Chelating Lipids," Biophysical Journal, Mar. 1998, vol. 74 (3), 1522-1532. 11 pages.
Borch J., et al., "Nanodiscs for Immobilization of Lipid Bilayers and Membrane Receptors: Kinetic Analysis of Cholera Toxin Binding to a Glycolipid Receptor," Analytical Chemistry, Aug. 2008, vol. 80 (16), 8 pages.
Boroske E., et al., "Osmotic Shrinkage of Giant Egg-Lecithin Vesicles," Biophysical Journal, Apr. 1981, vol. 34 (1), 95-109. 15 pages.
Boschker H.T.S., et al., "Direct Linking of Microbial Populations to Specific Biogeochemical Processes by 13C-Labelling of Biomarkers," Nature, Apr. 1998, vol. 392, 801-805. 5 pages.
Branden et al., "Introduction to Protein Structure," 2nd edition, Garland Science Publisher, 1999, pp. 3-12. 11 pages.
Brewer S.H., et al., "Formation of Thiolate and Phosphonate Adlayers on Indium-Tin Oxide: Optical and Electronic Characterization," Langmuir, 2002, vol. 18 (18), 6857-6865. 9 pages.
Brodie E.L., et al., "Application of a High-Density Oligonucleotide Microarray Approach to Study Bacterial Population Dynamics during Uranium Reduction and Reoxidation," Applied and Environmental Microbiology, Sep. 2006, vol. 72 (9), 6288-6298. 11 pages.
Brodie E.L., et al., "Profiling Microbial Identity and Activity: Novel Applications of NanoSIMS and High Density Microarrays," Systems Biology Research Strategy & Technology Development, Genomics: GTL Awardee Workshop VI, Department of Energy, 2008, 2 pages.
Brodie E.L., et al., "Urban Aerosols Harbor Diverse and Dynamic Bacterial Populations," Proceedings of the National Academy of Sciences of the United States of America, Jan. 2007, vol. 104 (1), 299-304. 6 pages.
Brodie et al., Systems Biology Research Strategy and Technology Development: Genomic and Proteomic Strategies. Publicly disclosed on Feb. 13, 2008, http://genomicscience.energy.gov/pubs/2008abstracts/2008GTLabstractstech.pdf, 48 pages.
Brown P.O., et al., "Exploring the New World of the Genome with DNA Microarrays," Nature Genetics, Jan. 1999, vol. 21 (1 Suppl), 33-37. 5 pages.
"Catalytic oxygen removal from coal mine methane," http://www.digitalrefining.com/article/1000623,Catalytic_oxygen_removal_from_coal_mine_methane.html# . . . , accessed Nov. 27, 2017, 4 pages.
Chaung H.C., et al., "CpG Oligodeoxynucleotides as DNA Adjuvants in Vertebrates and their Applications in Immunotherapy," International Immunopharmacology, Oct. 2006, vol. 6 (10), 1586-1596. 11 pages.
Chikh G.G., et al., "Attaching Histidine-Tagged Peptides and Proteins to Lipid-Based Carriers Through Use of Metal-Ion-Chelating Lipids," Biochimica et Biophysica Acta, Dec. 2002, vol. 1567 (1-2), 204-212. 9 pages.
Cline M.S., et al., "Integration of Biological Networks and Gene Expression Data Using Cytoscape," Nature Protocols, 2007, vol. 2 (10), 2366-2382. 17 pages.

Cornish K., "Biochemistry of Natural Rubber, a Vital Raw Material, Emphasizing Biosynthetic Rate, Molecular Weight and Compartmentalization, in Evolutionarily Divergent Plant Species," Natural Product Reports, Apr. 2001, vol. 18 (2), 182-189. 8 pages.
Co-Translation of Iintegral Membrane Proteins (MP) with Membrane Scaffoldproteins (MSP), also known as Nanodiscs[online], Jul. 2015 [ retrieved on Jul. 1, 2015]. Retrieved from the Internet: URL: http://technology.sbkb.org/portal/page/329/, 3 pages.
Cracknell J.A., et al., "Enzymatic Oxidation of H2 in Atmospheric O2: The Electrochemistry of Energy Generation from Trace H2 by Aerobic Microorganisms," Journal of the American Chemical Society, Jan. 2008, vol. 130 (2), 424-425. 2 pages.
Cravatt B.R., et al., "Large-Scale Profiling of Protein Palmitoylation in Mammalian Cells," Nature Methods, Feb. 2009, vol. 6 (2), 135-138. 4 pages.
Cube Biotech, "Assembly of Nanodiscs for use in Cell-Free Expression using MSP1D1 Protein and POPC Phospholipids," 2014, 3 pages.
Cube Biotech, "Nanodisc Assembly Kit MSP1E3D1_POPC," Dec. 2014, 3 pages.
Dalpke A.H., et al., "Phosphodiester CpG Oligonucleotides as Adjuvants:Polyguanosine Runs Enhance Cellular Uptake and Improve Immunostimulative Activity of Phosphodiester CpG Oligonucleotides in Vitro and in Vivo," Immunology, May 2002, vol. 106 (1), 102-112. 11 pages.
Das D., et al., "Hydrogen Production by Biological Processes: A Survey of Literature," International Journal of Hydrogen Energy, Jan. 2001, vol. 26 (1), 13-28. 16 pages.
Desantis T.Z., et al., "Greengenes, a Chimera-checked 16S rRna Gene Database and Workbench Compatible with ARB," Applied and Environmental Microbiology, Jul. 2006, vol. 72 (7), 5069-5072. 5 pages.
Desantis T.Z., et al., "High-Density Universal 16S rRNA Microarray Analysis Reveals Broader Diversity than Typical Clone Library When Sampling the Environment," Microbial Ecology, Apr. 2007, vol. 53 (3), 371-383. 13 pages.
Disalvo E.A., et al., "Surface Changes Induced by Osmotic Shrinkage on Large Unilamellar Vesicles," Chemistry and Physics of Lipids, Nov. 1996, vol. 84 (1), 35-45. 11 pages.
Duan H., et al., "Co-Incorporationof Heterologously Expressed *Arabidopsis* Cytochrome P450 and P450 Reductase into Soluble Nanoscale Lipid Bilayers," Archives of Biochemistry and Biophysics, Apr. 2004, vol. 424 (2), 141-153. 13 pages.
Dumartin B., et al., "Dopamine Tone Regulates D1 Receptor Trafficking and Delivery in Striatal Neurons in Dopamine Transporter-Deficient Mice," Proceedings of the National Academy of Sciences of the United States of America, Feb. 2000, vol. 97 (4), 1879-1884. 6 pages.
Eberly J.O., et al., "Thermotolerant Hydrogenases: Biological Diversity, Properties and Biotechnical Applications," Critical Reviews in Microbiology, Dec. 2008, vol. 34 (3-4), 117-130. 14 pages.
Final Office Action for U.S. Appl. No. 14/861,750, dated Feb. 23, 2018, 21 pages.
Fischer N.O., et al., "Conjugation to Nickel-Chelating Nanolipoprotein Particles Increases the Potency and Efficacy of Subunit Vaccines to Prevent West Nile Encephalitis," Bioconjugate Chemistry, Jun. 2010, vol. 21 (6), 1018-1022. 5 pages.
Fischer N.O., et al., "Evaluation of Nanolipoprotein Particles (NLPs) as an In Vivo Delivery Platform," PLOS ONE, Mar. 2014, vol. 9 (3), e93342, 1-17. 17 pages.
Fischer N.O., et al., "Immobilization of His-Tagged Proteins on Nickel-Chelating Nanolipoprotein Particles," Bioconjugate Chemistry, Mar. 2009, vol. 20 (3), 460-465. 6 pages.
Fitzgerald K.A., et al., "The Shape of Things to Come," Science, Jun. 2007, vol. 316 (5831), 1574-1576. 4 pages.
Gantz I., et al., "Molecular Cloning of a Gene Encoding the Histamine H2 Receptor," Proceedings of the National Academy of Sciences of the United States of America, Jan. 1991, vol. 88 (2), 429-433. 6 pages.
Gardner T.J., et al., "Systems for Orthogonal Self-assembly of Electroactive Monolayers on Au and ITO: an Approach to Molecular Electronics," Journal of American Chemical Society, Jul. 1995, vol. 117 (26), 6927-6933. 7 pages.

(56) References Cited

OTHER PUBLICATIONS

Giannini S.L., et al., "Enhanced Humoral and Memory B Cellular Immunity Using HPV16/18 L1 VLP Vaccine Formulated With the MPL/aluminium Salt Combination (AS04) Compared to Aluminium Salt Only," Vaccine, Aug. 2006, vol. 24 (33-34), 13 pages.
Goldet G., et al., "Hydrogen Production under Aerobic Conditions by Membrane-Bound Hydrogenases from Ralstonia Species," Journal of American Chemical Society, Jul. 2008, vol. 130 (33), 9 pages.
Guo H.H., et al., "Protein Tolerance to Random Amino Acid Change," Proceedings of the National Academy of Sciences of the United States of America, Jun. 2004, vol. 101 (25), 6 pages.
Gupta R.K ., et al., "Adjuvants for Human Vaccines—current Status, Problems and Future Prospects," Vaccine, Oct. 1995, vol. 13 (14), 14 pages.
Hamdy S., et al., "Pharmaceutical Analysis of Synthetic Lipid a-based Vaccine Adjuvants in Poly (D, L-lactic-co-glycolic Acid) Nanoparticle Formulations," Journal of Pharmaceutical and Biomedical Analysis, Aug. 2007, vol. 44 (4), 10 pages.
Hedderich R., "Energy-converting [NiFe] Hydrogenases From Archaea and Extremophiles: Ancestors of Complex I," Journal of Bioenergetics and Biomembranes, Feb. 2004, vol. 36 (1), 11 pages.
Hernandez-Caselles T., et al., "Influence of Liposome Charge and Composition on Their Interaction With Human Blood Serum Proteins," Molecular and Cellular Biochemistry, Mar. 1993, vol. 120 (2), 8 pages.
Hill M.A., et al., "Functional Analysis of Conserved Histidines in ADP-glucose Pyrophosphorylase From *Escherichia coli*," Biochemical and Biophysical Research Communications, Mar. 1998, vol. 244 (2), 5 pages.
Hong Y., et al., "G-protein-coupled Receptor Microarrays for Multiplexed Compound Screening," Journal of Biomolecular Screening, Jun. 2006, vol. 11 (4), 4 pages.
Huleatt J.W., et al., "Potent Immunogenicity and Efficacy of a Universal Influenza Vaccine Candidate Comprising a Recombinant Fusion Protein Linking Influenza M2e to the TLR5 Ligand Flagellin," Vaccine, Jan. 2008, vol. 26 (2), 14 pages.
International Preliminary Report on Patentability for Application No. PCT/US2009/044722, dated Nov. 23, 2010, 7 pages.
International Preliminary Report on Patentability for Application No. PCT/US2015/051516 filed Sep. 22, 2015 on behalf of Lawrence Livermore National Security, LLC. dated Mar. 28, 2017, 10 pages. (English Only).
International Search Report and Written Opinion for Application No. PCT/US2015/051516 filed on Sep. 22, 2015, dated Jan. 25, 2016, 12 pages.
International Search Report for Application No. PCT/US2009/044722, dated Oct. 28, 2010, 4 pages.
Jasanada F., et al., "Indium-111 Labeling of Low Density Lipoproteins With the DTPA-bis(Stearylamide): Evaluation as a Potential Radiopharmaceutical for Tumor Localization," Bioconjugate Chemistry, Jan.-Feb. 1996, vol. 7 (1), 10 pages.
Kapdan I.K., et al., "Bio-hydrogen Production from Waste Materials," Enzyme and Microbial Technology, Mar. 2006, vol. 38 (5), 14 pages.
Kolb H.C., et al., "The Growing Impact of Click Chemistryon Drug Discovery," Drug Discovery Today, Dec. 2003, vol. 8 (24), 10 pages.
Konishi E., et al., "Proper Maturation of the Japanese Encephalitis Virus Envelope Glycoprotein Requires Cosynthesis with the Premembrane Protein," Journal of Virology, Mar. 1993, vol. 67 (3), 4 pages.
Kostarelos K., et al., "Steric Stabilization of Phospholipid Vesicles by Block Copolymers Vesicle Flocculation and Osmotic Swelling Caused by Monovalent and Divalent Cations," Journal of the Chemical Society, Faraday Transactions, Aug. 1998, vol. 94, 10 pages.
Kovacs K., et al., "A Novel Approach for Biohydrogen Production," International Journal of Hydrogen Energy, Sep. 2006, vol. 31 (11), 9 pages.
Kubalek E.W., et al., "Two-dimensional Crystallization of Histidine-tagged, HIV-1 Reverse Transcriptase Promoted by a Novel Nickel-chelating Lipid," Journal of Structural Biology, Sep.-Oct. 1994, vol. 113 (2), 7 pages.
Langworthy, T.A., "Lipids of Thermoplasma," 1982, Methods in Enzymology, vol. 88, 396-406.
Lasic D.D., "Novel Applications of Liposomes," Trends in Biotechnology, Jul. 1998, vol. 16 (7), 15 pages.
Lazar E., et al., "Transforming Growth Factor Alpha: Mutation of Aspartic Acid 47 and Leucine 48 Results in Different Biological Activities," Molecular and Cellular Biology, Mar. 1988, vol. 8 (3), 6 pages.
Liang X., et al., "Mechanical Properties and Stability Measurement of Cholesterol-containing Liposome on Mica by Atomic Force Microscopy," Journal of Colloid and Interface Science, Oct. 2004, vol. 278 (1), 10 pages.
Lluis M.W., et al., "Protein Engineering Methods Applied to Membrane Protein Targets," Protein Engineering, Design & Selection, Feb. 2013, vol. 26 (2), 10 pages.
Lodish H., et al., "Section 17.5 Insertion of Membrane Proteins into the ER Membrane," Molecular Cell Biology, 4th edition, New York, NY., 2000, 9 pages.
Ludwig W., et al., "ARB: A Software Environment for Sequence Data," Nucleic Acids Research, Feb. 2004, vol. 32 (4), 9 pages.
Ma, K., et al., "Characterization of Hydrogenase II from the Hyperthermophilic Archaeon Pyrococcus furiosus and Assessment of Its Role in Sulfur Reduction," Apr. 2000, Journal of Bacteriology, vol. 182, No. 7, 1864-1871.
Manefield M., et al., "RNA Stable Isotope Probing, a Novel Means of Linking Microbial Community Function to Phylogeny," Applied and Environmental Microbiology, Nov. 2002, vol. 68 (11), 7 pages.
Marshall, G.R., et al., "Conformational effects of chiral a,a-dialkyl amino acids," 1988, Int. J. Peptide Protein Res., 32, 544-555.
Masquelier M., et al., "Low-density Lipoprotein as a Carrier of Antitumoral Drugs: in Vivo Fate of Drug-human Low-density Lipoprotein Complexes in Mice," Cancer Research, Aug. 1986, vol. 46 (8), 6 pages.
Mata-Haro V., et al., "The Vaccine Adjuvant Monophosphoryl Lipid A as a TRIF-Biased Agonist of TLR4," Science, Jun. 2007, vol. 316 (5831), 7 pages.
Mcgall G.H., et al., "The Efficiency of Light-Directed Synthesis of DNA Arrays on Glass Substrates," Journal of the American Chemical Society, Jun. 1997, vol. 119 (22), 10 pages.
Metz J., et al., "ACTH, α-MSH, and Control of Cortisol Release: Cloning, Sequencing, and Functional Expression of the Melanocortin-2 and Melanocortin-5 Receptor in Cyprinus Carpio," American Journal of Physiology Regulatory Integrative and Comparative Physiology, May 2005, vol. 289, 13 pages.
Moses S., et al., "Detection of DNA Hybridization on Indium Tin Oxide Surfaces," Sensors and Actuators B, Aug. 2007, vol. 125 (2), 7 pages.
Muscarinic Acetylcholine Receptor, Retrieved from the Internet: URL://web.archive.org/web/20071020193657//https://en.wikipedia.org/wiki/Muscarinic_acetylcholine_receptor, Wikipedia 2007, 6 pages.
Nanodisc Formation. LIAO Lab, Department of Cellbiology, Harvard Medical School, retrieved on Aug. 3, 2015, from the Internet: URL:https://liao.hms.harvard.edu/node/34, 2 pages.
Nanodisc. Kobo eBook Library, Retrieved from the Internet: URL: http://www.kobolibrary.com/articles/nanodisc, retrieved on Aug. 4, 2015, 4 pages.
Newpoint Gas "O2 Removal Services", https://www.newpointgas.com/services/oxygen-o2-removal/, 2017, 4 pages.
Non-Final Office Action for U.S. Appl. No. 14/199,973, dated May 6, 2015, 34 pages.
Non-Final Office Action for U.S. Appl. No. 14/861,750, dated Aug. 25, 2017, 23 pages.
Notice of Allowance for U.S. Appl. No. 14/199,973, dated Dec. 10, 2015, 11 pages.
Notice of Allowance for U.S. Appl. No. 14/861,750, filed Sep. 22, 2015 on behalf of Lawrence Livermore National Security, LLC. dated Jul. 24, 2018. 15 pages.

(56) References Cited

OTHER PUBLICATIONS

Okemoto K., et al., "A Potent Adjuvant Monophosphoryl Lipid a Triggers Various Immune Responses, but Not Secretion of IL-1beta or Activation of Caspase-1," The Journal of Immunology, Jan. 2006, vol. 176 (2), 6 pages.
Osada Y., et al., "Polymorphonuclear Leukocyte Activation by a Synthetic Muramyl Dipeptide Analog," Infection and Immunity, Dec. 1982, vol. 38 (3), 7 pages.
Ouverney C.C., et al., "Combined Microautoradiography-16S rRNA Probe Technique for Determination of Radioisotope Uptake by Specific Microbial Cell Types in Situ," Applied and Environmental Microbiology, Apr. 1999, vol. 65 (4), 8 pages.
Parkin A., et al., "The Difference a Se Makes? Oxygen-tolerant hydrogen production by the [NiFeSe]-hydrogenase from Desulfomicrobium baculatum," Journal of the American Chemical Society, Sep. 2008, vol. 130 (40), 13410-13416. 8 pages.
Persing D.H., et al., "Taking Toll: Lipid a Mimetics as Adjuvants and Immunomodulators," Trends in Microbiology, Oct. 2002, vol. 10 (10 Suppl), 6 pages.
Petrakova O., et al., "Noncytopathic Replication of Venezuelan Equine Encephalitis Virus and Eastern Equine Encephalitis Virus Replicons in Mammalian Cells," Journal of Virology, Jun. 2005, vol. 79 (12), 12 pages.
Pettibone D.J., et al., "The Effects of Deleting the Mouse Neurotensin Receptor NTR1 on Central and Peripheral Responses to Neurotensin," The Journal of Pharmacology and Experimental Therapeutics, Jan. 2002, vol. 300 (1), 9 pages.
Plumere, et al., "Enzyme-catalyzed O2 removal system for electrochemical analysis under ambient air: application in an amperometric nitrate biosensor (Abstract only)", Anal Chem. Mar. 6, 2012;84(5):2141-2146, Epub Feb. 10, 2012. 2 pages.
Protocols for Preparation of Nanodiscs, Mar. 2008, 7 pages.
Radajewski S., et al., "Identification of Active Methylotroph Populations in an Acidic Forest Soil by Stable Isotope Probing," Microbiology, Aug. 2002, vol. 148 (Pt 8), 12 pages.
Radajewski S., et al., "Stable-Isotope Probing as a Tool in Microbial Ecology," Nature, Feb. 2000, vol. 403 (6770), 4 pages.
Ratanabanangkoon P., et al., "Two-Dimensional Streptavidin Crystals on Giant Lipid Bilayer Vesicles," Langmuir, 2002, vol. 18 (11), 7 pages.
Ren X.R., et al., "Different G Protein-Coupled Receptor Kinases Govern G Protein and Beta-Arrestin-Mediated Signaling of V2 Vasopressin Receptor," Proceedings of the National Academy of Sciences of the United States of America, Feb. 1, 2005, vol. 102(5), 6 pages.
Rensen P.C., et al., "Recombinant Lipoproteins: Lipoprotein-like Lipid Particles for Drug Targeting," Advanced Drug Delivery Reviews, Apr. 25, 2001, vol. 47(2-3), 26 pages.
Restriction Requirement for U.S. Appl. No. 14/199,973, dated Dec. 8, 2014, 7 pages.
Restriction Requirement for U.S. Appl. No. 14/861,750, dated May 19, 2017, 7 pages.
Rüger R., et al., "Generation of Immunoliposomes using Recombinant Single-Chain Fv Fragments Bound to Ni-NTA-Liposomes," Journal of Drug Targeting, Aug. 2005, vol. 13(7), 8 pages.
Schena M., et al., "Quantitative Monitoring of Gene Expression Patterns With a Complementary DNA Microarray," Science, Oct. 1995, vol. 270 (5235), 4 pages.
Schnell D.J. et al., "Protein Translocons: Multifunctional Mediators of Protein Translocation across Membranes," Cell, Feb. 21, 2003, vol. 112(4), 15 pages.
Simon S.R., et al., "Chemical Modification of Hemoglobins: A Study of Conformation Restraint by Internal Bridging," Proceedings of the National Academy of Sciences of the United States of America, Aug. 1966, vol. 56 (2), 8 pages.
Singh-Gasson S., et al., "Maskless Fabrication of Light-directed Oligonucleotide Microarrays Using a Digital Micromirror Array," Nature Biotechnology, Oct. 1999, vol. 17 (10), 5 pages.

Soboh B., et al., "A Multisubunit Membrane-Bound [NiFe] Hydrogenase and an NADH-Dependent Fe-only Hydrogenase in the Fermenting Bacterium Thermoanaerobacter tengcongenis," Microbiology, 2004, vol. 150, 13 pages.
Sun X.L., et al., "Membrane-Mimetic Films of Asymmetric Phosphtidylcholine Lipid Bolaamphiphiles," Langmuir, Jan. 2006, vol. 22 (3), 8 pages.
Tercier-Waeber, et al., "Submersible Online Oxygen Removal System Coupled to an in Situ Voltammetric Probe for Trace Element Monitoring in Freshwater (Abstract only)", Environ. Sci. Technol., 2000, 34 (18), pp. 4018-4024, Publication Date (Web): Aug. 11, 2000. 4 pages.
Terpe K., et al., "Overview of Tag Protein Fusions: From Molecular and Biochemical Fundamentals to Commercial Systems," Applied Microbiology and Biotechnology, Jan. 2003, vol. 60 (5), 11 pages.
Ueda H., et al., "Induction of Tumor Necrosis Factor-Alpha in Solid Tumor Region by the Orally Administered Synthetic Muramyl Dipeptide Analogue, Romurtide," International Immunopharmacology, Jan. 2001, vol. 1 (1), 8 pages.
Uhlik O., et al., "DNA-Based Stable Isotope Probing: A Link between Community Structure and Function," Science of the Total Environment, Jun. 2009, vol. 407 (12), 9 pages.
Ulmer J,B., et al., "Vaccine Manufacturing: Challenges and Solutions," Nature Biotechnology, Nov. 2006, vol. 24 (11), 7 pages.
Unger R., et al., "The Genetic Algorithm Approach to Protein Structure Prediction," Structure and Bonding, Feb. 2004, vol. 110, 24 pages.
VICI (Valco Instruments Co. Inc.) "Oxygen Removal System", https://www.vici.com/instr/deox.php, 1-2, 2 pages, 2018.
Vignais P.M., et al., "Occurrence, Classification, and Biological Function of Hydrogenases: An Overview," Chemical Reviews, Oct. 2007, vol. 107 (10), 67 pages.
Vuorilehto K., et al., "Indirect Electrochemical Reduction of Nicotinamide Coenzymes," Bioelectrochemistry, Dec. 2004, vol. 65 (1), 7 pages.
Wacey A.I., et al., "Disentangling the Perturbational Effects of Amino Acid Substitutions in the DNA-binding Domain of p53," Human Genetics, Jan. 1999, vol. 104 (1), 8 pages.
Weeratna R.D., et al., "CpG DNA Induces Stronger Immune Responses with Less Toxicity than Other Adjuvants," Vaccine, Mar. 2000, vol. 18 (17), 8 pages.
White S.H., et al., "How Translocons Select Transmembrane Helices," Annual Review of Biophysics, 2008, vol. 37, 23-42. 20 pages.
Widman D.G., et al., "Construction and Characterization of a Second-Generation Pseudoinfectious West Nile Virus Vaccine Propagated Using a New Cultivation System," Vaccine, May 2008, vol. 26 (22), 10 pages.
Wikipedia, "5-HT Receptor," Wikipedia 2007, Retrieved from the Internet:[URL: http://web.archive.org/web/20071109235348/http://en.wikipedia.org/wiki/5-HT_receptor], 4 pages.
Wikipedia, Adrenergic Receptor, https://web.archive.org/web/20061230132111http//en.wikipedia.org/wiki/Adrenergic_Receptor, 2006, 4 pages.
Written Opinion for Application No. PCT/US2009/044722, dated Oct. 28, 2010., 8 pages.
Yoon J.C., et al., "Three-Dimensional Graphene Nano-Networks with High Quality and Mass Production Capability via Precursor-Assisted Chemical Vapor Deposition," Scientific Reports, 2013, vol. 1788, 8 pages.
Zhou, H., et al., Noncovalent Attachment of NAD+ Cofactor onto Carbon Nanotubes for Preparation of Integrated Dehydrogenase-Based Electrochemical Biosensors,: 2010, Langmuir Article, 26(8) 6028-6032.
Zimmermann S, et al., "Immunostimulatory DNA as Adjuvant: Efficacy of Phosphodiester CPG Oligonucleotides is Enhanced by 3' Sequence Modifications," Vaccine, Feb. 2003, vol. 21 (9-10), 6 pages.
De Filippis et al., "Enhanced Protein Thermostability by Ala—Aib Replacement," *Biochemistry* 1998, 37, 1686-1696. 11 Pages.
Final Office Action for U.S. Appl. No. 16/082,924 filed on Sep. 6, 2018 on behalf of Lawrence Livermore National Security, LLC. dated May 21, 2020. 50 Pages.

(56) References Cited

OTHER PUBLICATIONS

Non-Final Office Action for U.S. Appl. No. 15/755,018 filed on Feb. 23, 2018 on behalf of Lawrence Livermore National Laboratory. dated Apr. 22, 2020. 57 Pages.
Non-Final Office Action for U.S. Appl. No. 15/744,754 filed on Jan. 12, 2018 on behalf of Lawrence Livermore National Laboratory. dated Mar. 4, 2020. 53 Pages.
Non-Final Office Action for U.S. Appl. No. 16/082,924 filed on Sep. 6, 2018 on behalf of Lawrence Livermore National Security, LLC. dated Jan. 31, 2020 25 pages.
PDB database search for oxysterol binding protein, retrieved from the Internet: <://www.rcsb.org/pdb/results/results.do?tabtoshow=Current&qrid=37B93383>, retrieved on Feb. 20, 2020. 7 Pages.
Reinau M. et al. "The Diversity of FtsY-Lipid Interactions" *Biopolymers*, vol. 3, No. 7, Jan. 2010, pp. 595-606 12 pages.
Ruchala et al., "Oxpholipin 11D: An Anti-Inflammatory Peptide That Binds Cholesterol and Oxidized Phospholipids," PLoS One, Apr. 2010, vol. 5, Issue 4, e10181. 13 pages.
Alpha Helix — Wikipedia, the free encyclopedia, Nov. 7, 2014, 15 pages. //web.archive.org/web/20141107095336/https://en.wikipedia.org/wiki/Alpha_helix.
Amar M. et al., "A Novel Apolipoprotein C-II Mimetic Peptide That Activates Lipoprotein Lipase and Decreases Serum Triglycerides in Apolipoprotein E-Knockout Mice" *The Journal of Pharmacology and Experimental Therapeutics*, 352, pp. 227-235, Feb. 2015.
Cysteine—Wikipedia, the free encyclopedia, Sep. 20, 2015, 8 pages. //web.archive.org/web/20150920101331/https://en.wikipedia.org/wiki/Cysteine.
Donia M. et al., "Small Molecules from the Human Microbiota" Science, vol. 349, Jul. 24, 2015, pp. 1-25.
Final office Action for U.S. Appl. No. 15/755,018 filed Feb. 23, 2018 on behalf of Lawrence Livermore National Laboratory. dated Aug. 7, 2020. 14 Pages.
He Y. et al., "Apolipoprotein A1 Forms 5/5 and 5/4 Antiparallel Dimers in Human High-density Lipoprotein" *Molecular & Cellular Proteomics*, 18, pp. 854-864, Jul. 2019.
Li J. et al., "Synthesis of many different types of organic small molecules using one automated process" *Science Mag*, vol. 347 is. 6227, Mar. 13, 2015, pp. 1221-1226.
Small molecule—Wikipedia, the free encyclopedia, May 12, 2015, 4 pages. //web.archive.org/web/20150512235530/https://en.wikipedia.org/wiki/Small_molecule.
Small Molecules in Metabolomics: An Introduction. Retrieved from the web on Aug. 4, 2020. www.ebi.ac.uk/training-beta/online/courses/metabolomics-introduction/what-is/small-molecules/ 2 Pages.
Final Office Action for U.S. Appl. No. 15/744,754 filed Jan. 12, 2018, on behalf of Lawrence Livermore National Laboratory. dated Oct. 14, 2020. 21 Pages.
Gilmore S. F. et al., "Lipid composition dictates serum stability of reconstituted high-density lipoproteins: implications for in vivo applications" Royal Society of Chemistry, Nanoscale, Mar. 2018, 10, 7420-7430. 12 pages.
Gilmore S. F. et al., "Lipid cross-linking of nanolipoprotein particles substantially enhances serum stability and cellular uptake" Applied Materials and Interfaces, Jul. 2016, 8, 20549-20557. 9 pages.
Hafner, et al, "Development status and future prospects for a vaccine against Chlamydia trachomatis infection," Vaccine, 32, (2014), pp. 1563-1571. Published online: Aug. 22, 2013. 9 Pages.
Kuai R. et al., "Designer vaccine nanodiscs for personalized cancer immunotherapy" *Nature Materials*, Dec. 2016 10 pages. DOI:10.1038/NMAT4822.
Kuai R. et al., "Designer vaccine nanodiscs for personalized cancer immunotherapy (Supplementary Information)" *Nature Materials*, Dec. 2016 18 pages. DOI:10.1038/NMAT4822.
Liposome—Wikipedia, the free encyclopedia. dated Jul. 5, 2016, 7 pages, en.wikipedia.org/wiki/Liposome.
Micelle—Wikipedia, the free encyclopedia, dated Dec. 1, 2020, 7 pages //en.wikipedia.org/wiki/Micelle.

Nanodisc—Wikipedia, the free encyclopedia. dated Jul. 5, 2016, 3 pes, //en.wikipedia.org/wiki/Nanodisc.
Nanodisc Inc. Company Profile—ZoomInfo.com, dated May 25, 2015, 2 pages, www.zoominfo.com/c/nanodisc/65701329.
Non-Final Office Action for U.S. Appl. No. US 16/609,420 filed on Oct. 29, 2019 on behalf of Lawrence Livermore National Laboratory. dated Dec. 28, 2020. 53 pages.
Plotkin, et al., Vaccines, WB Saunders Company, p. 571. Year: 1988. 2 Pages.
Advisory Action for U.S. Appl. No. 15/744,754 filed Jan. 12, 2018 on behalf of Lawrence Livermore National Security, LLC dated Mar. 16, 2021. 13 pages.
Bloedon L.T. et al., "Safety, pharmacokinetics, and pharmacodynamics of oral apoA-I mimetic peptide D-4F in high-risk cardiovascular patients" Journal of Lipid Research, vol. 49, Mar. 2008, pp. 1344-1352.
Borhani D. W. et al., "Crystal structure of truncated human apolipoprotein A-I suggests a lipid-bound conformation" Proc. Natl. Acad. Sci. USA, vol. 94, Nov. 1997, pp. 12291-12296.
Elson E. L. "Fluorescence Correlation Spectroscopy: Past, Present, Future" Biophysical Journal, vol. 101, Dec. 2011, pp. 2855-2870.
Extended European Search Report for EP Application No. 17763807.9 filed Oct. 4, 2018 on behalf of Lawrence Livermore National Security LLC dated Oct. 30, 2019. 8 pages.
Leman L.J. et al., "Molecules that Mimic Apolipoprotein A-I: Potential Agents for Treating Atherosclerosis" J Med Chem, 57(6), Mar. 2014, 2169-2196. 56 pages.
Li L. et al., "Double Belt Structure of Discoidal High Density Lipoproteins: Molecular Basis for Size Heterogeneity" J. Mol. Biol, vol. 343, 2004, pp. 1293-1311.
Mendez A.J. "Synthetic Amphipathic Helical Peptides That Mimic Apolipoprotein A-I in Clearing Cellular Cholesterol "J Clin. Invest, vol. 94, Oct. 1994, pp. 1698-1705.
Popot J.L. "Alternatives to Detergents for Handling Membrane Proteins in Aqueous Solutions" Membrane Proteins in Aqueous Solutions, Jun. 2018, pp. 97-149. 134 pages.
Popovic K. et al., "Structure of saposin a lipoprotein discs" PNAS, vol. 109 No. 8, Feb. 2012, pp. 2908-2912.
Restriction Requirement for U.S. Appl. No. 16/159,189 filed Oct. 12, 2018 on behalf of Lawrence Livermore National Security, LLC. dated: Jan. 29, 2021. 6 Pages.
Segrest J. P. "Amphipathic Helix Motif: Classes and Properties" Proteins: Structure, Function, and Genetics, vol. 8, 1990, pp. 103-117.
Segrest J.P. et al., "Pathogenesis of atherosclerosis" *Current Opinion in Cardiology*, vol. 9, 1994, pp. 404-410.
Spuhler P. et al., "Binding of Apolipoprotein A-I Model Peptides to Lipid Bilayers" The Journal of Biological Chemistry, vol. 269 No. 39, Sep. 1994, pp. 23904-23910.
Swainsbury D.J.K. et al., "The effectiveness of styrene-maleic acid (SMA) copolymers for solubilisation of integral membrane proteins from SMA-accessible and SMA-resistant membranes" BBA-Biomembranes, 1859, Jul. 2017, pp. 2133-2143.
Troutt J.S. et al., "An apolipoprotein A-I mimetic dose-dependently increases the formation of preB1 HDL in human plasma" Journal of Lipid Research, vol. 49, Mar. 2008, pp. 581-587.
Watson C.E. et al., "Treatment of patients with cardiovascular disease with L-4F, an apo-A1 mimetic, did not improve select biomarkers of HDLK function" Journal of Lipid Research, vol. 52, Feb. 2011, pp. 361-373.
Wool G.D. "Apolipoprotein A-I mimetic peptide helix number and helix linker influence potentially anti-atherogenic properties" Journal of Lipid Research, vol. 49, 2008, pp. 1268-1283.
Zhao Y. et al., "Self-Assembling Cyclic D,L-a-Peptides as Modulators of Plasma HDL Function. A Supramolecular Approach toward Antiatherosclerotic Agents" ACS Central Science, vol. 3, Jun. 2017, pp. 639-646.

\* cited by examiner

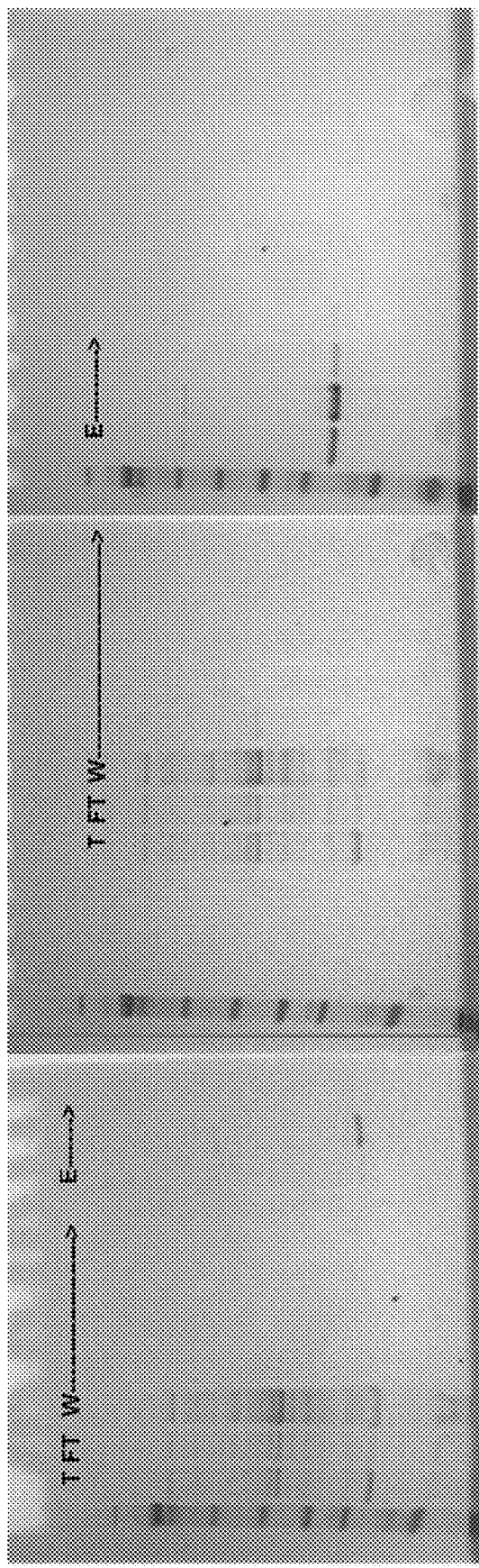
FIGURE 2A  NLP w/ DMPC
FIGURE 2B  Telo-

SEQUENCE LISTING

<160> NUMBER OF SEQ ID NOS: 4

<210> SEQ ID NO 1
<211> LENGTH: 897
<212> TYPE: DNA
<213> ORGANISM: Homo sapiens
<220> FEATURE:
<221> NAME/KEY: misc_feature
<223> OTHER INFORMATION: human apolipoprotein A-1 (APOA1, apoAI, apoA-I) preproprotein cDNA

<400> SEQUENCE: 1

```
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag gagatggagc tctaccgcca aggtggagcc gctgcgcgcg     480
cagagctcca gagggcgcgc cgccagaagc tgcacgagct gcaagagaag ctgagcccac     540
tgggcgagga gatgcgcgac cgcgcgcgcg cccatgtgga cgcgctgcgc acgcatctgg     600 cccccctacag cgacgagctg cgccagcgct tggccgcgcg ccttgaggct ctcaaggaga     660
acggcggcgc cagactggcc gagtaccacg ccaaggccac cgagcatctg agcacgctca     720
gcgagaaggc caagcccgcg ctcgaggacc tcgccaagg cctgctgccc gtgctggaga     780
gcttcaaggt cagcttcctg agcgctctcg aggagtacac taagaagctc aacacccagt     840
gaggcgcccg ccgccgcccc ccttcccggt gctcagaata aacgtttcca aagtggg        897
```

<210> SEQ ID NO 2
<211> LENGTH: 715
<212> TYPE: DNA
<213> ORGANISM: Artificial Sequence
<220> FEATURE:
<223> OTHER INFORMATION: synthetic truncated apolipoprotein A-1, truncated delta49 apolipoprotein A-1, truncated form of Apo A1 (delta49A1, delta1-49, delta49ApoA1, delta-ApoA1) cDNA

<400> SEQUENCE: 2

```
agcggcagag actatgtgtc ccagtttgaa ggctccgcct tgggaaaaca gctaaaccta      60
aagctccttg acaactggga cagcgtgacc tccaccttca gcaagctgcg cgaacagctc     120
ggccctgtga cccaggagtt ctgggataac ctggaaaagg agacagaggg cctgaggcag     180
gagatgagca aggatctgga ggaggtgaag gccaaggtgc agccctacct ggacgacttc     240
cagaagaagt ggcaggagga gatggagctc taccgccaga aggtggagcc gctgcgcgca     300
gagctccaag gggcgcgcg ccagaagctg cacgagctgc aagagaagct gagcccactg     360
ggcgaggaga tgcgcgaccg cgcgcgcgcc catgtggacg cgctgcgcac gcatctggcc     420
ccctacagcg acgagctgcg ccagcgcttg gccgcgcgcc ttgaggctct caaggagaac     480
ggcggcgcca gactggccga gtaccacgcc aaggccaccg agcatctgag cacgctcagc     540
gagaaggcca agcccgcgct cgaggacctc gccaaggcc tgctgcccgt gctggagagc     600
ttcaaggtca gcttcctgag cgctctcgag gagtacacta agaagctcaa cacccagtga     660
ggcgcccgcc gccgccccc ttcccggtgc tcagaataaa cgtttccaaa gtggg           715
```

<210> SEQ ID NO 3
<211> LENGTH: 267
<212> TYPE: PRT
<213> ORGANISM: Homo sapiens
<220> FEATURE:

-continued

```
<221> NAME/KEY: MISC_FEATURE
<223> OTHER INFORMATION: human apolipoprotein A-1 (APOA1, apoAI, apoA-I)
      preproprotein

<400> SEQUENCE: 3

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 4
<211> LENGTH: 219
<212> TYPE: PRT
<213> ORGANISM: Artificial Sequence
<220> FEATURE:
<223> OTHER INFORMATION: synthetic truncated human apolipoprotein A-1,
      truncated delta49, apolipoprotein A-1, truncated form of Apo A1
      (delta49A1, delta1-49, delta49ApoA1, delta-ApoA1)

<400> SEQUENCE: 4

Ser Gly Arg Asp Tyr Val Ser Gln Phe Glu Gly Ser Ala Leu Gly Lys
1               5                   10                  15

Gln Leu Asn Leu Lys Leu Leu Asp Asn Trp Asp Ser Val Thr Ser Thr
            20                  25                  30

Phe Ser Lys Leu Arg Glu Gln Leu Gly Pro Val Thr Gln Glu Phe Trp
        35                  40                  45

Asp Asn Leu Glu Lys Glu Thr Glu Gly Leu Arg Gln Glu Met Ser Lys
```

|   |   |   |   | 50 |   |   |   |   | 55 |   |   |   |   | 60 |   |   |   |   |   |
|---|---|---|---|---|---|---|---|---|---|---|---|---|---|---|---|---|---|---|---|

Asp Leu Glu Glu Val Lys Ala Lys Val Gln Pro Tyr Leu Asp Asp Phe
 65                  70                  75                  80

Gln Lys Lys Trp Gln Glu Met Glu Leu Tyr Arg Gln Lys Val Glu
              85                  90                  95

Pro Leu Arg Ala Glu Leu Gln Glu Gly Ala Arg Gln Lys Leu His Glu
             100                 105                 110

Leu Gln Glu Lys Leu Ser Pro Leu Gly Glu Glu Met Arg Asp Arg Ala
         115                 120                 125

Arg Ala His Val Asp Ala Leu Arg Thr His Leu Ala Pro Tyr Ser Asp
         130                 135                 140

Glu Leu Arg Gln Arg Leu Ala Ala Arg Leu Glu Ala Leu Lys Glu Asn
145                 150                 155                 160

Gly Gly Ala Arg Leu Ala Glu Tyr His Ala Lys Ala Thr Glu His Leu
             165                 170                 175

Ser Thr Leu Ser Glu Lys Ala Lys Pro Ala Leu Glu Asp Leu Arg Gln
         180                 185                 190

Gly Leu Leu Pro Val Leu Glu Ser Phe Lys Val Ser Phe Leu Ser Ala
         195                 200                 205

Leu Glu Glu Tyr Thr Lys Lys Leu Asn Thr Gln
210                 215

APOLIPOPROTEIN NANODISCS WITH TELODENDRIMER

CROSS-REFERENCES TO RELATED APPLICATIONS

This application is a continuation of, and claims priority to U.S. patent application Ser. No. 13/719,785, filed Dec. 19, 2012, and entitled "APOLIPOPROTEIN NANODISCS WITH TELLODENDRIMER," which in turn claims priority to U.S. Provisional Application No. 61/578,583, filed Dec. 21, 2011, and entitled "APOLIPOPROTEIN NANODISCS WITH TELLODENDRIMER," the content of each of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Grant No. R01CA115483, awarded by the National Institute of Health and Contract No. DE-AC52-07NA27344 between the United States Department of Energy and Lawrence Livermore National Security, LLC, for the operation of Lawrence Livermore National Laboratory.

BACKGROUND OF THE INVENTION

NLPs are discoidal nanoparticles formed when apolipoproteins and a population of phospholipids self-assemble into nanometer-sized discs containing a bilayer that is fully soluble in an aqueous environment. Nanolipoprotein particles (NLPs) are nanoscale (6-30 nm), discoidal patches of lipid bilayer stabilized by peripheral scaffold. NLPs present distinct advantages over currently used membrane systems in terms of particle size and consistency: the presence of the circular apolipoprotein "belt" that constrains the dimensions of the bilayer and helps ensure discrete NLP particle sizes between preparations compared to current model membranes. The protein belt also makes NLPs more thermally stable over time compared to micelles and liposomes. This bilayer is thought to closely mimic the cell membrane, providing a hydrophobic patch for the incorporation of membrane proteins as well as a region for the interaction of drugs and other small molecules.

Currently, the greatest use of NLPs has been the stabilization and characterization of membrane proteins. Noteworthy, is the fact that these artificial lipid systems were more soluble with less sample heterogeneity compared to proteins prepared from microsomes. The combined use of cell-free-NLPs production allows for the soluble presentation of membrane proteins in a highly controlled environment. Cell-free systems also permit unique labeling/tagging strategies not readily available to whole cell systems and allows one to go from a gene to protein to structure in a single day. Cell-free systems can accommodate additives that augment protein expression; including: chaperonins, lipids, redox factors, and detergents and protease inhibitors. More recently GPCRs and model proteins such as bacteriorhodopsin, have been reconstituted into NLPs using DMPC alone, POPC alone or a mixture of POPC/POPG demonstrating that lipid effects can be used to fine tune NLP applications. Other additives that alter lipid:apoprotein interactions could aid in solubilization and NLPs. Importantly, this can all be accomplished in a single reaction, in a high-throughput manner for testing a variety of conditions to identify optimal functional parameters.

The development of several amphiphilic PEG-dendritic block copolymers (telodendrimers) was previously shown to have several favorable nanoproperties for both cancer imaging and therapy using micelles. The particles were 20-80 nm. This size is generally smaller than many of the reported nanoparticles and liposomes, containing a well-defined and easily fine-tuned PEG corona. Importantly the use of PEG could minimize the nonspecific binding as well as biological degradation in vivo. Although the micelles were designed for packaging drug and imaging agents buried inside the hydrophobic core the telodendrimers themselves provide convenient covalent attachment sites that could be used for presenting active targeting and cellular uptake molecules on the surface. The possibility of incorporating the telodendrimer functionality on a different nanoplatform such as the NLPs could aid in the development of a novel multifaceted nanoparticle capable of carrying therapeutic peptides with imaging functions displayed on the surface of the nanoparticles. Surprisingly, the present invention meets this and other needs.

BRIEF SUMMARY OF THE INVENTION

In one aspect, the present invention provides a nanodisc including a membrane scaffold protein, a telodendrimer and a lipid.

In a second aspect, the present invention provides a cell-free method of making a nanodisc. The method includes forming a vesicle having a telodendrimer and a lipid, wherein the ratio of lipid to telodendrimer is from about 500:1 to about 1:1 (w/w). The method also includes forming a reaction mixture of the vesicle and a membrane scaffold protein in the absence of a cell, thereby preparing the nanodisc.

BRIEF DESCRIPTION OF THE DRAWINGS

FIG. 1A.) The chemical structure of a telodendrimer comprised of an octamer of cholic acid (CA8) linked to the terminal end of a linear 5 kDa PEG molecule (PEG$^{5K}$), which is solubilized with DMPC lipid. FIG. 1B.) The telodendrimer-lipid mixture is then added to a general cell free reaction, resulting in the self-assembly of Telo-NLPs.

FIGS. 2A-2B show telodendrimer addition increase the yield and solubility of nanoparticles. A total of 1 ml cell-free expression reactions were run with and without telodendrimer PEG$^{5K}$-CA$_8$ in DMPC. A typical comparison of the differing fractions produced throughout the purification is shown. The following symbols are T=total reaction, FT=flow through, W=wash and E=elution fractions. Elution fractions were centrifuged to remove non-soluble components. FIG. 2A shows a 4-12% SDS-PAGE gel for the purification profile of a NLP assembled with DMPC alone. FIG. 2B shows a 4-25% SDS-PAGE gel for the purification profile of a NLP assembled using DMPC and telodendrimer additives.

FIG. 3A, The size distribution of telodendrimer-NLPs measured by Dynamic Light Scattering. Telodendrimer-NLPs demonstrated an improved homogeneity compared to normal DMPC-NLP. FIG. 3B, Total aggregation of various telodendrimer-NLPs show significantly less aggregation compared to normal DMPC-NLP (p<0.01), FIG. 3C, PEG tail length and size of the telodendrimer-NLPs are significantly correlated (PEG$^{2K}$ vs PEG$^{5K}$, p<0.01).

FIG. 4A: NLP assembly using DMPC lipids alone. FIG. 4B: NLP assembly using DMPC lipids with 10% telodendrimer PEG$^{2K}$-CA$_4$. FIG. 4C: NLP assembly using DMPC lipids with 10% telodendrimer PEG$^{2K}$-CA$_8$. FIG. 4D: Magnification of NLP with 10% PEG$^{2K}$-CA$_8$ (arrowhead) from it's top view. Tubular structures (white arrow) represent Tobacco Mosaic Viruses for reference.

FIG. 6A). The pictures of the tubes were taken after the reactions were finished. FIG. 6B). Denaturing SDS PAGE gel electrophoresis of cell-free expressed proteins. All samples were loaded along with a molecular weight standard (M.W.). The pictures were taken with GE-TYPHOON 9410 using laser/filter 488 nm/520 nm. The non-specific bands below 20 kDa are free BODIPY-FL. The tubes and lanes are as follows: 1. Coexpression of BR and ApoA1 with DMPC (BR-NLP), 2. Cell free expression of ApoA1 with DMPC (empty NLP), 3. Coexpression of BR and ApoA1 with DMPC and 0.5% telodendrimer PEG$^{2k}$-CA$_4$, 4. Coexpression of BR and Apo1 with DMPC and 0.5% telodendrimer PEG$^{2k}$-CA$_8$. 5. Coexpression of BR and ApoA1 with DMPC and 0.5% telodendrimer PEG$^{5k}$-CF$_4$, 6. Coexpression of BR and ApoA1 with DMPC and 0.5% telodendrimer PEG$^{5k}$-CA$_8$.

DETAILED DESCRIPTION OF THE INVENTION

I. General

Figure 1A:
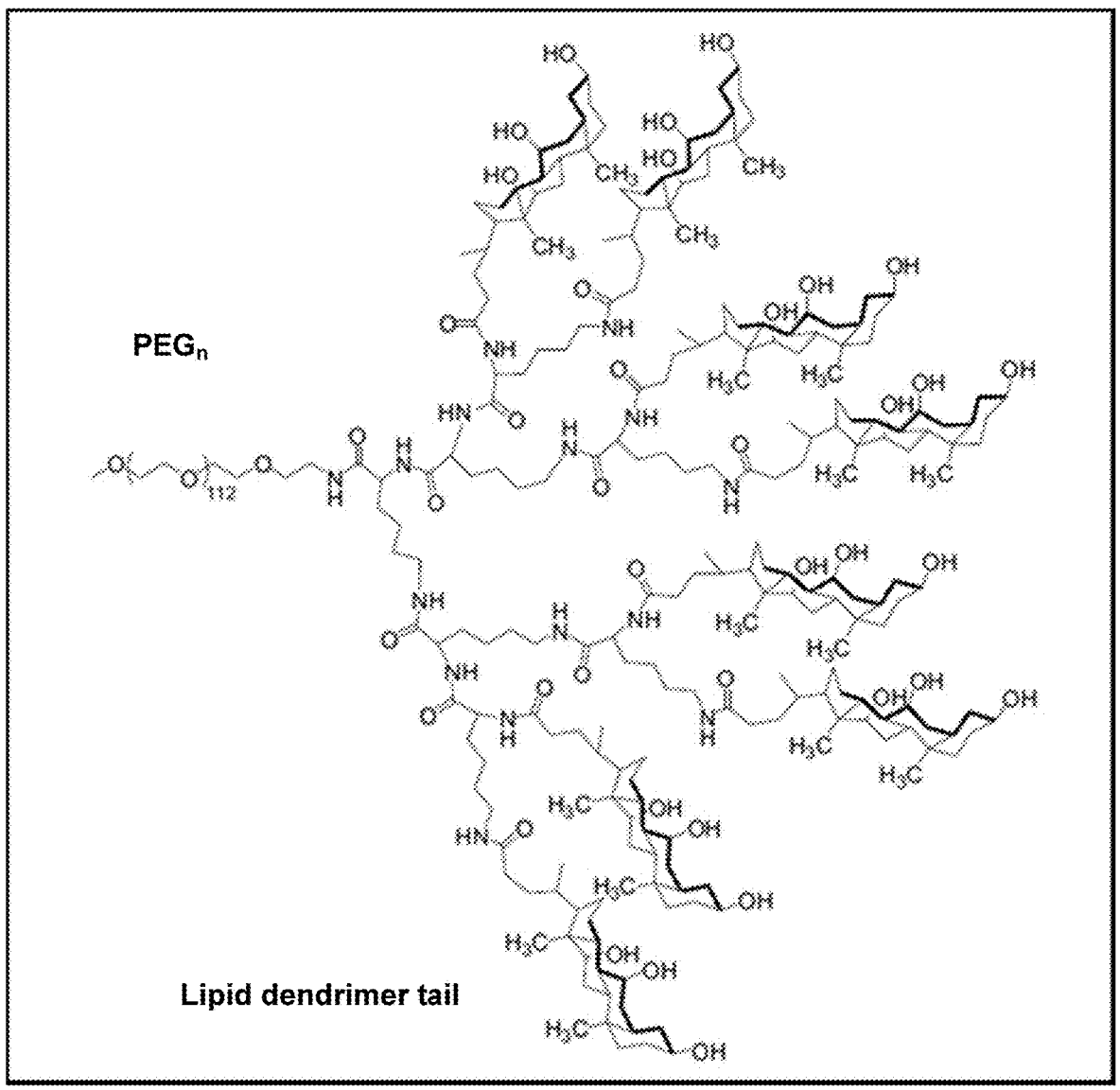
FIGS. 1A-1B show a schematic of cell-free synthesis of telodendrimer conjugated NLPs.

The present invention is based on the surprising discovery that amphiphilic polymer conjugates, called "telodendrimers," can bind and stabilize phospholipid bilayers to provide discrete nanostructures termed hybrid nanodiscs (hybrid-ND) in the presence of a membrane scaffold protein. The telodendrimers of the present invention are block copolymers having a linear polyethylene glycol) (PEG) segment and a dendritic hydrophobic segment or a dendritic amphiphilic segment. Telodendrimers can also have additional functional groups such as cholic acid groups and hydrophobic drugs covalently bound to the dendritic segment. The invention also provides convenient methods for nanodisc generation.

II. Definitions

As used herein, the term "nanodisc" refers to at least one phospholipid bilayer that is stabilized by a lipid-binding species and an apolipoprotein. The preferred lipid binding species is a telodendrimer as disclosed herein, although other lipid-binding species (including proteins and peptides) are known. The nanodiscs of the present invention are less than one micron in diameter. The nanodiscs can optionally contain additional lipid components, drugs, proteins that are not membrane scaffold proteins, diagnostic agents, and targeting agents.

As used herein, the term "membrane scaffold protein" refers to a protein that can stabilize a phospholipid bilayer in a nanodisc by binding to the bilayer periphery. In general, membrane scaffold proteins have hydrophobic faces that can associate with the nonpolar interior of a phospholipid bilayer and hydrophilic faces that favorably interact with a polar solvent such as an aqueous buffer. Membrane scaffold protein sequences may be naturally occurring, or may be engineered using recombinant techniques or constructed de nova. Naturally occurring membrane scaffold proteins include apolipoproteins, which are components of lipoproteins. Known classes of apolipoproteins include: A (including, for example, apo A-I and apo A-II), B, C, D, E, and H. The membrane scaffold proteins can be the full length protein, or a truncated version of the protein. Membrane scaffold protein is not intended to encompass various functional membrane proteins including, but not limited to, ion channels and other transmembrane receptors, porins, certain cell adhesion molecules, and electron transport proteins such as NADH dehydrogenase and ATP synthases.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at desired end groups using orthogonal protecting group strategies.

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendritic polymer can be attached to other segments of the telodendrimers, and the end groups may be further functionalized with additional chemical moieties.

As used herein, the terms "monomer" and "monomer unit" refer to repeating units that make up the dendrons of the dendritic polymers of the invention. The monomers may be AB2-type monomers, where A and B are two different functional groups capable of reacting together such that the resulting polymer chain has a branch point where an A-B bond is formed. Exemplary monomers include a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present invention include, but are not limited to, glyceric acid, 2,4-dihydroxybutyric acid, and 2,2-bis(hydroxymethyl)propionic acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional group. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as β-amino acids and other non-naturally occurring amino acids.

As used herein, the term "lipid" refers to lipid molecules that can include fats, waxes, steroids, cholesterol, fat-soluble vitamins, monoglycerides, diglycerides, triglycerides, phospholipids, sphingolipids, glycolipids, cationic or anionic lipids, derivatized lipids, and the like, as described in detail below. Lipids can form micelles, monolayers, and bilayer membranes. The lipids can self-assemble in combination with other components to form nanodiscs.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as polyethylene glycol) (PEG).

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives, and cholesterol formate.

As used herein, the term "cholic acid" refers to (R)-4-((3R,5S,7R,8R,9S,10S,12S,13R,14S,17R)-3,7,12-trihydroxy-10,13-dimethylhexadecahydro-1H-cyclopenta[α]phenanthren-17-yl)pentanoic acid. Cholic acid is also known as 3α,7α,12α-trihydroxy-5β-cholanoic acid; 3-α,7-α,12-α-Trihydroxy-5-β-cholan-24-oic acid; 17-β-(1-methyl-3-carboxypropyl)etiocholane-3α,7α,12α-triol; cholalic acid; and cholalin, Cholic acid derivatives and analogs, such as allocholic acid, pythocholic acid, avicholic acid, deoxycholic acid, and chenodeoxycholic acid are also useful in the present invention. Cholic acid derivatives can be designed to modulate the properties of the nanodiscs resulting from telodendrimer assembly, such as stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. Drugs useful in the present invention include, but are not limited to, paclitaxel, doxorubicin, etoposide, irinotecan, SN-38, cyclosporin A, podophyllotoxin, Carmustine, Amphotericin B, Ixabepilone, Patupilone (epothelone class), rapamycin and platinum drugs. The drugs of the present invention also include prodrug forms. One of skill in the art will appreciate that other drugs are useful in the present invention.

As used herein, "forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

As used herein, the term "solvent mixture" refers to a mixture of two or more solvents selected for suspension and/or dissolution of nanodisc components in a reaction mixture. The solvents in the mixture and the volume ratio in which they are combined depend primarily on the polarity of the lipids and telodendrimers in the reaction mixture. Non-limiting examples of solvents for use in the solvent mixture include chloroform, dichloromethane, ethanol, methanol, acetone, hexanes, petroleum ether, diethyl ether, dioxane, tetrahydrofuran, and water.

As used herein, the term "lysate" refers to the products produced after breaking down a cell.

As used herein, the term "buffer" refers to an aqueous solution capable of maintaining the pH of the solution at a nearly constant value. The buffer accomplishes this by including a weak acid and its conjugate base, such that the pH does not substantially change following addition of a small amount of acid or base. Representative buffering agents include citric acid, acetic acid, dipotassium phosphate ($K_2HPO_4^-$), N-cyclohexyl-2-aminoethanesulfonic acid (CHES), and borate. Buffers commonly used include, but are not limited to, TAPS, bicine, tris, tricine, TAPSO, HEPES, TES, MOPS, PIPES, cacodylate, SSC, MES and succinic acid.

As used herein, the term "polymerase" refers to an enzyme capable of synthesizing nucleic acid polymers. The polymerase can be a DNA or an RNA polymerase. Representative polymerases include DNA polymerase I, DNA polymerase II, DNA polymerase III holoenzyme, DNA polymerase IV, RNA polymerase I, RNA polymerase II, RNA polymerase III and T7 RNA polymerase. Other polymerases are useful in the present invention.

III. Telodendrimers

Telodendrimers useful in the present invention include any telodendrimer having a polyethyleneglycol (PEG) polymer linked to a dendrimer functionalized with a hydrophobic group, a hydrophilic group, an amphiphilic compound or a drug on the dendrimer periphery. In some embodiments, the invention provides a compound of formula I:

$$\text{PEG-D-(R)}n \quad \text{(I)}$$

wherein radical D of formula I is a dendritic polymer having a single focal point group, a plurality of branched monomer units X and a plurality of end groups. PEG of formula I is a polyethyleneglycol (PEG) polymer, wherein each PEG polymer has a molecular weight of 1-100 kDa. Each R of formula I is independently the end group of the dendritic polymer or an amphiphilic compound, such that when R is not an end group each R is linked to one of the end groups. Subscript n of formula I is an integer from 2 to 20, wherein subscript n is equal to the number of end groups on the dendritic polymer, and wherein at least half the number n of R groups are each an amphiphilic compound.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxyl amino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid or 5-amino-2-(3-aminopropyl) pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine. In some embodiments, the dendritic polymer can be a poly(lysine) dendritic polymer wherein each end group can be hydroxy.

The focal point of a telodendrimer or a telodendrimer segment may be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group can also be an electrophile such as an aldehyde, a carboxylic acid, or a carboxylic acid derivative including an acid chloride or an N-hydroxysuccinimidyl ester.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. In some embodiment, n is 2-20.

The R groups installed at the telodendrimer periphery can be any suitable chemical moiety, including hydrophilic groups, hydrophobic groups, or amphiphilic compounds. Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R, 5S,7R,8R,9S,10S,12S,13R,17R)-3,7,12-trihydroxy-10,13-dimethylhexadecahydro-1H-cyclopenta[α]phenanthren-17-yl)pentanoic acid, having the structure:

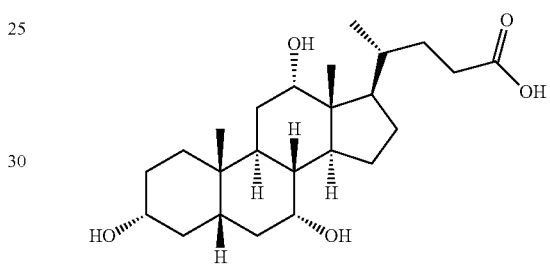

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

In some embodiments, each R can be cholic acid, (3α,5β,7α,12α)-7,12-dihydroxy-3-(2,3-dihydroxy-1-propoxy)-cholic acid, (3α,5β,7α,12α)-7-hydroxy-3,12-di(2,3-dihydroxy-1-acid, (3α,5β,7α,12α)-7,12-dihydroxy-3-(3-amino-2-hydroxy-1-propoxy)-cholic acid, cholesterol formate (CF), doxorubicin, or rhein. In some embodiments, each amphiphilic compound is cholic acid (CA). In some embodiments, each amphiphilic compound is cholesterol formate (CF).

Telodendrimer end groups can also include drugs such as paclitaxel, doxorubicin, etoposide, irinotecan, SN-38, cyclosporin A, podophyllotoxin, carmustine, amphotericin, ixabepilone, patupilone (epothelone class), rapamycin and platinum drugs. One of skill in the art will appreciate that other drugs are useful in the present invention.

The telodendrimer can have a single type of R group on the periphery, or any combination of R groups in any suitable ratio. In general, at least half the number n of R groups are other than an end group. For example, at least half the number n of R groups can be a hydrophobic group, a hydrophilic group, an amphiphilic compound, a drug, or any combination thereof. In some embodiments, half the number n of R groups are amphiphilic compounds.

In some embodiments, all the R groups are an amphiphilic group such as cholic acid or cholesterol formate. In other embodiments, some of the R groups are an end group of the dendrimer. In some other embodiments, at least two different R groups are present, such as two different amphiphilic groups, or an amphiphilic group and a drug, or an amphiphilic group and a dendritic polymer end group, or two different drugs, or a drug and a dendritic end group.

Telodendrimers useful in the present invention include, but are not limited to, $PEG^{2K}$-D-$CA_4$, $PEG^{5K}$-D-$CA_4$, $PEG^{10K}$-D-$CA_4$, $PEG^{2K}$-D-$CA_8$, $PEG^{5K}$-D-$CA_8$, $PEG^{10K}$-D-$CA_8$, $PEG^{2K}$-D-$CF_4$, $PEG^{5K}$-D-$CF_4$, $PEG^{10K}$-D-$CF_4$, $PEG^{2K}$-D-$CF_8$, $PEG^{5K}$-D-$CF_8$, or $PEG^{10K}$-D-$CF_8$, wherein each dendritic polymer D is a poly(lysine) dendritic polymer wherein each end group is hydroxy. In some embodiments, the telodendrimer can be $PEG^{2K}$-D-$CA_4$, $PEG^{2K}$-D-$CA_8$, $PEC^{5K}$-D-$CA_8$, $PEG^{5K}$-D-$CF_4$, $PEG^{10K}$-D-$CF_4$, or $PEG^{5K}$-D-$CF_8$. In some embodiments, the telodendrimer can be $PEG^{5K}$-D-$CA_8$, $PEG^{5K}$-D-$CA_4$ or $PEG^{2K}$-D-$CA_4$.

In some embodiments, the telodendrimer can have any of the following formulas:

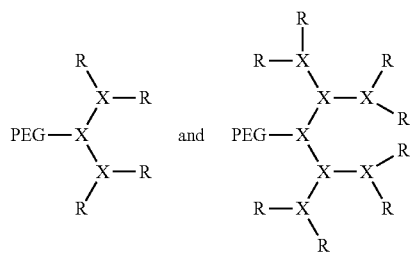

wherein each monomer unit X is lysine.

The telodendrimers useful in the present invention are known and can be prepared by a variety of methods, such as those described in PCT Publication No. WO 2010/039496.

IV. Nanodiscs

As described above, apolipoprotein-containing nanodisc drug formulations have shown in vitro and in vivo activity, but demonstrate limited stability and suffer from the drawbacks associated with the use of recombinant proteins. Telodendrimers offer several advantages when used in combination with recombinant apolipoprotein and incorporated into the lipid nanodisc formulations. Telodendrimers are synthetic polymers and easy to scale up. The telodendrimer components (namely PEG and biomolecules including lysine and cholic acid), the telodendrimers, and the telodendrimer-containing nanodiscs are fully biocompatible. The telodendrimer PEG component, presented on the nanodisc surface, reduces particle aggregation due to stacking of the lipid nanodisc. PEGylation can also prevent the rapid clearance of nanodiscs by the reticuloendothelial system, thus providing a sustained delivery of drug to a target site. In addition, the multifunctional telodendrimers allow for the introduction of targeting molecules for specific delivery of drugs to targeted cells, tissues, tumors, or microorganisms. Furthermore, the size and drug loading capacity of the hybrid-ND can easily be tuned by varying the configuration of the telodendrimers, the use of different telodendrimer-lipid combinations or adjusting the ratio of lipid-to-telodendrimer in the final pharmaceutical formulation.

In one aspect, the present invention provides a nanodisc with a membrane scaffold protein. The nanodisc includes a membrane scaffold protein, a telodendrimer and a lipid.

Any suitable membrane scaffold protein can be used in the nanodiscs of the present invention. Representative membrane scaffold proteins include, but are not limited to, apolipoproteins A (including, for example, apo A-1 and apo A-2), B, C, D, E, and H. In some embodiments, the membrane scaffold protein can be apolipoprotein. In some embodiments, the membrane scaffold protein can be apolipoprotein A-1. The membrane scaffold protein can be the full length protein, or a truncated version of the full length portion. In some embodiments, the membrane scaffold protein can be the truncated apolipoprotein A-1 (Δ49A1).

The telodendrimers that are useful in the present invention are described above and are amphiphilic conjugates having a hydrophilic PEG segment and an amphiphilic or hydrophobic segment. The amphiphilic segment of the telodendrimer can contain cholic acid, or other suitable amphiphilic moiety, which has a hydrophobic face and a hydrophilic face. The cholic acid and the PEG are connected by dendritic polymers that can contain a variety of acid repeats units. Typically, the dendritic polymers include a diamino carboxylic acid such as lysine.

The nanodiscs of the present invention can contain any suitable lipid, including cationic lipids, zwitterionic lipids, neutral lipids, or anionic lipids. Suitable lipids can include fats, waxes, steroids, cholesterol, fat-soluble vitamins, monoglycerides, diglycerides, phospholipids, sphingolipids, glycolipids, cationic or anionic lipids, derivatized lipids, and the like. In some embodiments, the nanodisc contains a lipid selected from a phospholipid, a lysolipid, cholesterol, a phosphatidylcholine, a phosphatidylethanolamine, a phosphatidylglycerol, a phosphatidylserine, a phosphatidylinositol and a PEGylated lipid.

Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (PI), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPC), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. Phospholipids can be lysolipids, which contain only one fatty acid moiety bonded to the glycerol subunit via an ester linkage. Lipid extracts, such as egg PC, heart extract, brain extract, liver extract, and soy PC, are also useful in the present invention. The lipids can include derivatized lipids, such as PEGylated lipids. Derivatized lipids can include, for example, DSPE-PEG2000, cholesterol-PEG2000, DSPE-polyglycerol, or other derivatives generally known in the art.

Nanodiscs of the present invention can contain steroids, characterized by the presence of a fused, tetracyclic nonane ring system. Examples of steroids include, but are not limited to, cholesterol, cholic acid, progesterone, cortisone, aldosterone, estradiol, testosterone, and dehydroepiandrosterone. Synthetic steroids and derivatives thereof are also contemplated for use in the present invention.

The nanodiscs can contain cationic lipids, which contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3β-[N—(N',N'-dimethylaminoethane)carbamoyl]cholesterol (DC-Chol), dimethyldioctadecylammonium (DDAB) and N,N-dimethyl-2,3-dioleyloxy)propylamine (DODMA).

In some embodiments, the nanodisc of the present invention includes a lipid selected from 1,2-dipalmitoyl-sn-glycero-3-phosphocholine (DPPC), 1,2-ditetradecanoyl-sn-glycero-3-phosphocholine (DMPC), 1-tetradecanoyl-2-hexadecanoyl-sn-glycero-3-phosphocholine (MPPC), 1,2-dioctadecanoyl-sn-glycero-3-phosphocholine (DSPC), 1,2-distearoyl-sn-glycero-3-phosphoethanolamine (DSPE), 1,2-dihexadecanoyl-sn-glycero-3-phosphoethanolamine (DPPE), 1,2-distearoyl-sn-glycero-3-phospho-(1'-rac-glycerol) (DSPG), 1,2-dipalmitoyl-sn-glycero-3-phospho-(1'-rac-glycerol) (DPPG), 1-tetradecanoyl-2-hexadecanoyl-sn-glycero-3-phosphoglycerol (MPPG) and cholesterol. In some embodiments, the nanodisc contains a lipid of DMPC.

Any suitable combination of lipids can be used to provide the nanodiscs of the invention. The lipid compositions can be tailored to affect characteristics such as leakage rates, stability, particle size, zeta potential, protein binding, in vivo circulation, and/or accumulation in tissues or organs. For example, negative or positive lipids, such as DSPG and/or DOTAP, can be included to affect the surface charge of a nanodisc. The lipid compositions can include about ten or fewer types of lipids, or about five or fewer types of lipids, or about three or fewer types of lipids. In some embodiments, the lipid includes at least two different lipids. The molar percentage (mol %) of a specific type of lipid present can be from about 0% to about 10%, from about 10% to about 30%, from about 30% to about 50%, from about 50% to about 70%, from about 70% to about 90%, or from about 90% to 100% of the total lipid present in a nanodisc.

The nanodiscs of the invention may contain any suitable combination of lipids with telodendrimers and/or other components. The ratio of lipid to telodendrimer in the nanodisc, for example, can be from about 500:1 to about 1:1 (w/w). For example, the ratio can be about 500:1, 400:1, 300:1, 200:1, 100:1, 99:1, 95:1, 90:1, 80:1, 75:1, 70:1, 60:1, 50:1, 40:1, 30:1, 25:1, 20:1, 15:1, 14:1, 13:1, 12:1, 10:1, 9:1, 8:1, 7:1, 6:1, 5:1, 4:1, 3:1, 2:1 or 1:1 (w/w). In some embodiments, the ratio of lipid to telodendrimer is from about 200:1 to about 5:1 (w"w). In some embodiments, the ratio of lipid to telodendrimer is about 99:1 (w/w). In some embodiments, the ratio of lipid to telodendrimer is about 9:1 (w/w). Other weight ratios of lipid to telodendrimer can also be useful in the present invention.

In some embodiments, any of the nanodiscs as described above further include a drug. The drug can be noncovalently sequestered in the nanodisc, covalently linked to a telodendrimer conjugate as an R group as described above, covalently linked to the head group of the lipid, or otherwise associated with the nanodisc. Non-limiting examples of drugs that can be included in the nanodiscs are bortezomib, paclitaxel, SN38, camptothecin, etoposide and doxorubicin, docetaxel, daunorubicin, prednisone, dexamethasone, vincristine, vinblastine, temsirolimus and carmustine. Other suitable drugs include, but are not limited to, cytostatic agents, cytotoxic agents (such as for example, but not limited to, DNA interactive agents (such as cisplatin or doxorubicin)); taxanes (e.g. taxotere, taxol); topoisomerase if inhibitors (such as etoposide); topoisomerase I inhibitors (such as irinotecan (or CPT-11) or topotecan); tubulin interacting agents (such as paclitaxel, docetaxel or the epothilones); hormonal agents (such as tamoxifen); thymidilate synthase inhibitors (such as 5-fluorouracil); anti-metabolites such as methotrexate); alkylating agents (such as temozolomide (TEMODAR™ from Schering-Plough Corporation, Kenilworth, N.J.), cyclophosphamide); aromatase combinations; cytarabine (ara-C), doxorubicin, cyclophosphamide, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovorin, oxaliplatin (ELOXATIN™ from Sanofi-Synthelabo Pharmaceuticals, France), Pentostatin, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Raloxifene, Droloxafine, or Hexamethylmelamine. Prodrug forms are also useful in the present invention. Other drugs useful in the present invention also include radionuclides, such as $^{67}$Cu, $^{90}$Y, $^{123}$I, $^{125}$I, $^{131}$I, $^{177}$Lu, $^{188}$Re, $^{186}$Re and $^{211}$At. In some embodiments, the nanodiscs of the present invention include a drug selected from amphotericin B and SN38.

The nanodiscs can also include additional components such as diagnostic agents. A diagnostic agent used in the present invention can include any diagnostic agent known in the art, as provided, for example, in the following references: Armstrong et al., *Diagnostic Imaging*, 5$^{th}$ Ed., Blackwell Publishing (2004); Torchilin, V. R, Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can also include single photon emission computed tomography (SPECT), magnetic resonance imaging (MRI), optical imaging, positron emission tomography (PET), computed tomography (CT), x-ray imaging, gamma ray imaging, and the like. A diagnostic agent can include chelators that bind to metal ions to be used for a variety of diagnostic imaging techniques. A radioisotope can be incorporated into some of the diagnostic agents described herein and can include radionuclides that emit gamma rays, positrons, beta and alpha particles, and X-rays. The diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). The diagnostic agents can include magnetic resonance (MR) and x-ray contrast agents that are known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). The diagnostic agents can be associated with the nanodiscs in a variety of ways including, for example, being covalently bound to a nanodisc component or noncovalently embedded or encapsulated in the nanodisc.

The nanodiscs can also include one or more targeting agents. Generally, a targeting agent can associate with any target of interest, such as a target associated with an organ, tissues, cell, extracellular matrix, or intracellular region. A target can be associated with a particular disease state, such as a cancerous condition. The targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. The target can also be a carbohydrate, such as a monosaccharide, disaccharide, or polysaccharide that can be, for example, present on the surface of a cell. The targeting agent can be a target ligand (e.g., an RGD-containing peptide), a small molecule mimic of a target ligand (e.g. a peptide mimetic ligand), or an antibody or antibody fragment specific for a particular target. Targeting agents can further include folic acid derivatives, B-12 derivatives, NGR derivatives, somatostatin derivatives or peptides that bind to the somatostatin receptor, e.g., octreotide and octreotate, and the like. The targeting agents can also include an aptamer. Aptamers can be designed to associate with or bind to a target of interest, Aptamers can be comprised of, for example, DNA, RNA, and/or peptides, and certain aspects of aptamers are well known in the art. (See. e.g., Klussman, S., Ed., The Aptamer Handbook, Wiley-VCR (2006); Nissenbaum, E. T., *Trends in Biotech.* 26(8): 442-449 (2008)). The targeting agents can be associated with the nanodiscs in a variety of ways including, for example, being covalently bound to a nanodisc component or noncovalently embedded or encapsulated in the nanodisc. In particular, pathogen-, tissue-, or tumor-specific ligands can be covalently conjugated to the distal end of the PEG segment in the telodendrimer during synthesis to allow for targeted drug delivery.

Any measuring technique available in the art can be used to determine properties of the nanodiscs. For example, techniques such as dynamic light scattering, x-ray photoelectron microscopy, powder x-ray diffraction, scanning electron microscopy (SEM), transmission electron microscopy (TEM), and atomic force microscopy (AFM) can be used to determine average size and dispersity of the nanodiscs. In general, the nanodiscs of the present invention are less than one micron in diameter. The diameter of the nanodiscs can be from about 25 nm to about 900 nm in diameter, or from about 50 nm to about 750 nm in diameter, or from about 100 nm to about 500 nm in diameter. In some embodiments, the nanodisc is less than about 1000 nm in diameter. In some embodiments, the nanodisc is less that about 100 nm in diameter. In some embodiments, the nanodisc is less that about 10 nm in diameter. The diameter of the nanodisc may also be less than 900 nm, or less than 800 nm, or less than 700 nm, or less than 500 nm, or less than 400 nm, or less than 300 nm, or less than 200 nm, or less than 75 nm, or less than 50 nm, or less than 40 nm, or less than 30 nm, or less than 20 nm, or less than 10 nm.

V. Methods of Making Nanodiscs

The apolipoprotein-telodendrimer nanodiscs of the present invention can be prepared by any methods known in the art. These methods can be cell-based methods or cell-free methods, and generally involve forming a vesicle of the telodendrimer and lipid, followed by addition of a membrane scaffold protein, such as apolipoprotein, to form the nanodiscs of the present invention. In some embodiments, the method is a cell-free method.

In some embodiments, the present invention provides a cell-free method of making a nanodisc. The method includes forming a vesicle having a telodendrimer and a lipid, wherein the ratio of lipid to telodendrimer is from about 500:1 to about 1:1 (w/w). The method also includes forming a reaction mixture of the vesicle and a membrane scaffold protein in the absence of a cell, thereby preparing the nanodisc.

Figure 1B:
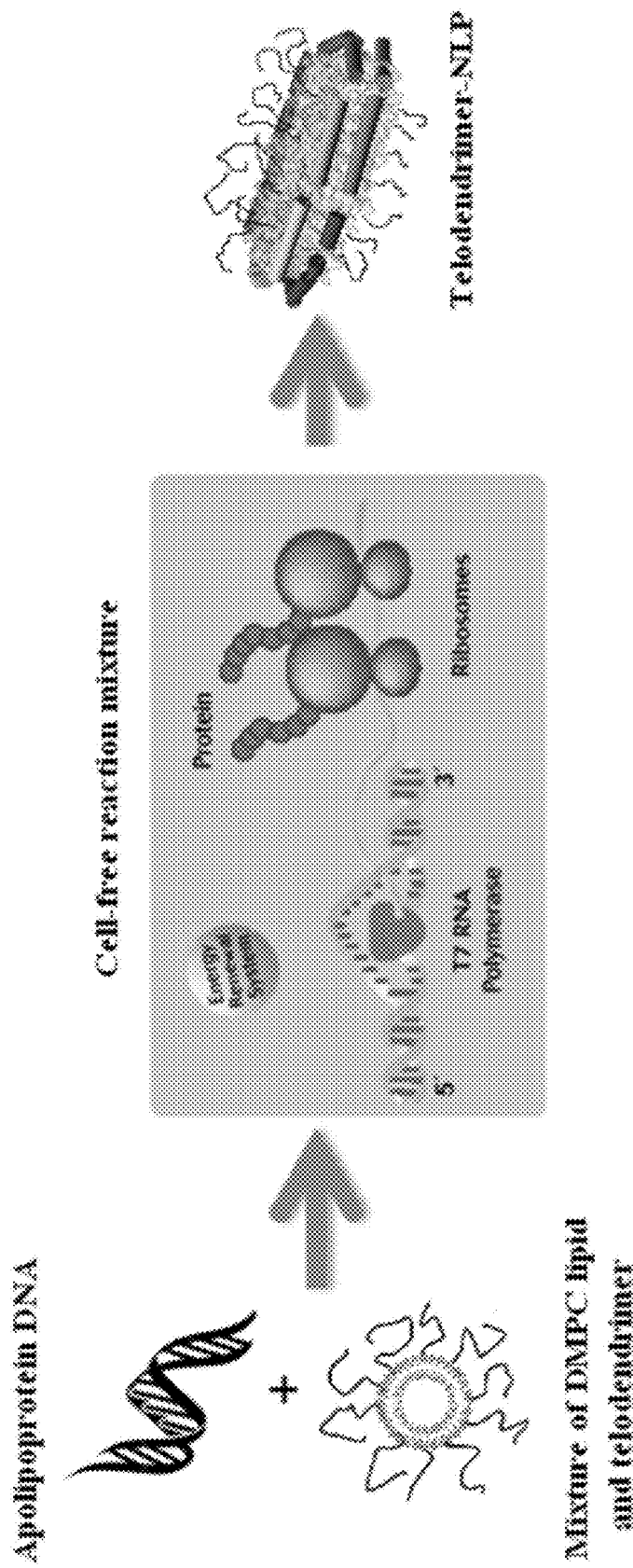

The cell-free process to produce NLPs in the presence of additional additives is outlined in FIGS. 1A-1B. Plasmid and telodendrimers were premixed with DMPC lipids, and added directly to cell free reactions to produce fully assembled nanoparticles. The NLPs were then separated with affinity purification. The entire process was completed in 4-24 hours and depended on the desired yield of total protein. Other additives such as fluorescent dyes used for visualization or membrane proteins/receptors encoded on plasmids were also included in some reactions.

Any membrane scaffold protein is suitable in the methods of the present invention. Representative membrane scaffold proteins are described above, and include, but are not limited to, apolipoprotein. In some embodiments, the membrane scaffold protein is apolipoprotein. In some embodiments, the apolipoprotein is apolipoprotein-A1. In some embodiments, the membrane scaffold protein can be the truncated apolipoprotein A-1 (Δ49A1).

Other optional components include lysates, butlers and polymerases. Any suitable lysate can be used, such as that provided by Santa Cruz Biotechnology. The reaction mixture can also include any suitable buffer, such as the Reaction Buffer, or PBS buffer. Suitable butlers include, but are not limited to, citric acid, acetic acid, dipotassium phosphate ($K_2HPO_4^-$), N-cyclohexyl-2-aminoethanesulfonic acid (CHES), borate, TAPS, bicine, tris, tricine, TAPSO, HEPES, TES, MOPS, PIPES, cacodylate, SSC, MES and succinic acid.

The reaction mixture can also include any suitable polymerase. Representative polymerases are described above. In some embodiments, the polymerase can be an RNA polymerase. The RNA polymerase can be suitable for preparing RNA from a DNA sequence, such as the apolipoprotein DNA sequence. In some embodiments, the polymerase can be RNA polymerase I, RNA polymerase II, RNA polymerase III or T7 RNA polymerase.

The nanodiscs of the invention can be prepared using any suitable ratio of lipid to telodendrimer. The ratio of lipid to telodendrimer in the nanodisc, for example, can be from about 500:1 to about 1:1 (w/w). For example, the ratio can be about 500:1, 400:1, 300:1, 200:1, 100:1, 99:1, 95:1, 90:1, 80:1, 75:1, 70:1, 60:1, 50:1, 40:1, 30:1, 25:1, 20:1, 15:1, 14:1, 13:1, 12:1, 10:1, 9:1, 8:1, 7:1, 6:1, 5:1, 4:1, 3:1, 2:1 or 1:1 (w/w). In some embodiments, the ratio of lipid to telodendrimer is from about 200:1 to about 5:1 (w/w). In some embodiments, the ratio of lipid to telodendrimer is about 99:1 (w/w). In some embodiments, the ratio of lipid to telodendrimer is about 9:1 (w/w). Other weight ratios of lipid to telodendrimer can also be useful in the present invention.

Any other suitable combination of lipids with telodendrimers and/or other components, as described above, can also be employed in the methods of the present invention. Still other weight ratios of lipid to telodendrimer may also be useful in the methods of the present invention. The methods may further include incorporation of additional components, such as drugs, diagnostic agents, and targeting agents, as described above, into the reaction mixture.

The reaction mixture generally includes a solvent or a mixture of solvents. In some embodiments, the reaction mixture further includes a solvent mixture. In general, the solvent mixture contains two or more solvents selected to sufficiently solubilize the lipid component and the telodendrimer component of the reaction mixture as well as any additional components. Suitable solvents include, but are not limited to, chloroform, dichloromethane, ethanol, methanol, acetone, hexanes, petroleum ether, diethyl ether, dioxane, tetrahydrofuran, and water.

In some embodiments, the method further includes contacting the dispersed lipid-telodendrimer mixture with a drug such that the drug is loaded into the nanodisc. The drug can be included in the solvent prior to contacting the lyophilized reaction mixture, or the drug may be added to the dispersed lipid-telodendrimer mixture after dispersion with the solvent. The dispersed lipid-telodendrimer mixture may be contacted with the drug for any amount of time sufficient to load the drug into the nanodiscs. So-called "passive" loading techniques involve the incorporation of drugs into a nanodisc during the nanodisc self-assembly process in solution, such that the drug is encapsulated or embedded within the nanodisc. Alternatively, the drugs can be actively loaded into nanodiscs. For example, the nanodiscs can be exposed to conditions, such as electroporation, in which the bilayer membrane is made permeable to a solution containing therapeutic agent thereby allowing for the drug to enter into the nanodisc. Loading of the nanodiscs with drugs or other components can be carried out via other methods known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006).

The methods of the invention may optionally include additional steps such as sonication and/or freeze-thaw cycles to aid in dispersion and self-assembly, extrusion to yield nanodiscs with homogenous size and shape, dialysis to remove or exchange soluble species such as unbound drugs and buffer salts, and other steps. These optional steps may occur at any time during the methods of the invention.

VI. Examples

Example 1: Preparation of Nanodiscs with Apoliprotein and Telodendrimers

Methods
  Plasmids:
    The truncated form of Apo A1 (Δ1-49) or Δ49ApoA1 was cloned into pIVEX2.4d using NdeI and SmaI restriction sites. This vector contained a His-tag used for nickel affinity purification as previously described (Cappuccino et al 2008),
  Preparation of Dendrimers:
    We have previously published on the use of telodendrimers for NLP optimization (Luo et al). PEG$^{5k}$-CA$_8$ and related cholesterol or cholic acid based amphiphilic polymers, were prepared according to the published methods. For the telodendrimer-lipid mixtures a total of 25 mg/mL DMPC and each individual polymer were mixed at different molar ratios at an approximate 0.5-10%. The mixtures of DMPC/polymer were then sonicated for 15 min, or until optical clarity was achieved. Samples were kept on ice during the entire sonication process. After the sonication, samples were centrifuged at 13000 RCF for 2 mins to remove any metal contamination from the probe tip.
  DMPC/Polymer Preparation:
    Small unilamellar vesicles of DMPC (Avanti) were prepared by probe sonication of a 25 mg/mL aqueous solution of DMPC until optical clarity was achieved; typically 15 min was sufficient. Samples were kept on ice during the sonication process. After the sonication, the samples were centrifuged at 13000 RCF for 2 minutes to remove metal contamination from the probe tip. Telodendrimes lipid mixtures were created with the above method with a total of 25 mg/mL DMPC and each individual polymer mixed at varying molar ratios between approximately 0.5-10%. 0.1% TexasRed-POPC (Invitrogen) was added to the DMPC solution before sonication if a fluorescent label on the NLP complex was desired.
  Cell-Free Reactions:
    Small-scale reactions (100 uL) or large scale (1 mL) were carried out using the Invitrogen's Expressway Maxi kit. Reaction components (Lysate, Reaction buffer, T7 Polymerase, Amino Acid Mix, and Methionine) were combined as specified by the manufacturer. 10 μg of Δ49ApoA1 DNA was added to each 1 mL reaction. To each 1 mL reaction, 2 mg DMPC/polymer mixture was then added. The reactions were incubated at 30° C., with shaking at 990 rpm for 2-18 hrs in thermomixer.
  Affinity Purification of NLP Complexes:
    Immobilized metal affinity chromatography was used to isolate the protein of interest (Δ49ApoA1) from the cell-free reaction mixture. 2 ml of 50% slurry nickel-nitrilotriacetic acid Superflow resin (Qiagen) was equilibrated with PBS (50 mM Na2HPO4. 300 mM NaCl, pH 8.0) under native conditions in a 10 mL capped column. Mixed the total cell free reaction (1 ml) with the equilibrated resin, and was incubated/nutated on ice for 2 hr. 1 ml of slurry and 5 mL capped column were used for the purification from small-scale reactions. The column was then washed with increasing concentrations of imidazole 10, 20 and 50 mM in the mentioned PBS buffer. Two column volumes (CV) of each wash buffer were used for a total of 6 CVs of washing. The His-tagged proteins of interest were eluted in six 1 mL fractions of 400 mM imidazole, PBS buffer. All elutions were combined, dialyzed against PBS for 18 hrs at 4° C. with stirring. After that, the combined elution was concentrated using a 100K MWCO molecular weight sieve filters (Vivascience) to a volume of ~200 uL.
  Size Exclusion Chromatography:
    The NLPs were resolved by HPLC (Shimadzu) using a Superdex 200 10/300 GL column (GE Healthcare) with TBS running buffer (10 mM Tris pH 7.4; 0.15M NaCl; 0.25 mM EDTA, 0.005% NaN3) at a flow rate of 0.5 ml/min. The column was calibrated with four protein standards (HMW Gel Filtration Calibration kit, GE Healthcare) of known molecular weight and Stokes diameter that span the separation range of the column and the NLP samples. The void volume was established with blue dextran.

SDS PAGE:

10 μL aliquot of the purified NLPs or lipid micelles were mixed with 10 μL 2×LDS Sample buffer with reducing agents (Invitrogen), heat denatured and loaded on to a 4-12% gradient pre-made Bis-Tris gel (Invitrogen) along with the molecular weight standard NovexSharp (Invitrogen). The running buffer was IX MES-SDS (Invitrogen). Samples were electrophoresed for 38 minutes at 200V. Gels were stained with coomassie brilliant blue.

Native PAGE:

10 μL aliquot of the purified NLPs or lipid micelles were mixed with 2× native gel sample butler (Life Technologies: Invitrogen) and loaded onto 4-12% gradient pre-made Tris-glycine gels (Life Technologies:Invitrogen). Samples were electrophoresed for 2 hours at 125 V. After electrophoresis, gels were imaged using the laser (488 nm) of a Typhoon 9410 (GE Healthcare) with a 520 nm bandpass 30 filter for the detection of the produced NLPs with incorporated FITC labeled polymer. For detection of the produced NLPs with incorporated TexasRed-POPC, the laser (532 nm) with a 610 nm bandpass 30 filter is used. Molecular weights were determined by comparing migration vs. log molecular weight of standard proteins found in the NativeMark standard (Life Technologies:Invitrogen).

Dynamic Light Scattering:

The measurements were performed on a Nanotrac Particle Size Analyzer (Microtrac). Light from a laser diode was coupled to the sample through an optical beam splitter in the Nanotrac probe assembly. The interface between the sample and the probe was a sapphire window at the probe tip. The sapphire window reflected the original laser back through the beam splitter to a photodetector. This signal with the same frequency as the original laser acted as a reference signal for detection, offering heterodyne detection. The laser passed through the sapphire window and was scattered by the particles, which were in suspension but moving under Brownian motion. The laser was frequency shifted according to the Doppler Effect relative to the velocity of the particle. Light was scattered in all directions including 180 degrees backwards. This scattered, frequency shifted light was transmitted through the sapphire window to the optical splitter in the probe to the photodetector. These signals of various frequencies combined with the reflected signal of un-shifted frequency (Controlled Reference) to generate a wide spectrum of heterodyne difference frequencies. The power spectrum of the interference signal was calculated. The power spectrum was then inverted to give the particle size distribution.

Cryo Transmission Electron Microscopy.

All samples were preserved as a frozen hydrated specimen in the presence of saturated ammonium molybdata and examined with a JEOL JEM-2100F transmission electron microscope at magnification of 80,000× under liquid nitrogen temperature. Clusters of NLPs were found with plain NLP sample, while only a few clusters of NLPs were found with telodendrimer NLPs. Majority of the NLPs are shown inside views. A few of them appeared in their top view. Tobacco mosaic virus (TMV) was added as reference to indicate the quality of cryo-EM preparation, as well as the internal calibration of microscope magnification. The size of the nanoparticles varied from 10 nm to 15 nm.

Solution Phase Characterization Using Fluorescent Correlation Spectroscopy (FCS).

Characterization of nano-particles and their dynamic shape and association in solution remains a challenge, which we have addressed using FCS performed on a MicroTime 200 single molecule fluorescence lifetime measurement system (PicoQuant). FCS is capable of measuring molecular diffusion statistics in solution with sensitivity for single molecule fluorescence. This allows us to rapidly and accurately determine the hydrodynamic radii of the newly formed nano-complexes in an aqueous environment. Complimentary techniques such as dynamic light scattering (DLS) performed on a Nanotrac Particle Size Analyzer (Microtrac) and potentially atomic force microscopy (AFM) can be used to further validate FCS data.

TABLE 1

NLP size and level of aggregation with and without telodendrimers.

| Additive | M.W.[a] | NLP size (nm)[b] | S.D.[c] | Aggregate %[d] | μg/mL |
|---|---|---|---|---|---|
| $PEG^{2K}$_D-$CA_4$ | 4 kDa | 6.76 | 0.30 | 0.00 | |
| $PEG^{2K}$_D-$CA_8$ | 6 kDa | 13.32 | ND | 1.00 | |
| $PEG^{5K}$-D-$CF_4$ | 7 kDa | 27.14 | 5.32 | 15.00 | 750 |
| $PEG^{5K}$-D-$CF_8$ | 9 kDa | 17.58 | 4.59 | 16.00 | |
| DMPC | 0.68 kDa | 40.30 | 1.27 | 100.00 | 190 |

[a]Molecular weight of additive telodendrimer or lipid alone.
[b]Resulting size of monodispersed NLPs as measured by Dynamic light scatter.
[c]Standard deviation between replicate experiments.
[d]Dynamic light scattering measure of aggregated material.

Results

Telodendrimer Addition Increases the Soluble Yield of Nanoparticles.

A total of 1 ml of cell-free reaction with and without telodendrimer were used to compare protein yield and solubility of the NLP product (FIGS. 1A-4B). Several types of telodendrimers were utilized as depicted in Table 1. Telodendrimer molecules used included: $PEG^{2k}$-$CA_4$ containing 4 cholic acid molecules linked to a single linear PEG chain (2 kDa); $PEG^{2k}$-$CA_8$ containing 8 cholic acid molecules linked to a single linear PEG chain (2 kDa); $PEG^{5k}$-$CF_4$ containing 4 cholesterol molecules linked to a single linear PEG chain (5 kDa); $PEG^{5k}$-$CA_8$ containing 8 cholic acid molecules linked to a single linear PEG chain (5 kDa). A 4-12% SDS-PAGE gel was used to separate the products and nickel affinity chromatography was used for purification. The profile of NLP or telodendrimer conjugated NLP is shown in FIGS. 2A-2B. We noted a 2-4 fold increase of soluble telodendrimer conjugated NLP produced when compared to NLP alone. As seen in FIGS. 2A-2B, the $PEG^{5k}$-$CA_8$ telodendrimer reaction yielded approximately 750 ug/mL of Telo-NLP, compared to 190 ug/mL of NLP alone. This difference appeared to be independent of the total amount of delta-A poA1 protein produced.

Telodendrimers Impacted the Size and Level of Aggregation of Nanoparticles.

Figure 3A:
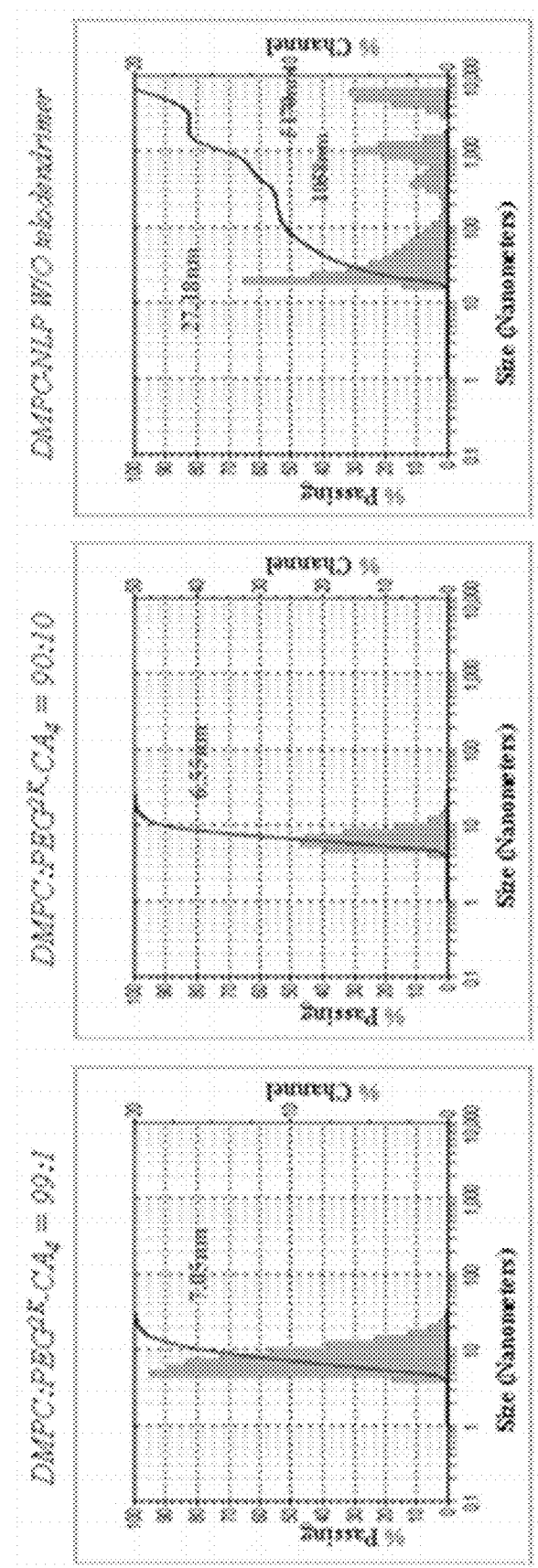
FIGS. 3A-3C show telodendrimer addition to nanoparticle formation changed aggregation levels and size tenability. Dynamic Light Scattering (DLS) was used to assess several biophysical properties of the Telo-NLP particles.
Figure 3B:
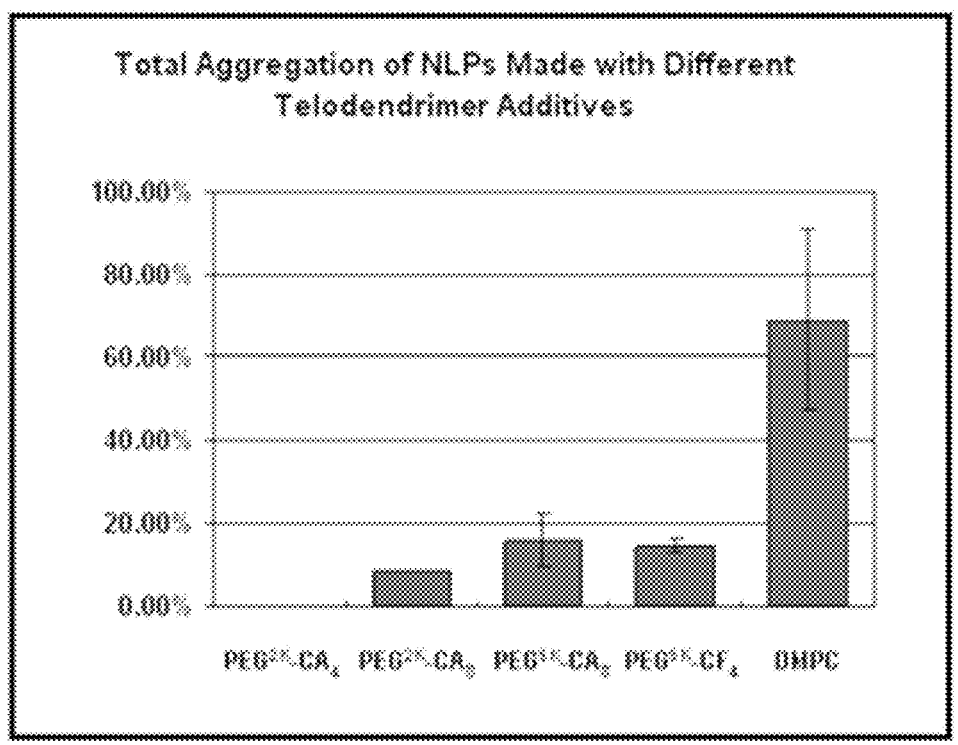
Figure 3C:
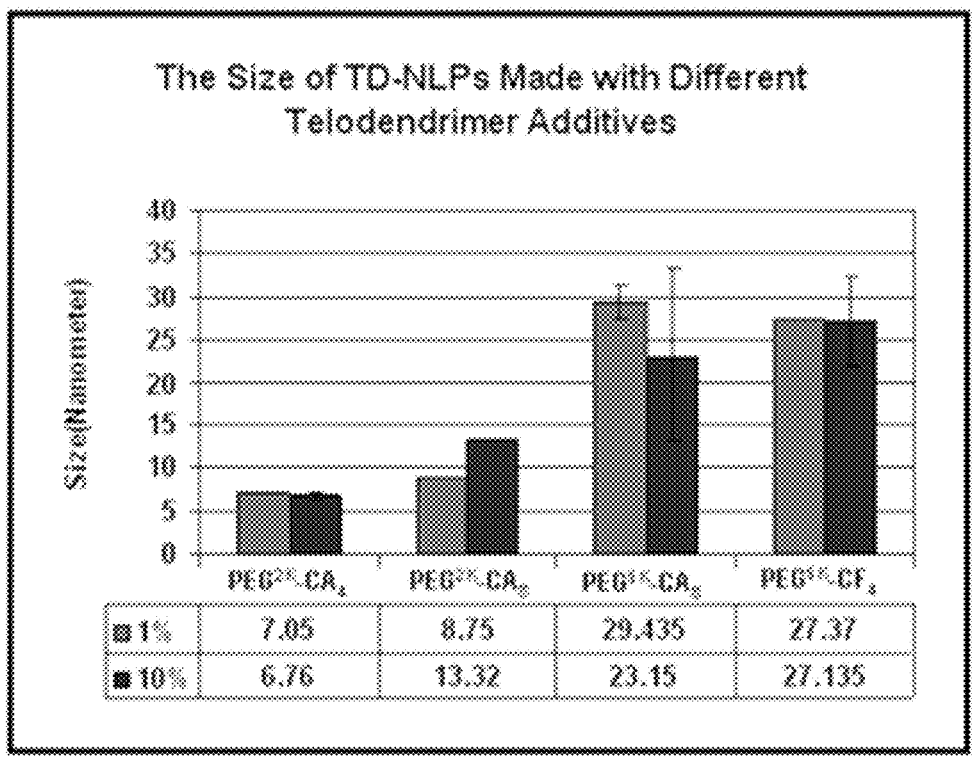

Dynamic light scattering (DLS) was used to evaluate the size and monodispersity of the NLPs compared to Telo-NLPs. The overall size of the NLPs were dependent upon the length of the incorporated PEG molecule. The $PEG^{2k}$ Telo-NLPs ranged in size from 7 to 13 nm, while the $PEG^{5k}$Telo-NLPs were 15 to 30 nm in diameter based on DLS traces (FIG. 3C). Previously reported studies have shown that NLPs alone measure approximately 8 nm in solution when dispersed (Gao et al., 2011). Changing the amount of telodendrimer added to the NLP assembly process over a range of 1-10% of total lipid did not significantly alter the overall size of the Telo-NLPs (FIGS. 3A and 3C).

NLP aggregation appears to be size dependent, with larger telodendrimer molecules exhibiting higher levels of aggregation. The overall level Telo-NLPs aggregation rate was reduced 10-100 times compared to NLPs assembled only in the presences of DMPC alone (FIGS. 3A-3B). Increases in the amount of telodendrimer to lipid ratio (>10%), was associated with greater levels of aggregation (data not shown). There were no significant changes in NLP size or aggregation when adjusting for telodendrimers containing cholate or cholesterol head groups over the 1-10% telodendrimer to lipid ratio.

Telo-NLP Complexes are Disc Like in Shape.

Figure 4A:
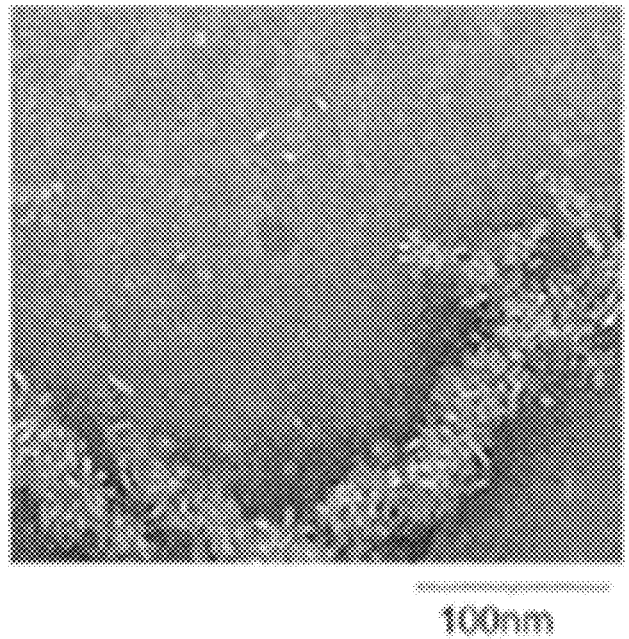
FIGS. 4A-4D show disc-like structures with decreased aggregation of telodendrimer NLP complexes compared with NLP alone. CryoEM visualization of NLP preparations with and without telodendrimers are shown to reduced aggregation levels of Telo-NLPs.
Figure 4B:
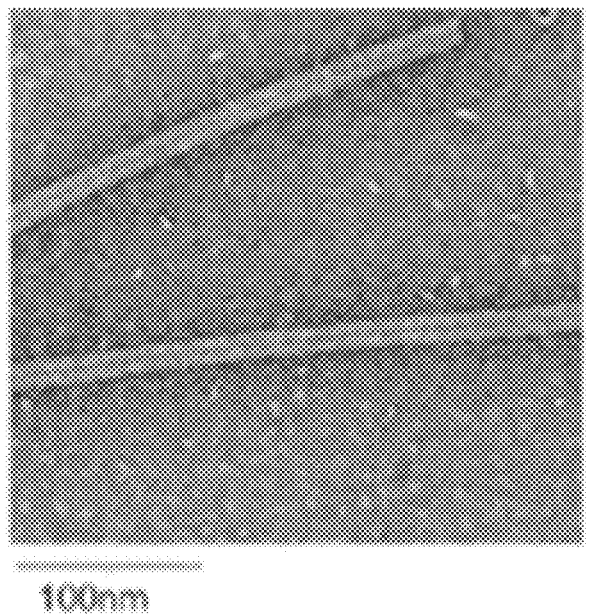
Figure 4C:
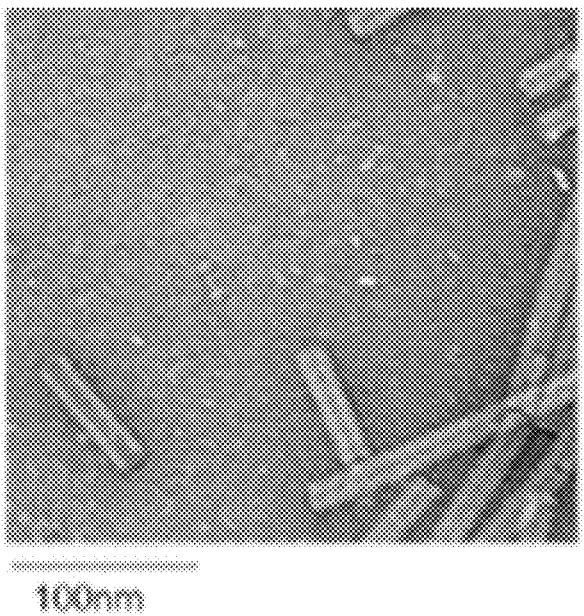
Figure 4D:
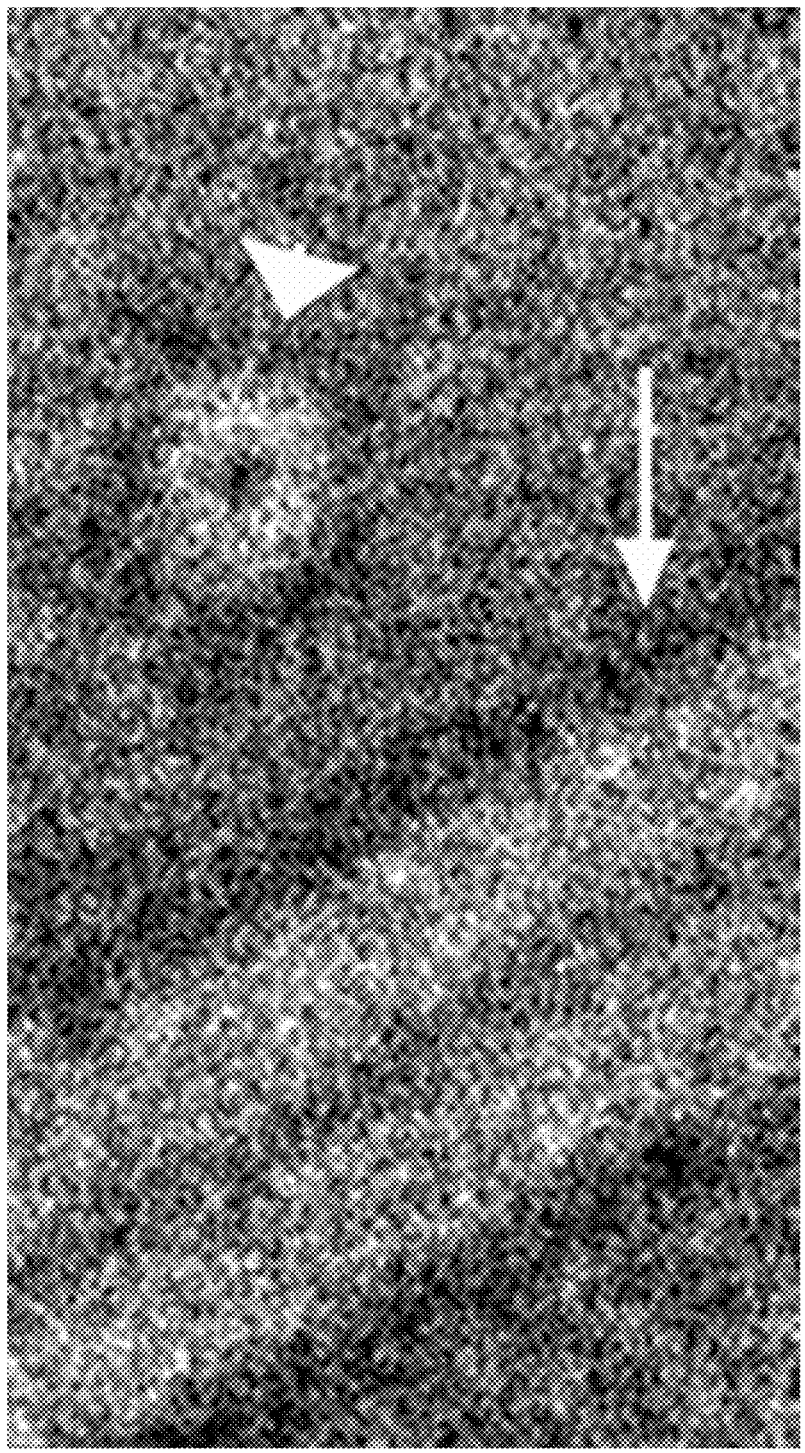

FIGS. 4A-4D illustrate in Cryo TEM images that NLPs are discoidal in shape with height dimensions consistent with previously published images of NLPs and nanodisc that are based on phospholipid bilayers with diameters averaging about 10 nm. Three assemblies are shown in FIGS. 4A-4C, with DMPC alone (FIG. 4A) and two types of telodendrimers (FIGS. 4B-4C). Unlike previous reports, NLPs alone (FIG. 4A) in our study exhibited large clustering rather than stacked particles, or "rouleaux," which may be attributable to the inclusion of tobacco virus particles in this study.

Figure 5:
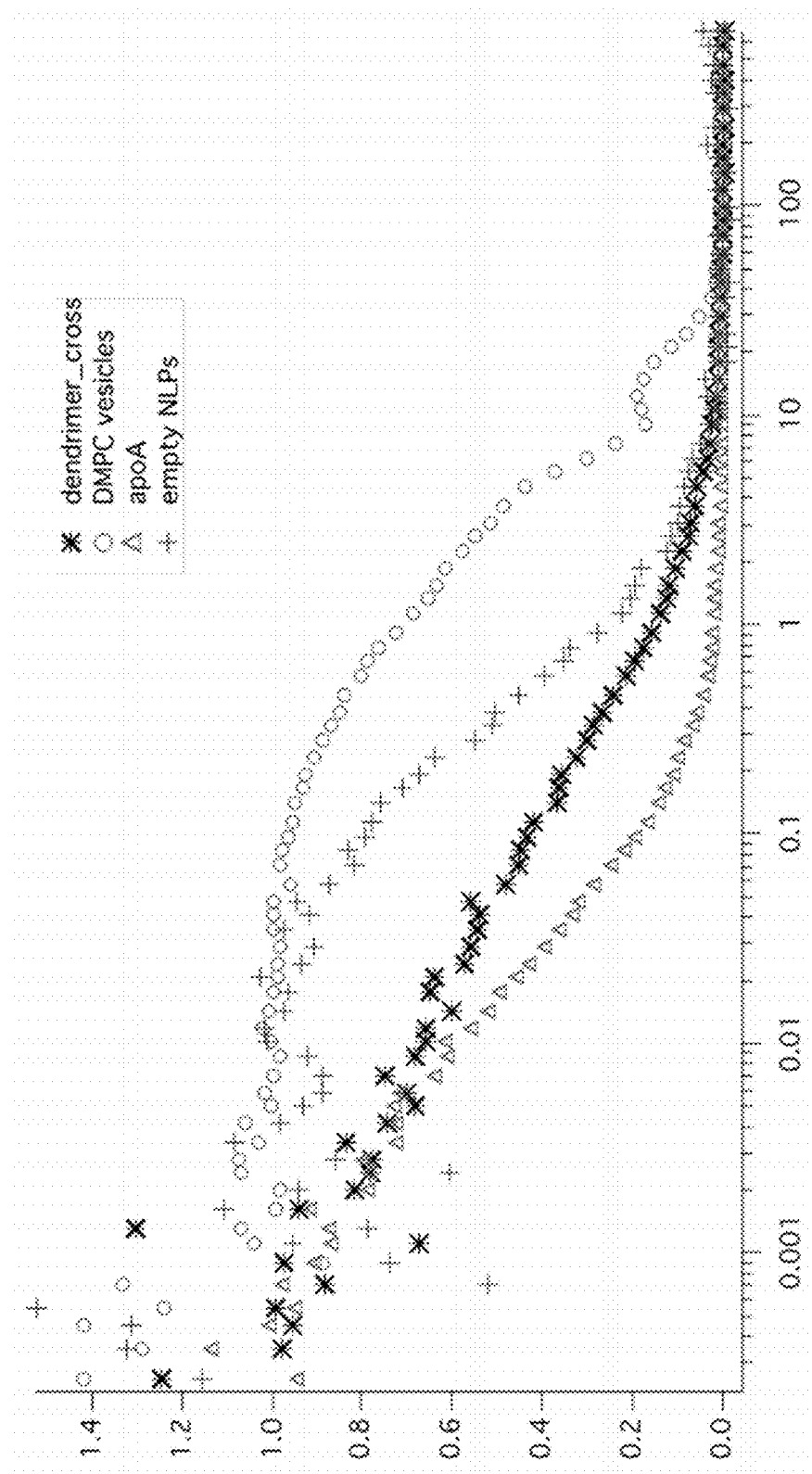
FIG. 5 shows the telodendrimers are associated with nanoparticles as a complex. Diffusion curves of proteins and NLP/Telo-NLP complexes as measured by FCS. The curves correspond to Δ49A1 (triangle), Telo-NLP (star), NLP (plus) and DMPC (circle) vesicles in 1×PBS respectively.

FCS analysis has been used to topologically confirm telodendrimer association and labeling of NLP (Gao et. al 2011). Cell-free reactions were used to assemble NLPs tagged with Bodipy®-FL, which included Texas Red labels within the complex. As seen in FIG. 5, both NLP and Telo-NLP complex (identified by cross-correlating Bodipy/FITC and Texas Red in the complex) diffused significantly faster than DMPC vesicles alone, but slower than the protein Δ49ApoA1 (apolipoprotein without any DMPC). In addition, native gel electrophoresis was used to compare the molecular weight of NLPs to Telo-NLPs. The size of the NLPs approximated 240 kDa (data not shown), which was consistent with the FCS analysis.

Telo-NLPs Support Incorporation of Functional Intergral Membrane Proteins.

Figure 6A:
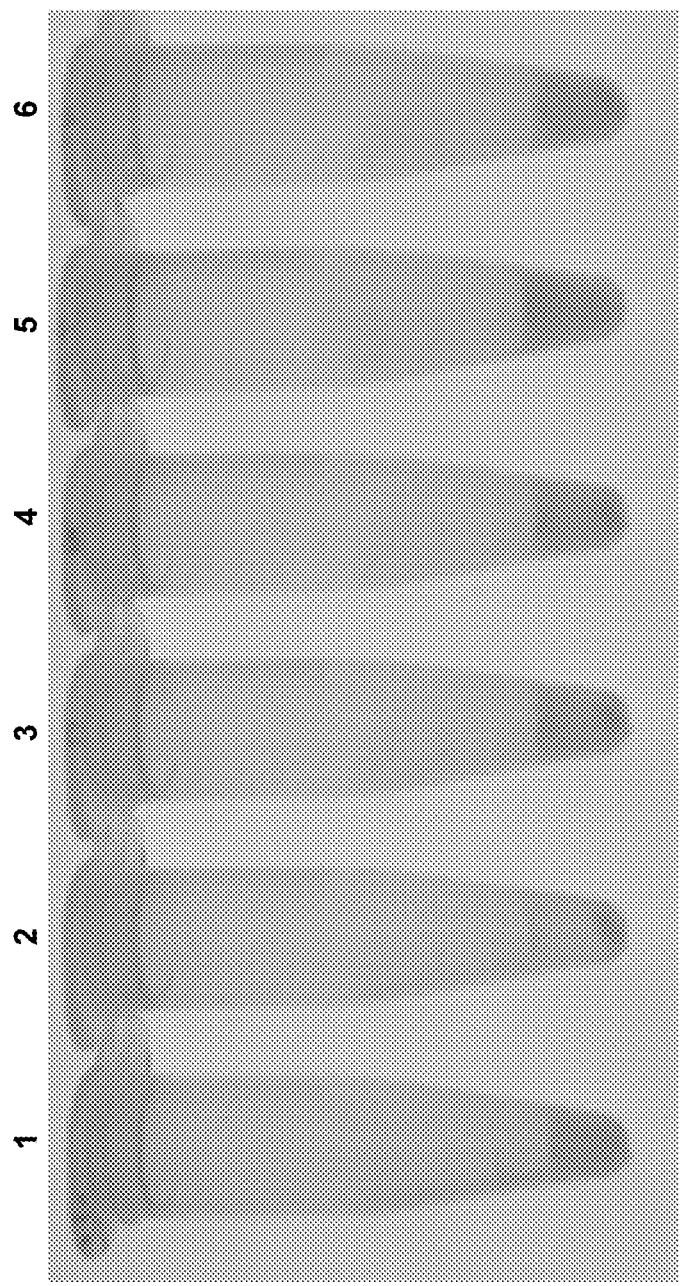
FIGS. 6A-6B show the telodendrimers are compatible with membrane protein production. The cell free reactions are setup with 1 ug/mL pIVEX-2.4b-apo.A1 and 10 ug/mL pIVEX-2.4b-boP and 2 mg/mL lipid (100% DMPC or 99.5% DMPC and 0.5% telodendrimer, molar ratio), BODIPY-FL and 50 uM all trans retinal, 30 C at 990 rpm for 4 hours.
Figure 6B:
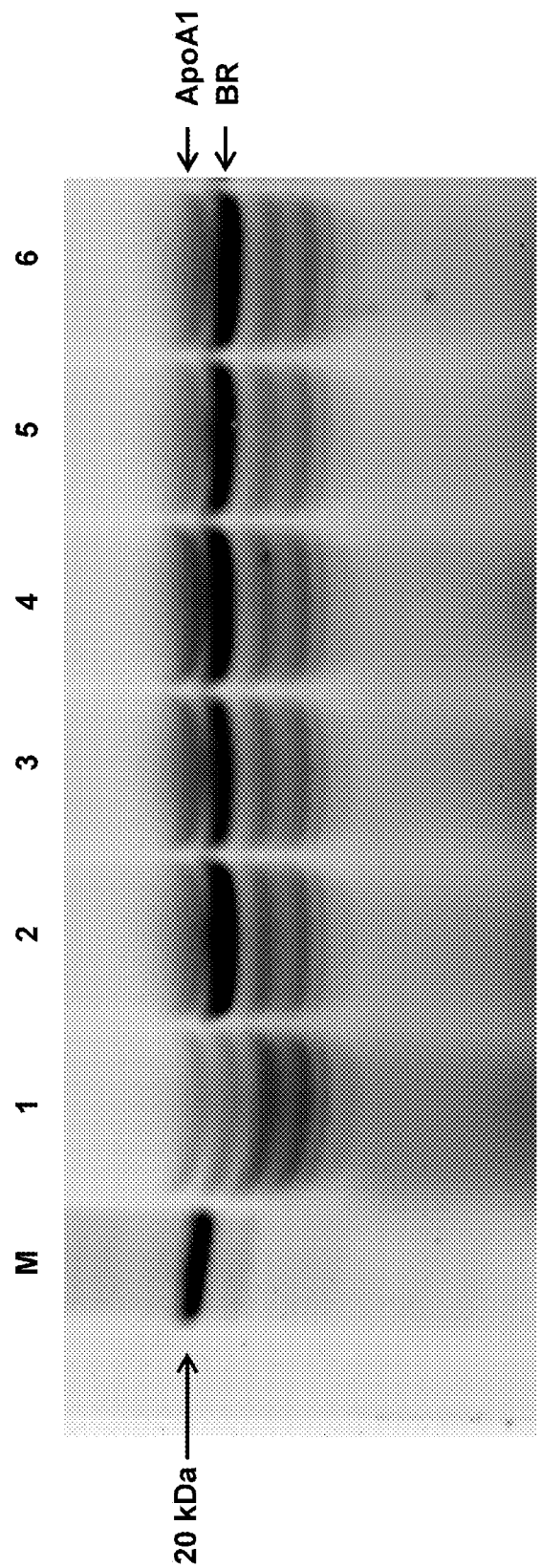

It has been previously shown, that bacteriorhodopsin (bR; a seven transmembrane helical protein, from *Halobacterium salinarium*) can be robustly co-expressed and assembled into NLPs for biophysical characterization (cappuccino et al. 2008; Katzen et al., 2008; Gao et al., 2011). In this study, assembly of the soluble bR-NLP complex was observed within 4 h after addition of plasmids to an *E. coli* cell-free lysate (FIG. 6A). Addition of telodendrimers to the cell-free reaction did not affect bR function as indicated by the pink coloration of the tubes, which is an indication of proper folding and function. Production of similar amounts of total bR protein with and without telodendrimers was also observed (FIG. 6B).

Telodendrimer addition can increase the soluble yield of nanoparticles. A total of 1 ml of cell-free reactions with and without Telodendrimer DMPC were used to compare protein yield as well as solubility for NLP purification (FIG. 1A). Several different types of telodendrimers as shown in Table 1. Telodendrimer molecules used were: $PEG^{2k}$-$CA_4$ containing 4 Cholesterol molecules linked to a single linear PEG molecule (2 kDa); $PEG^{2k}$-$CA_8$) containing 8 Cholesterol molecules linked to a single linear PEG molecule (2 kDa); $PEG^{5k}$-$CF_4$ containing 4 cholic acid molecules linked to a single linear PEG molecule (5 kDa); $PEG^{5k}$-$CF_8$ containing 8 cholic acid molecules linked to a single linear PEG molecule (5 kDa). A 4-25% SDS-PAGE gel was used to generate a typical profile for a NLP or Telo-NLP purification using nickel affinity chromatography as shown in FIGS. 2A-2B. In typical reactions a general increase of 2-4 fold of soluble Telo-NLPLs was noted compared to NLPs alone.

For example using the $PEG^{5k}$-$CF_8$ telodendrimer yielded approximately 750 ug/mL of Telo-NLP compared to 190 ug/mL of NLP. This difference did not appear to be related to the total amount of delta-ApoA1 protein produced, see FIGS. 2A-2B lanes containing total protein lysates from the cell-free reaction. This appears to reflect increase in the amount of soluble NLP produced by the addition of the telodendrimer (See FIGS. 2A-2B, elution lanes).

Telodendrimers impact the size and level of aggregation level of nanoparticles. Dynamic light scattering (DLS) was used to look at the size and general monodispersity of the NLPs compared to the Telo-NLPs. The telodendrimer molecules impacted the size of the nanolipoprotein particles depending on the length of the PEG linear molecule. Table 1. list the DLS diameters and levels of aggregation. The $PEG^{2k}$ molecules ranged in size between 7 and 13 nm, while the $PEG^{5k}$Telo-NLPs were 18-27 nm in diameter based on DLS traces (FIGS. 3A-3C). The known diameter of the NLPs alone was 40 nm, but this size was most likely due to the level of aggregation of the samples, which was consistently seen across replicate experiments. Previously reported studies have shown that NLPs are around 8 nm in solution when dispersed. There was also a size dependence for the level of aggregation with the larger telodendrimer molecules having a higher level of aggregation. Interestingly, these levels were 10-100 times less than the level of aggregation seen in the NLP alone sample. Thus indicating an increased monodispersity by inclusion of the telodendrimers in the cell-free reactions. Altering the amount of telodendrimer added to the NLP assembly process aver a range of 0.5-10% of total lipid did not alter the general size of the Telo-NLPs (FIGS. 4A-4D.). However, greater increases (>10%) in the amount of telodendrimer to lipid ratio did cause greater levels of aggregation. No significant change was observed in the size or aggregation level for the difference in the number of cholate or cholesterol tails over the 0.5-10% ratio.

Telo-NLP complexes are disc like in shape. A. FIG. 5. show NLPs whose dimensions are consistent with previously described observations. Three of these assemblies made are shown, with DMPC (FIG. 4A) and two different assemblies with telodendrimers (FIG. 4B). Unlike previous reports, we observed large clustering of the NLPs rather than stacked particles—described as "rouleaux". Combined, EM data suggests discoidal structures with height dimensions consistent with a phospholipid bilayer and a diameters of about 10-25 nm. Telodendrimer addition during assembly clearly changed the aggregation status of the particles as shown in FIG. 5.

FCS analysis was also used to compare the NLP assemblies and demonstrate that the telodendrimer molecules were associated with the NLP. Importantly, FCS can also be used to illustrate labeling of the NLP via the telodendrimer and to potentially confirm other topological features of the particles. Cell-free were assembled NLPs tagged with Bodipy®-FL and included Texas Red labels within the complex. The Telo-NLPs were labelled with FITC directly coupled to the telodendrimers and included Texas Red labels on the lipids. As seen in FIGS. 6A-6B, both the NLP and Telo-NLP complex (identified by cross-correlating Bodipy and Texas Red in the complex) diffused significantly faster than DMPC vesicles alone. However, this diffusion time was also significantly slower than Δ49A1 (apolipoprotein without any DMPC), providing further evidence for the complex formation.

Figure 7:
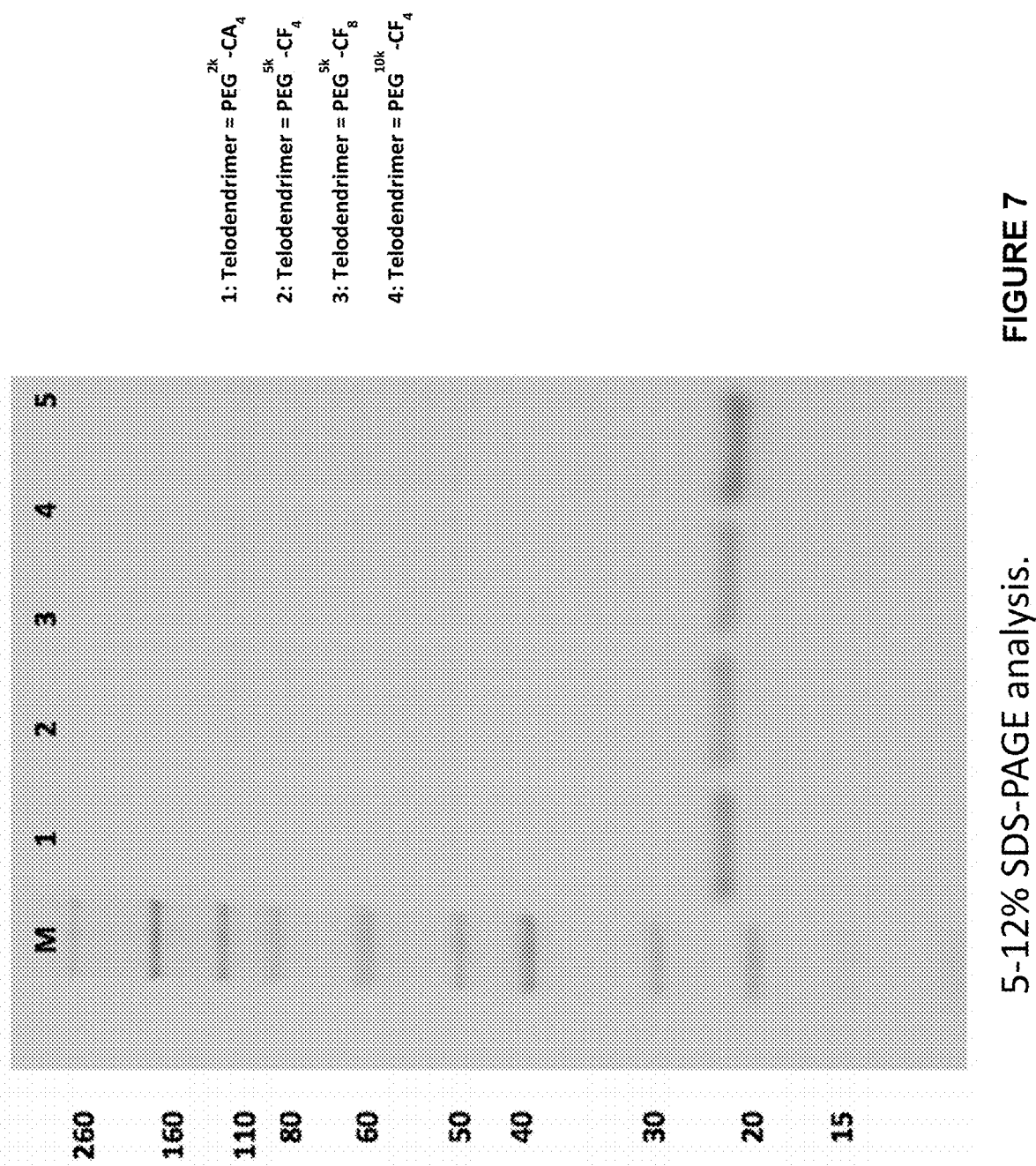
FIG. 7 shows an SDS-PAGE analysis using PEG$^{2k}$-CA$_4$ (lane 1), PEG$^{5k}$-CF$_4$ (lane 2), PEG$^{5k}$-CF$_8$ (lane 3) and PEG$^{10k}$-CF$_4$ (lane 4), which demonstrates that the telodendrimer-nanolipoproteins are >90% homogenous.
Figure 8:
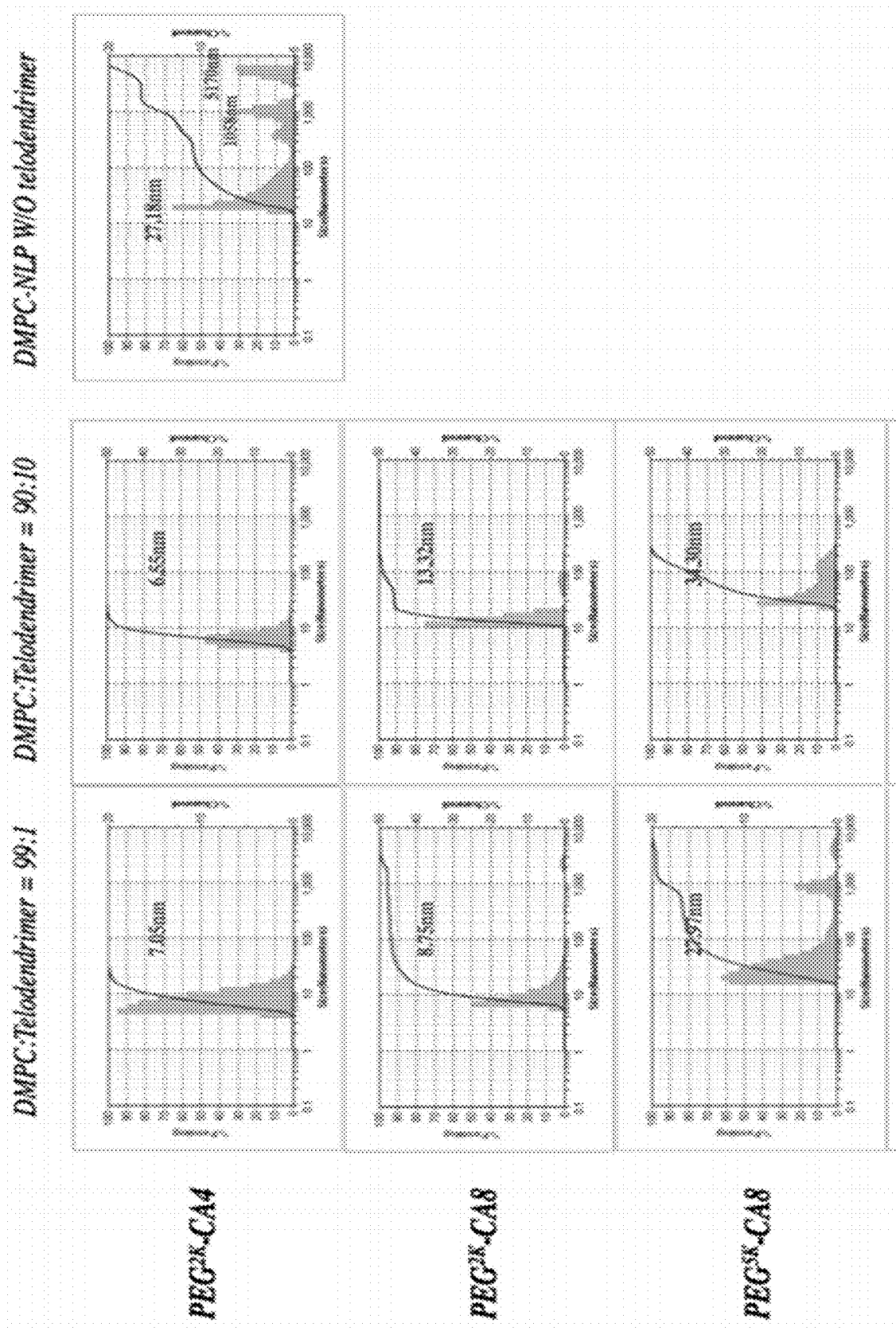
FIG. 8 provides a comparison of telodendrimer-nanolipoprotein size and aggregation using 1% and 10% levels of telodendrimer for PEG$^{2k}$-CA$_4$, PEG$^{2k}$-CA$_8$, PEG$^{5k}$-CA$_8$, PEG$^{5k}$-CA$_8$, PEG$^{5k}$-CF$_4$ and PEG$^{10k}$-CF$_4$
Figure 8:
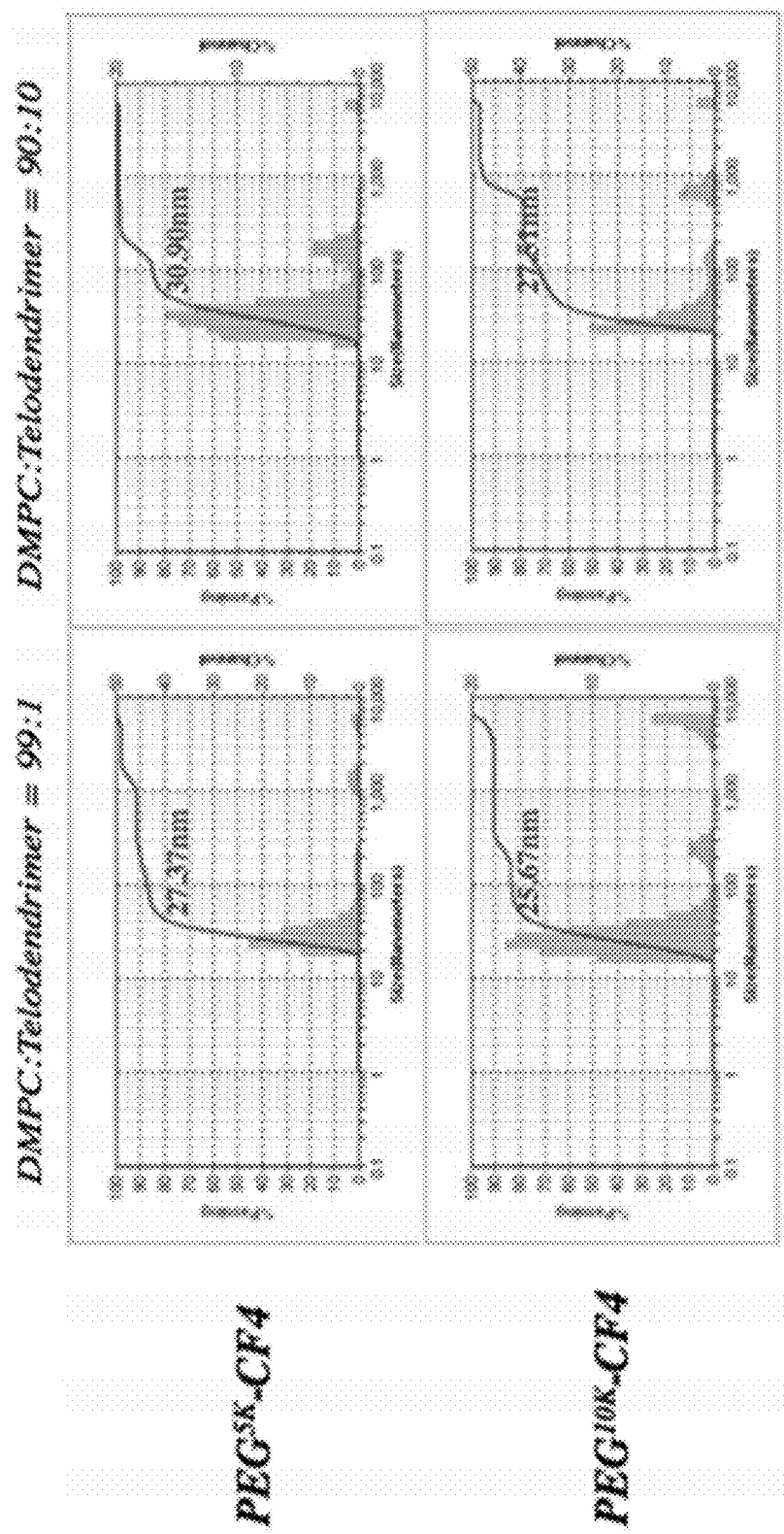
Figure 9:
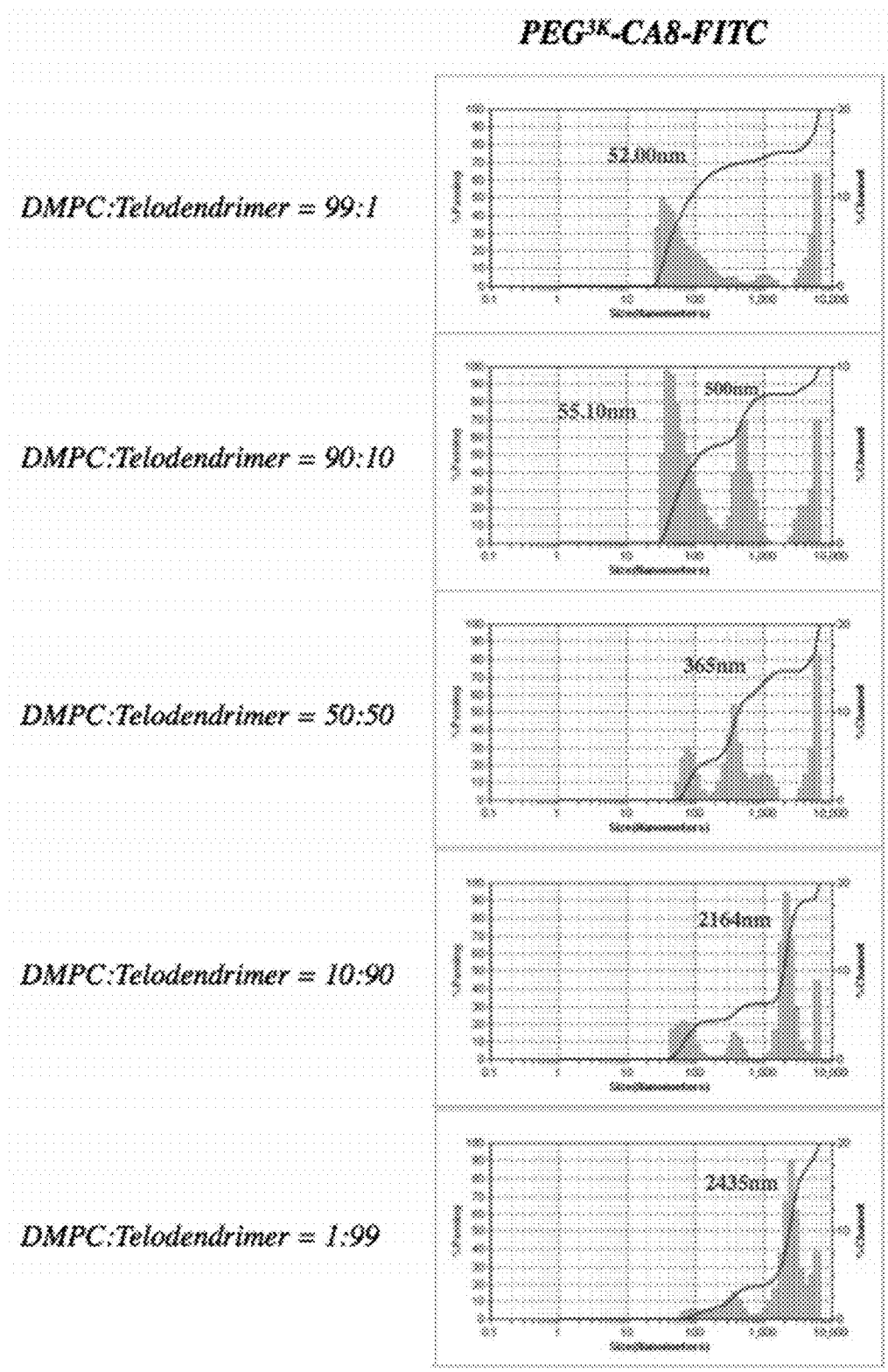
FIG. 9 shows aggregation of telodendrimer-nanolipoprotein for PEG$^{3k}$-CA$_8$-FITC with ratios of DMPC to telodendrimer of 99:1, 90:10, 50:50, 10:90 and 1:99.

Telo-NLPs support assembly of a functional membrane protein. Assembly of the soluble bacteriorhodopsin-NLP (bR-NLP) complex was observed within 4 h after addition of plasmids to an *E. coli* cell-free lysate (FIG. 7). Addition of telodendrimers to the cell-free reaction did not inhibit bacteriorhodopsin (bR) function as indicated by pink coloration of the tubes. The coloration is an indicator of function because it only occurs with proper folding and function of bR. The results indicated production of similar amounts of total bR protein produced with or without telodendrimers. As previously reported, the size range of NLPs was approximately 240 kDa with a smear on the gel that represented a heterogeneous size distribution, where Telo-NLP complex were slightly larger than NLPs alone. Some Telo-NLP complex heterogeneity was also observed by native gel electrophoresis. This heterogeneity may have been due to multiple telodendrimer interactions within the NLPs, which could potentially modify protein-lipid interactions.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate. Further, the computer readable form of the sequence listing of the ASCII text file P1799-USC-Seq-List-ST25 is incorporated herein by reference in its entirety.

SEQUENCES
(Homo sapiens apolipoproteinA-1 (APOA1), cDNA, NM_000039.1)
SEQ ID NO: 1
AGAGACTGCGAGAAGGAGGTCCCCCACGGCCCTTCAGGATGAAAGCTGCG

GTGCTGACCTTGGCCGTGCTCTTCCTGACGGGGAGCCAGGCTCGGCATTT

CTGGCAGCAAGATGAACCCCCCCAGAGCCCCTGGGATCGAGTGAAGGACC

TGGCCACTGTGTACGTGGATGTGCTCAAAGACAGCGGCAGAGACTATGTG

TCCCAGTTTGAAGGCTCCGCCTTGGGAAAACAGCTAAACCTAAAGCTCCT

TGACAACTGGGACAGCGTGACCTCCACCTTCAGCAAGCTGCGCGAACAGC

TCGGCCCTGTGACCCAGGAGTTCTGGGATAACCTGGAAAAGGAGACAGAG

GGCCTGAGGCAGGAGATGAGCAAGGATCTGGAGGAGGTGAAGGCCAAGGT

GCAGCCCTACCTGGACGACTTCCAGAAGAAGTGGCAGGAGGAGATGGAGC

TCTACCGCCAGAAGGTGGAGCCGCTGCGCGCAGAGCTCCAAGAGGGCGCG

CGCCAGAAGCTGCACGAGCTGCAAGAGAAGCTGAGCCCACTGGGCGAGGA

GATGCGCGACCGCGCGCGCGCCCATGTGGACGCGCTGCGCACGCATCTGG

CCCCCTACAGCGACGAGCTGCGCCAGCGCTTGGCCGCGCGCCTTGAGGCT

CTCAAGGAGAACGGCGGCGCCAGACTGGCCGAGTACCACGCCAAGGCCAC

CGAGCATCTGAGCACGCTCAGCGAGAAGGCCAAGCCCGCGCTCGAGGACC

TCCGCCAAGGCCTGCTGCCCGTGCTGGAGAGCTTCAAGGTCAGCTTCCTG

AGCGCTCTCGAGGAGTACACTAAGAAGCTCAACACCCAGTGAGGCGCCCG

CCGCCGCCCCCCTTCCCGGTGCTCAGAATAAACGTTTCCAAAGTGGG (Homo sapiens Δ49 apolipoproteinA-1 (Δ49A1), cDNA)
SEQ ID NO: 2
AGCGGCAGAGACTATGTGTCCCAGTTTGAAGGCTCCGCCTTGGGAAAACA

GCTAAACCTAAAGCTCCTTGACAACTGGGACAGCGTGACCTCCACCTTCA

GCAAGCTGCGCGAACAGCTCGGCCCTGTGACCCAGGAGTTCTGGGATAAC

CTGGAAAAGGAGACAGAGGGCCTGAGGCAGGAGATGAGCAAGGATCTGGA

GGAGGTGAAGGCCAAGGTGCAGCCCTACCTGGACGACTTCCAGAAGAAGT

GGCAGGAGGAGATGGAGCTCTACCGCCAGAAGGTGGAGCCGCTGCGCGCA

GAGCTCCAAGAGGGCGCGCGCCAGAAGCTGCACGAGCTGCAAGAGAAGCT

GAGCCCACTGGGCGAGGAGATGCGCGACCGCGCGCGCGCCCATGTGGACG

CGCTGCGCACGCATCTGGCCCCCTACAGCGACGAGCTGCGCCAGCGCTTG

GCCGCGCGCCTTGAGGCTCTCAAGGAGAACGGCGGCGCCAGACTGGCCGA

GTACCACGCCAAGGCCACCGAGCATCTGAGCACGCTCAGCGAGAAGGCCA

AGCCCGCGCTCGAGGACCTCCGCCAAGGCCTGCTGCCCGTGCTGGAGAGC

TTCAAGGTCAGCTTCCTGAGCGCTCTCGAGGAGTACACTAAGAAGCTCAA

CACCCAGTGAGGCGCCCGCCGCCGCCCCCCTTCCCGGTGCTCAGAATAAA

CGTTTCCAAAGTGGG (Homo sapiens apolipoproteinA-1 (APOA1), protein, NP_000030.1)
SEQ ID NO: 3
MKAAVLTLAVLFLIGSQARHFWQQDEPPQSPWDRVKDLATVYVDVLKDSG

RDYVSQFEGSALGKQLNLKLLDNWDSVTSTFSKLREQLGPVTQEFWDNLE

KETEGLRQEMSKDLEEVKAKVQPYLDDFQKKWQEEMELYRQKVEPLRAEL

QEGARQKLHELQEKLSPLGEEMRDRARAHVDALRTHLAPYSDELRQRLAA

RLEALKENGGARLAEYHAKATEHLSTLSEKAKPALEDLRQGLLPVLESFK

VSFLSALEFYIKKLNTQ (Homo sapiens Δ49 apolipoproteinA-1 (Δ49A1), protein)
SEQ ID NO: 4
SGRDYVSQFEGSALGKQLNLKLLDNWDSVTSTFSKLREQLGPVTQEFWDN

LEKETEGLRQEMSKDLEEVKAKVQPYLDDFQKKWQEEMELYRQKVERLRA

ELQEGARQKLHELQEKLSPLGEEMRDRARAHVDALRTHLAPYSDELRQRL

AARLEALKENGGARLAEYHAKATEHLSILSEKAKPALEDLRQGLLPVLES

FKVSFLSALEEYTKKLNTQ

What is claimed is:

1. A nanodisc comprising:
a membrane scaffold protein;
a telodendrimer;
a lipid; and
a cationic lipid.

2. The nanodisc of claim 1, wherein the membrane scaffold protein is apolipoprotein.

3. The nanodisc of claim 1, wherein the telodendrimer has the formula:

PEG-D-(R)$_n$ wherein
D is a dendritic polymer having a single focal group and a plurality of end groups;
PEG is polyethyleneglycol (PEG) of 1-100 kDa linked to the focal group of the dendritic polymer;
each R is independently selected from the group consisting of the end group of the dendritic polymer and an amphiphilic compound, such that when R is not an end group each R is linked to one of the end groups; and
subscript n is an integer from 2 to 20, wherein subscript n is equal to the number of end groups on the dendritic polymer, and wherein at least half the number n of R's are each an amphiphilic compound.

4. The nanodisc of claim 3, wherein the dendritic polymer is a poly(lysine) dendritic polymer wherein each end group is hydroxy.

5. The nanodisc of claim 3, wherein each amphiphilic compound is cholic acid (CA).

6. The nanodisc of claim 5, wherein the telodendrimer is selected from the group consisting of PEG$^{5k}$-D-CA$_8$, PEG$^{5k}$-D-CA$_4$ and PEG$^{2k}$-D-CA$_4$, wherein each dendritic polymer D is a poly(lysine) dendritic polymer wherein each end group is hydroxy.

7. The nanodisc of claim 1, wherein the lipid is selected from the group consisting of a phospholipid, cholesterol, a phosphatidylcholine, a phosphatidylethanolamine, a phosphatidylglycerol, a phosphatidylserine, and a phosphatidylinositol.

8. The nanodisc of claim 7, wherein the lipid is selected from the group consisting of 1,2-dipalmitoyl-sn-glycero-3-phosphocholine (DPPC), 1,2-ditetradecanoyl-sn-glycero-3-phosphocholine (DMPC), 1-tetradecanoyl-2-hexadecanoyl-sn-glycero-3-phosphocholine (MPPC), 1,2-dioctadecanoyl-sn-glycero-3-phosphocholine (DSPC), 1,2-distearoyl-sn-glycero-3-phosphoethanolamine (DSPE), 1,2-dihexadecanoyl-sn-glycero-3-phosphoethanolamine (DPPE), 1,2-distearoyl-sn-glycero-3-phospho-(1'-rac-glycerol) (DSPG), 1,2-dipalmitoyl-sn-glycero-3-phospho-(1'-rac-glycerol) (DPPG), 1-tetradecanoyl-2-hexadecanoyl-sn-glycero-3-phosphoglycerol (MPPG) and cholesterol.

9. The nanodisc of claim 7, wherein the lipid is DMPC.

10. The nanodisc of claim 1, further comprising a drug.

11. The nanodisc of claim 10, wherein the drug is selected from the group consisting of amphotericin B and SN38.

12. The nanodisc of claim 1, wherein the nanodisc is less than about 100 nm in size.

13. The nanodisc of claim 1, wherein the nanodisc is less than about 10 nm in size.

14. The nanodisc of claim 1, wherein the ratio of lipid to telodendrimer is from about 200:1 to about 5:1 (w/w).

15. The nanodisc of claim 1, wherein the ratio of lipid to telodendrimer is about 9:1 (w/w).

16. The nanodisc of claim 1, further comprising a targeting agent.

17. The nanodisc of claim 16, wherein the targeting agent comprises an antibody or antibody fragment specific for a target.

18. The nanodisc of claim 10, wherein the drug is a hydrophobic drug.

19. The nanodisc of claim 18, wherein the hydrophobic drug is selected from the group consisting of paclitaxel, doxorubicin, etoposide, SN-38, cyclosporin A, podophyllotoxin, carmustine, amphotericin B, ixabepilone, and rapamycin.

\* \* \* \* \*